(12) United States Patent
Guha et al.

(10) Patent No.: US 12,070,628 B2
(45) Date of Patent: Aug. 27, 2024

(54) LOW ENERGY IMMUNE PRIMING FOR TREATING CANCER AND METASTASIS

(71) Applicant: Montefiore Medical Center, Bronx, NY (US)

(72) Inventors: Chandan Guha, Scarsdale, NY (US); Stephen Barry, Haddonfield, NJ (US)

(73) Assignee: Montefiore Medical Center, Bronx, NY (US)

( * ) Notice: Subject to any disclaimer, the term of this patent is extended or adjusted under 35 U.S.C. 154(b) by 434 days.

(21) Appl. No.: 16/865,761

(22) Filed: May 4, 2020

(65) Prior Publication Data

US 2020/0398084 A1 Dec. 24, 2020

Related U.S. Application Data

(63) Continuation of application No. PCT/US2018/060138, filed on Nov. 9, 2018.
(Continued)

(51) Int. Cl.
*A61B 18/02* (2006.01)
*A61B 18/12* (2006.01)
(Continued)

(52) U.S. Cl.
CPC .............. *A61N 7/00* (2013.01); *A61K 49/223* (2013.01); *A61N 5/02* (2013.01); *A61N 7/02* (2013.01); *C07K 14/71* (2013.01); *C07K 16/2878* (2013.01); *A61B 8/4218* (2013.01); *A61B 8/485* (2013.01); *A61B 8/546* (2013.01); *A61B 2018/00613* (2013.01); *A61B 2018/00994* (2013.01); *A61B 2090/374* (2016.02);
(Continued)

(58) Field of Classification Search
CPC .... A61N 7/00; A61N 7/02; A61N 2007/0052; A61N 2007/0078; A61B 8/4218; A61B 8/546

See application file for complete search history.

(56) References Cited

U.S. PATENT DOCUMENTS 4,586,512 A * 5/1986 Do-huu ................ B06B 1/0625
  600/447
7,194,063 B2   3/2007 Dilmanian et al.
(Continued)

FOREIGN PATENT DOCUMENTS

CN     1947662 A    4/2007
CN   104874114 A    9/2015
(Continued)

OTHER PUBLICATIONS

Anelli et al. ERp44, a novel endoplasmic reticulum folding assistant of the thioredoxin family. EMBO J. 21(4):835-844 (2002).
(Continued)

*Primary Examiner* — Serkan Akar
*Assistant Examiner* — Amal Aly Farag
(74) *Attorney, Agent, or Firm* — Wilson Sonsini Goodrich & Rosati

(57) ABSTRACT

Disclosed herein are the systems, devices and methods for treating cancer and metastasis using low energy immune priming. The low energy immune priming includes administering immunopriming energy. The low energy immune priming can be combined with an adjunct therapy.

32 Claims, 33 Drawing Sheets

Specification includes a Sequence Listing.

Related U.S. Application Data

(60) Provisional application No. 62/596,715, filed on Dec. 8, 2017, provisional application No. 62/584,064, filed on Nov. 9, 2017.

(51) Int. Cl.
*A61K 49/22* (2006.01)
*A61N 5/02* (2006.01)
*A61N 5/10* (2006.01)
*A61N 7/00* (2006.01)
*A61N 7/02* (2006.01)
*C07K 14/71* (2006.01)
*C07K 16/28* (2006.01)
*A61B 8/00* (2006.01)
*A61B 8/08* (2006.01)
*A61B 18/00* (2006.01)
*A61B 90/00* (2016.01)

(52) U.S. Cl.
CPC .............. *A61N 2007/0004* (2013.01); *A61N 2007/0052* (2013.01); *A61N 2007/0078* (2013.01); *A61N 2007/0082* (2013.01); *C07K 2317/75* (2013.01)

(56) References Cited

U.S. PATENT DOCUMENTS

| | | | |
|---|---|---|---|
| 7,396,336 B2 | 7/2008 | Orszulak et al. | |
| 7,574,251 B2 | 8/2009 | Lu et al. | |
| 7,896,821 B1 | 3/2011 | Magnin et al. | |
| 10,974,077 B2 | 4/2021 | Guha et al. | |
| 2003/0055471 A1* | 3/2003 | Fenn | A61N 5/02 607/101 |
| 2004/0034304 A1* | 2/2004 | Sumi | G01S 7/52042 600/439 |
| 2005/0154431 A1 | 7/2005 | Quistgaard et al. | |
| 2007/0260144 A1* | 11/2007 | Sela | B01D 19/0084 600/472 |
| 2008/0260650 A1 | 10/2008 | Tawakol et al. | |
| 2009/0114846 A1 | 5/2009 | Blankenbecler | |
| 2009/0137996 A1 | 5/2009 | DeBenedictis | |
| 2010/0087728 A1 | 4/2010 | Jarvik et al. | |
| 2010/0092424 A1 | 4/2010 | Sanghvi et al. | |
| 2010/0106005 A1* | 4/2010 | Karczmar | A61N 7/02 601/2 |
| 2010/0234728 A1* | 9/2010 | Foley | A61B 8/0833 600/439 |
| 2010/0286673 A1 | 11/2010 | Altshuler et al. | |
| 2011/0137158 A1 | 6/2011 | Sumanaweera et al. | |
| 2013/0022957 A1* | 1/2013 | Chen | C12N 13/00 435/70.21 |
| 2013/0096595 A1 | 4/2013 | Myhr et al. | |
| 2014/0058293 A1* | 2/2014 | Hynynen | A61B 8/085 601/2 |
| 2014/0257146 A1 | 9/2014 | Kost et al. | |
| 2014/0276069 A1* | 9/2014 | Amble | A61B 8/4488 600/447 |
| 2015/0141810 A1* | 5/2015 | Weadock | A61N 5/1014 606/49 |
| 2015/0157383 A1 | 6/2015 | Chao et al. | |
| 2016/0345834 A1 | 12/2016 | Hasan et al. | |
| 2017/0271136 A1 | 9/2017 | Roder et al. | |
| 2017/0311804 A1* | 11/2017 | Herring | G01S 15/8913 |
| 2018/0154183 A1 | 6/2018 | Sahadevan | |
| 2019/0111131 A1 | 4/2019 | Nam et al. | |
| 2021/0268315 A1 | 9/2021 | Guha et al. | |
| 2022/0288418 A1 | 9/2022 | Guha et al. | |

FOREIGN PATENT DOCUMENTS

| | | |
|---|---|---|
| CN | 106470735 A | 3/2017 |
| JP | 2005526579 A | 9/2005 |
| JP | 2007007279 A | 1/2007 |
| JP | 2011527931 A | 11/2011 |
| WO | WO2001032258 * | 5/2001 ............... A61N 7/00 |
| WO | WO-2009070245 A2 | 6/2009 |
| WO | WO-2011128693 A1 | 10/2011 |
| WO | WO-2015067786 A1 | 5/2015 |
| WO | WO-2015160708 A1 | 10/2015 |
| WO | WO-2016196741 A2 | 12/2016 |
| WO | WO-2017079431 A1 | 5/2017 |
| WO | WO-2018126277 A1 | 7/2018 |
| WO | WO-2018126280 A1 | 7/2018 |
| WO | WO-2019094802 A1 | 5/2019 |
| WO | WO-2020123388 A1 | 6/2020 |
| WO | WO-2021041557 A1 | 3/2021 |

OTHER PUBLICATIONS

Back et al. ER stress signaling by regulated splicing: IRE1/HAC1/XBP1. Methods 35(4):395-416 (2005).

Basu et al. Calreticulin, a peptide-binding chaperone of the endoplasmic reticulum, elicits tumor- and peptide-specific immunity. J Exp Med 189:797¬-802 (1999).

Basu et al. Necrotic but not apoptotic cell death releases heat shock proteins, which deliver a partial maturation signal to dendritic cells and activate the NF-kappa B pathway. Int immunol 12:1539-1546 (2000).

Bethune et al. Personalized T cell-mediated cancer immunotherapy: progress and challenges. Curr Opin Biotechnol 48:142-152 (2017).

Boussiotis et al. Prevention of T cell anergy by signaling through the gamma c chain of the IL-2 receptor. Science 266:1039-1042 (1994).

Cancer Research Institute. Focused Ultrasound and Immunotherapy Workshop. New York. Downloaded from https://d3nqfeqdtaoni.cloudfront.net/images/pdf/FUS_Immunotherapy_Workshop_Summary.pdf (pp. 1-13) (2015).

Castelli et al. Human heat shock protein 70 peptide complexes specifically activate antimelanoma T cells. Cancer Res 61:222-227 (2001).

Chen et al. Tumor cell membrane-bound heat shock protein 70 elicits antitumor immunity. Immunol Lett 84:81-87 (2002).

Cuenca et al. Extra-lymphatic solid tumor growth is not immunologically ignored and results in early induction of antigen-specific T-cell anergy: dominant role of cross-tolerance to tumor antigens. Cancer Res 63:9007-9015 (2003).

Curiel et al. Specific recruitment of regulatory T cells in ovarian carcinoma fosters immune privilege and predicts reduced survival. Nat Med 10:942-949 (2004).

Dong et al. Tumor-associated B7-H1 promotes T-cell apoptosis: a potential mechanism of immune evasion. Nat Med 8:793-800 (2002).

Dougan et al. Immune therapy for cancer. Annu Rev Immunol 27:83-117 (2009).

Driessens et al. Costimulatory and coinhibitory receptors in anti-tumor immunity. Immunol Rev 229:126-144 (2009).

Dure et al. IL-2 signaling prevents T cell anergy by inhibiting the expression of anergy-inducing genes. Mol Immunol 46:999-1006 (2009).

Enk et al. Dendritic cells as mediators of tumor-induced tolerance in metastatic melanoma. Int J Cancer 73:309-316 (1997).

Gajewski et al. Cancer immunotherapy strategies based on overcoming barriers within the tumor microenvironment. Curr Opin Immunol 25:268-276 (2013).

Gao et al. Analysis of sirtuin 1 expression reveals a molecular explanation of IL-2-mediated reversal of T-cell tolerance. PNAS USA 109:899-904 (2012).

Gerlini et al. Metastatic melanoma secreted IL-10 down-regulates CD1 molecules on dendritic cells in metastatic tumor lesions. Am J Pathol 165:1853-1863 (2004).

Gramaglia et al. Ox-40 ligand: a potent costimulatory molecule for sustaining primary CD4 T cell responses. J Immunol 161:6510-6517 (1998).

Green et al. Immunogenic and tolerogenic cell death. Nat Rev Immunol 9:353-363 (2009).

(56) References Cited

OTHER PUBLICATIONS

Haug et al. The heat shock protein Hsp70 enhances antigen-specific proliferation of human CD4+ memory T cells. Eur J Immunol 35:3163-3172 (2005).
Hetz et al. Targeting the unfolded protein response in disease. Nat Rev Drug Discov 12:703-719 (2013).
Hu et al. Investigation of HIFU-induced anti-tumor immunity in a murine tumor model. J Transl Med 5:34 (2007).
Hu et al. Release of endogenous danger signals from HIFU-treated tumor cells and their stimulatory effects on APCs. Biochem Biophys Res Comm 335:124-131 (2005).
Huang et al. Gr-1+CD115+ immature myeloid suppressor cells mediate the development of tumor-induced T regulatory cells and T-cell anergy in tumor-bearing host. Cancer Res 66:1123-1131 (2006).
Jeong et al. Ultrasound Transducer and System for Real-Time Simultaneous Therapy and Diagnosis for Noninvasive Surgery of Prostate Tissue. IEEE Transactions on Ultrasonics Ferroelectrics, and Frequency Control 56(9):1913-1922 (Sep. 2009).
Jessop et al. ERp57 is essential or efficient folding of glycoproteins sharing common structural domains. EMBO J. 26(1):28-40 (2007).
Kon et al. Chaperone-mediated autophagy is required for tumor growth. Sci Transl Med. 3(109):109ra117 (2011).
Lan et al. Ablative Hypofractionated Radiotherapy Normalizes Tumor Vasculature in Lewis Lung Carcinoma Mice Model. Radiation Research 179(4):458-464 (2013).
Lathrop et al. A signal through OX40 (CD134) allows anergic, autoreactive T cells to acquire effector cell functions. J Immunol 172:6735-6743 (2004).
Leach et al. Enhancement of antitumor immunity by CTLA-4 blockade. Science 271:1734-1736 (1996).
Lee et al. Characterization of circulating T cells specific for tumor-associated antigens in melanoma patients. Nat Med 5:677-685 (1999).
Lewis et al. Design and characterization of a high-power ultrasound driver with ultralow-output impedance. Review of Scientific Instruments 80:114704 (2009).
Liu et al. Overcoming Immune Tolerance to Cancer by Heat Shock Protein Vaccines. Mol Cancer Ther 1:1147-1151 (2002).
Macian et al. Transcriptional mechanisms underlying lymphocyte tolerance. Cell 109(6):719-731 (Jun. 14, 2002).
Marangoni et al. The transcription factor NFAT exhibits signal memory during serial T cell interactions with antigen-presenting cells. Immunity 38:237-249 (2013).
Munn et al. Indoleamine 2,3-dioxygenase and tumor-induced tolerance. J Clin Invest 117:1147-1154 (2007).
Murata et al. OX40 costimulation synergizes with GM-CSF whole-cell vaccination to overcome established CD8+ T cell tolerance to an endogenous tumor antigen. J Immunol 176:974-983 (2006).
Obeid et al. Leveraging the immune system during chemotherapy: moving calreticulin to the cell surface converts apoptotic death from "silent" to immunogenic. Cancer Res 67:7941-7944 (2007).
Overwijk et al. Tumor regression and autoimmunity after reversal of a functionally tolerant state of self-reactive CD8+ T cells. J Exp Med 198:569-580 (2003).
Partanen et al. Reduction of peak acoustic pressure and shaping of heated region by use of multifoci sonications in MR-guided high-intensity focused ultrasound mediated mild hyperthermia. Med Phys 40(1):013301 (2013).
Pawaria et al. CD91-dependent programming of T-helper cell responses following heat shock protein immunization. Nat Commun 2:521 (2011).
PCT/US2016/035440 International Search Report and Written Opinion dated Mar. 17, 2017.
PCT/US2018/060138 International Search Report and Written Opinion dated Feb. 25, 2019.
PCT/US2018/060138 Invitation to pay fees dated Dec. 17, 2018.
Phan et al. Cancer regression and autoimmunity induced by cytotoxic T lymphocyte-associated antigen 4 blockade in patients with metastatic melanoma. PNAS USA 100:8372-8377 (2003).
Pouch et al. In vivo noninvasive temperature measurement by B-mode ultrasound imaging. J Ultrasound Med 29:1595-1606 (2010).
Rabinovich et al. Immunosuppressive strategies that are mediated by tumor cells. Annu Rev Immunol 25:267-296 (2007).
Ron et al. Signal integration in the endoplasmic reticulum unfolded protein response. Nat Rev Mol Cell Biol 8:519-529 (2007).
Rubinstein et al. Targeted inhibition of galectin-1 gene expression in tumor cells results in heightened T cell-mediated rejection; A potential mechanism of tumor-immune privilege. Cancer Cell 5:241-251 (2004).
Safford et al. Egr-2 and Egr-3 are negative regulators of T cell activation. Nat Immunol 6:472-480 (2005).
Saha et al. Low Intensity Focused Ultrasound (LOFU) Modulates Unfolded Protein Response and Sensitizes Prostate Cancer to 17AAG. Oncoscience 1(6):434-445 (2014).
Sahu et al. Live visualizations of single isolated tubulin protein self-assembly via tunneling current: effect of electromagnetic pumping during spontaneous growth of microtubule. Sci Rep 4:7303 (2014).
Sica et al. Altered macrophage differentiation and immune dysfunction in tumor development. J Clin Invest 117:1155-1166 (2007).
Somersan et al. Primary tumor tissue lysates are enriched in heat shock proteins and induce the maturation of human dendritic cells. J Immunol 167:4844-4852 (2001).
Soto-Nieves et al. Transcriptional complexes formed by NFAT dimers regulate the induction of T cell tolerance. J Exp Med 206:867-876 (2009).
Srivastava. Interaction of heat shock proteins with peptides and antigen presenting cells: chaperoning of the innate and adaptive immune responses. Annu Rev Immunol 20:395-425 (2002).
Staveley-O'Carroll et al. Induction of antigen-specific T cell anergy: An early event in the course of tumor progression. PNAS USA 95:1178-1183 (1998).
Ter Haar et al. Guidance on reporting ultrasound exposure conditions for bio-effects studies. Ultrasound Med Biol. 37(2):177-183 (2011).
Thomas et al. TGF-β Directly Targets Cytotoxic T Cell Functions During Tumor Evasion of Immune Surveillance. Cancer Cell 8:369-380 (2005).
Troy et al. Minimal recruitment and activation of dendritic cells within renal cell carcinoma. Clin Cancer Res 4:585-593 (1998).
Tsushima et al. Interaction between B7-H1 and PD-1 determines initiation and reversal of T-cell anergy. Blood 110:180-185 (2007).
Turk et al. Concomitant tumor immunity to a poorly immunogenic melanoma is prevented by regulatory T cells. J Exp Med 200:771-782 (2004).
Tutkun et al. A Cooperatively Controlled Robot for Ultrasound Monitoring of Radiation Therapy. Proceedings of the IEEE/RSJ International Conference on Intelligent Robots and Systems 2013:3071-3076 (Nov. 2013).
Udono et al. Comparison of tumor-specific immunogenicities of stress-induced proteins gp96, hsp90, and hsp70. J Imunol 152:5398-5403 (1994).
Udono et al. Heat shock protein 70-associated peptides elicit specific cancer immunity. J Exp Med 178:1391-1396 (1993).
Ullrich et al. A mouse tumor-specific transplantation antigen is a heat shock-related protein. PNAS USA 83:3121-3125 (1986).
U.S. Appl. No. 15/578,892 Office Action dated Mar. 27, 2020.
Uyttenhove et al. Evidence for a tumoral immune resistance mechanism based on tryptophan degradation by indoleamine 2,3-dioxygenase. Nat Med 9:1269-1274 (2003).
Valdor et al. Induction and stability of the anergic phenotype in T cells. Semin Immunol 25:313-320 (2013).
Van Elsas et al. Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med 190:355-366 (1999).
Vega et al. Hsp70 translocates into the plasma membrane after stress and is released into the extracellular environment in a membrane-associated form that activates macrophages. J Immunol 180:4299-4307 (2008).

(56) References Cited

OTHER PUBLICATIONS

White. Deconvoluting the context-dependent role for autophagy in cancer. Nat Rev Cancer 12(6):401-410 (2012).
Wilcox et al. Ligation of CD137 receptor prevents and reverses established energy of CD8+ cytolytic T lymphocytes in vivo. Blood 103:177-184 (2004).
Willimsky et al. Sporadic immunogenic tumours avoid destruction by inducing T-cell tolerance. Nature 437:141-146 (2005).
Yu et al. Identification of Prognosis-Relevant Subgroups in Patients with Chemoresistant Triple Negative Breast Cancer. Clin Cancer Res 19(10):1-18 (2013).
Zhang et al. CD40 ligation reverses T cell tolerance in acute myeloid leukemia. J Clin Invest 123:1999-2010 (2013).
Zhang et al. Hyperthermia on immune regulation: a temperature's story. Cancer Lett 271:191-204 (2008).
Zheng et al. Transcriptional regulator early growth response gene 2 (Egr2) is required for T cell anergy in vitro and in vivo. J Exp Med 209:2157-2163 (2012).
U.S. Appl. No. 15/578,892 Office Action dated Aug. 19, 2020.
U.S. Appl. No. 17/191,497 Non-Final Office Action dated Nov. 25, 2022.
Agoni et al. Variant splicing and influence of ionizing radiation on human endogenous retrovirus K (HERV-K) transcripts in cancer cell lines. PLoS One 8(10):e76472 (2013).
Apetoh et al. Toll-like receptor 4-dependent contribution of the immune system to anticancer chemotherapy and radiotherapy. Nat Med 13(9):1050-1059 (2007).
Benci et al. Tumor Interferon Signaling Regulates a Multigenic Resistance Program to Immune Checkpoint Blockade. Cell 167(6):1540-1554 (2016).
Billiard et al. Abdominal γ-radiation induces an accumulation of function-impaired regulatory T cells in the small intestine. International Journal of Radiation Oncology Biology Physics 80(3):869-76 (2011).
Chakraborty et al. Irradiation of tumor cells up-regulates Fas and enhances CTL lytic activity and CTL adoptive immunotherapy. J Immunol 170(12):6338-47 (2003).
Chakravarty et al. Flt3L therapy following localized tumor irradiation generates long-term protective immune response in metastatic lung cancer: its implication in designing a vaccination strategy. Oncology 70(4):245-254 (2006).
Chakravarty et al. Flt3-Ligand Administration after Radiation Therapy Prolongs Survival in a Murine Model of Metastatic Lung Cancer. Cancer Res 59(24):6028-6032 (1999).
Crittenden et al. Current clinical trials testing combinations of immunotherapy and radiation. Semin Radiat Oncol 25(1):54-64 (2015).
Crittenden et al. Expression of arginase I in myeloid cells limits control of residual disease after radiation therapy of tumors in mice. Radiat Res 182(2):182-90 (2014).
Demaria et al. Immune-mediated inhibition of metastases after treatment with local radiation and CTLA-4 blockade in a mouse model of breast cancer. Clin Cancer Res 11(2 Pt 1):728-34 (2005).
Demaria et al. Ionizing Radiation Inhibition of Distant Untreated Tumors (Abscopal Effect) is Immune Mediated. Int J radiat Oncol Biol Phys 58(3):862-870 (2004).
Dewan et al. Fractionated but not single-dose radiotherapy induces an immune-mediated abscopal effect when combined with anti-CTLA-4 antibody. Clin Cancer Res 15(17):5379-5388 (2009).
Filatenkov et al. Ablative Tumor Radiation Can Change the Tumor Immune Cell Microenvironment to Induce Durable Complete Remissions. Clin Cancer Res 21(16):3727-39 (2015).
Formenti et al. Systemic effects of local radiotherapy. Lancet Oncol 10(7):718-26 (2009).
Gameiro et al. Radiation-induced immunogenic modulation of tumor enhances antigen processing and calreticulin exposure, resulting in enhanced T-cell killing. Oncotarget 5(2):403-16 (2014).
Garcia-Barros et al. Tumor response to radiotherapy regulated by endothelial cell apoptosis. Science 300(5622):1155-9 (2003).
Golden et al. Radiation fosters dose-dependent and chemotherapy-induced immunogenic cell death. Oncoimmunology 3:e28518 (2014).
Gorchs et al. Cancer-associated fibroblasts from lung tumors maintain their immunosuppressive abilities after high-dose irradiation. Front Oncol 5:87 (2015).
Gough et al. The impact of the myeloid response to radiation therapy. Clin Dev Immunol 2013:281958 (2013).
Greco et al. Predictors of local control after single-dose stereotactic image-guided intensity-modulated radiotherapy for extracranial metastases. Int J Radiat Oncol Biol Phys 79(4):1151-7 (2011).
Hallahan et al. Targeting drug delivery to radiation-induced neoantigens in tumor microvasculature. J Control Release 74(1-3):183-91 (2001).
Hoyer et al., Radiotherapy for liver metastases: a review of evidence. Int J Radiat Oncol Biol Phys. 82(3):1047-1057 (2012).
Janiak et al. Cancer immunotherapy: how low-level ionizing radiation can play a key role. Cancer Immunology, Immunotherapy 66(7):819-32 (2017).
Kachikwu et al. Radiation enhances regulatory T cell representation. Int J Radiat Oncol Biol Phys 81(4):1128-35 (2011).
Kawashita et al. An autologous in situ tumor vaccination approach for hepatocellular carcinoma. 1. Flt3 ligand gene transfer increases antitumor effects of a radio-inducible suicide gene therapy in an ectopic tumor model. Radiat Res 182(2):191-200 (2014).
Kawashita et al. An autologous in situ tumor vaccination approach for hepatocellular carcinoma. 2. Tumor-specific immunity and cure after radio-inducible suicide gene therapy and systemic CD40-ligand and Flt3-ligand gene therapy in an orthotopic tumor model. Radiat Res 182(2):201-210 (2014).
Kioi et al. Inhibition of vasculogenesis, but not angiogenesis, prevents the recurrence of glioblastoma after irradiation in mice. J Clin Invest 120(3):694-705 (2010).
Klug et al. Low-dose irradiation programs macrophage differentiation to an iNOS+/M1 phenotype that orchestrates effective T cell immunotherapy. Cancer cell 24(5):589-602 (2013).
Kozin et al. Recruitment of myeloid but not endothelial precursor cells facilitates tumor regrowth after local irradiation. Cancer Res 70(14):5679-85 (2010).
Lee et al. Therapeutic effects of ablative radiation on local tumor require CD8+ T cells: changing strategies for cancer treatment. Blood 114(3):589-95 (2009).
Liu. Cancer control related to stimulation of immunity by low-dose radiation. Dose-response 5(1):39-47 (2007).
Liu et al. Enhancement of antitumor immunity by low-dose total body irradiation is associated with selectively decreasing the proportion and number of T regulatory cells. Cellular & Molecular immunology 7(2):157 (2010).
Liu et al. Low-Dose Total Body Irradiation Can Enhance Systemic Immune Related Response Induced by Hypo-Fractionated Radiation. Front Immunol 10:317 (2019).
Marconi et al. A meta-analysis of the abscopal effect in preclinical models: Is the biologically effective dose a relevant physical trigger? PLoS One 12(2):e0171559 (2017).
Martinez-Zubiaurre et al. Radiation-Induced Transformation of Immunoregulatory Networks in the Tumor Stroma. Front Immunol 9:1679 (2018).
Menon et al. Influence of low-dose radiation on abscopal responses in patients receiving high-dose radiation and immunotherapy. J Immunother Cancer 7:237 (2019).
Miller et al. Changes in the activation and reconstitution of lymphocytes resulting from total-body irradiation correlate with slowed tumor growth. Oncology 65(3):229-41 (2003).
Minn et al. Combination Cancer Therapies with Immune Checkpoint Blockade: Convergence on Interferon Signaling. Cell 165(2):272-275 (2016).
Morris et al. Tumor-Specific Inhibition of In Situ Vaccination by Distant Untreated Tumor Sites. Cancer Immunol Res 6(7):825-34 (2018).
North. Gamma-Irradiation facilitates the expression of adoptive immunity against established tumors by eliminating suppressor T cells. Cancer Immunology, Immunotherapy 16(3):175-81 (1984).
North. Radiation-induced, immunologically mediated regression of an established tumor as an example of successful therapeutic immunomanipulation. Preferential elimination of suppressor T cells

(56) References Cited

OTHER PUBLICATIONS allows sustained production of effector T cells. Journal of Experimental Medicine 164(5):1652-66 (1986).

Obeid et al. Calreticulin exposure dictates the immunogenicity of cancer cell death. Nat Med 13(1):54-61 (2007).

PCT/US2020/048020 International Search Report and Written Opinion dated Feb. 12, 2021.

Reits et al. Radiation modulates the peptide repertoire, enhances MHC class I expression, and induces successful antitumor immunotherapy. J Exp Med 203(5):1259-71 (2006).

Savage et al., Postablation modulation after single high-dose radiation therapy improves tumor control via enhanced immunomodulation. Clin Cancer Res. 26(4):910-921 (2020).

Schaue et al. Regulatory T cells in radiotherapeutic responses. Front Oncol 2:90 (2012).

Seetharam et al. Enhanced eradication of local and distant tumors by genetically produced interleukin-12 and radiation. Int J Oncol 15(4):769-73 (1999).

Seung et al. Phase 1 study of stereotactic body radiotherapy and interleukin-2—tumor and immunological responses. Sci Transl Med 4(137):137ra74 (2012).

Shimura et al. Effects of low-dose-gamma rays on the immune system of different animal models of disease. Does Response 12(3):429-465 (2014).

Stone et al. Effect of host immune capability on radiocurability and subsequent transplantability of a murine fibrosarcoma. J Natl Cancer Inst 63(5):1229-35 (1979).

Timmerman et al. Stereotactic body radiation therapy for inoperable early stage lung cancer. JAMA 303(11):1070-1076 (2010).

Vanpouille-Box et al. DNA exonuclease Trex1 regulates radiotherapy-induced tumour immunogenicity. Nat Commun 8:15618 (2017).

Vanpouille-Box et al. TGFbeta is a Master Regulator of Radiation Therapy-Induced Antitumor Immunity. Cancer Res 75(11):2232-42 (2015).

Wennerberg et al. Barriers to Radiation-Induced In Situ Tumor Vaccination. Front Immunol 8:229 (2017).

Yamada et al. High-dose, single-fraction image-guided intensity-modulated radiotherapy for metastatic spinal lesions. Int J Radiat Oncol Biol Phys 71(2):484-90 (2008).

Zhang et al. An in situ autologous tumor vaccination with combined radiation therapy and TLR9 agonist therapy. PLoS One 7(5):e3811 (2012).

Zhang et al. Induced sensitization of tumor stroma leads to eradication of established cancer by T cells. J Exp Med 204(1):49-55 (2007).

Znati et al. Irradiation reduces interstitial fluid transport and increases the collagen content in tumors. Clin Cancer Res 9(15):5508-13 (2003).

U.S. Appl. No. 17/191,497 Final Office Action dated Jul. 7, 2023.

EP16804398.2 Extended European Search Report dated Jan. 19, 2022.

EP18876112.6 Extended European Search Report dated Jul. 28, 2021.

EP20857760.1 Extended European Search Report dated Oct. 5, 2023.

U.S. Appl. No. 15/578,892 Notice of Allowance dated Dec. 9, 2020.

U.S. Appl. No. 17/191,497 Office Action dated Nov. 21, 2023.

\* cited by examiner

D

E

F

G

H

LOW ENERGY IMMUNE PRIMING FOR TREATING CANCER AND METASTASIS

CROSS-REFERENCE TO RELATED APPLICATIONS

This application is a continuation of International Patent Application No. PCT/US18/60138, filed Nov. 9, 2018, which claims the benefit of U.S. Provisional Application No. 62/584,064, filed Nov. 9, 2017, and U.S. Provisional Application No. 62/596,715, filed Dec. 8, 2017, which application is incorporated herein by reference. The subject matter of this application is related to PCT/US2016/035440, the entire disclosure of which is incorporated herein by reference.

STATEMENT OF GOVERNMENT SUPPORT

This invention was made with government support under RO1EB009040 awarded by the National Institute of Biomedical Imaging and Bioengineering (NIBIB). The government has certain rights in the invention.

SEQUENCE LISTING

The instant application contains a Sequence Listing which has been filed electronically in ASCII format and is hereby incorporated by reference in its entirety. Said ASCII copy, created on May 19, 2020, is named 52650-701_301_SL.txt and is 5,791 bytes in. size.

BACKGROUND OF THE INVENTION

Cancers are diseases in which genetically mutated cells proliferate uncontrollably, draining nutrients and disrupting the functions of healthy tissues. Traditional cancer treatments, such as surgery, chemotherapy and radiation can eradicate cancer cells and the tumors in which they reside, but may not serve to fully suppress the cancer. The use of immunotherapies to engage cells of the immune system to seek out and eliminate cancer cells has been proposed, but this approach can have less than ideal results in at least some instances. For example, the tumor can generate a microenvironment which is a privileged site that can evade immunotherapy. Also, the presentation of antigens by cancer cells can be less than ideal in at least some respects.

Although ultrasound has been proposed in combination with other therapies for the treatment of cancer, the prior ultrasound methods and apparatus can be less than ideal in at least some respects. For example, high intensity focused ultrasound can take greater amounts of time to treat a tumor than would be ideal and it instantaneously destroys the tumor microenvironment by a process called coagulative necrosis, thereby preventing immune cell infiltration in the tumor to engulf and present tumor associated antigens (TAA). Thus, it would be helpful if other types of sub-ablative energy could be used to treat cancer.

In light of the above, improved methods and apparatus of treating cancer are needed. Ideally, the methods and apparatus would generate an in situ vaccine to treat cancer, in which the patient's immune system generates an immune response against the cancer. The methods and apparatus can be configured to treat cancer with a sub-ablative dose of energy, so as to generate an immunogenic response when combined with other therapies.

SUMMARY OF THE INVENTION

In some embodiments, disclosed herein is an acoustic priming therapy system comprising: a processor; one or more ultrasound transducers coupled to the processor, the ultrasound transducers configured to produce one or more ultrasound beams such that the frequency waveform of the one or more ultrasound beams has a spatial peak temporal average acoustic output intensity ($I_{spta}$) of between 10 and 900 W/cm$^2$ and a beam volume of at least 0.5 cm$^3$; and a probe coupled to the processor the probe configured to monitor the patient. In some embodiments, the processor and the ultrasound transducer are configured to scan tissue volumetrically at a rate of at least about 0.5 cm$^3$ per second. In some embodiments, the rate of scanning of the total tissue volume is within a range from about 0.5 cm$^3$ to about 50 cm$^3$ per second. In some embodiments, the volume of the entire tissue has been scanned. In some embodiments, the total tissue volume is at least about 2 cm$^3$. In some embodiments, the total tissue volume is within a range from about 0.5 cm$^3$ to about 1000 cm$^3$, In some embodiments, the total tissue volume is within a range from about 1 cm$^3$ to about 500 cm$^3$. In some embodiments, the total tissue volume is within a range from about 1 cm$^3$ to about 250 cm$^3$ In some embodiments, the intensity is within a range from about 20 W/cm$^2$ to about 500 W/cm$^2$. In some embodiments, the processor is configured with instructions to overlap the plurality of locations. In some embodiments, the processor is configured with instructions to move the ultrasound transducer from a first location corresponding to a first volumetric region to a second location corresponding to a second volumetric region while the transducer transmits the ultrasound beam. In some embodiments, the system further comprises a linkage coupled to the one or more ultrasound transducers, the processor coupled to the linkage and configured with instructions to move the one or more ultrasound transducers to the plurality of locations. In some embodiments, the linkage comprises a robotic arm comprising a plurality of joints, each of the plurality of joints coupled to an actuator to control an angle of the joint and wherein the processor is configured with instructions to determine a plurality of angles of the plurality of joints to direct the ultrasound beam to the plurality of locations. In some embodiments, the robotic arm comprises a plurality of fingers, and wherein each of the plurality of fingers is coupled to a transducer mounted thereon and wherein each of the plurality of fingers is configured to control an angle of the transducer of an ultrasound beam from the transducer mounted on the finger to direct the ultrasound beam to a target location. In some embodiments, the processor is configured to control an orientation of the ultrasound transducer at each of the plurality of locations in order to align the ultrasound transducer with a surface of a skin of the patient at each of the plurality of locations. In some embodiments, the processor is configured to control an orientation of the ultrasound transducer at each of the plurality of locations in order to align the ultrasound transducer with a surface of a skin of the patient at each of the plurality of locations and optionally wherein each of the plurality of locations corresponds to a position in three dimensions and an orientation in three dimensions in order to position the transducer with six degrees of freedom. In some embodiments, the system further comprises a user input for a user to specify an adjunct therapy to be combined with the ultrasound treatment, and wherein the processor is configured with instructions to record a time of treatment of the ultrasound beam to the tissue and output a time for the adjunct therapy and optionally wherein the adjunct therapy is selected from the group consisting of radiotherapy, chemotherapy, immunotherapy, Irreversible Electroporation (IRE), Microwave therapy, Low-Intensity Focused Ultrasound (LOFU), and High-Intensity Focused Ultrasound (HIFU), and optionally wherein the output time comprises a time window for the adjunct therapy. In some embodiments, the processor is configured with instructions to provide user interface to a user, the user interface comprising an image of a tumor of the patient and input treatment locations. In some embodiments, the processor is configured to perform tissue elastography of the total tissue volume. In some embodiments, the processor is configured to receive diffusion parameters as input. In some embodiments, the probe is an imaging probe. In some embodiments, the probe is a thermometer. In some embodiments, the probe is a thermocouple. In some embodiments, the probe is a fiber optic temperature probe. In some embodiments, the processor is configured to issue a temperature readout. In some embodiments, the processor is configured to issue a temperature alarm. In some embodiments, the probe comprises a separate transducer that measures ultrasound. In some embodiments, the probe uses elastography to monitor treatment the effect on the tissues. In some embodiments, the system further comprises a cooling system. In some embodiments, the adjunct therapy is radiotherapy. In some embodiments, the radiotherapy is sub-ablative. In some embodiments, the adjunct therapy is IRE. In some embodiments, the IRE is administered for a period of about 30 seconds to about 180 seconds. In some embodiments, the adjunct therapy is microwave therapy. In some embodiments, the microwave therapy is administered for a period of about 1 second to about 60 seconds, and the power is about 1 W to about 10 W. In some embodiments, the adjunct therapy is LOFU. In some embodiments, the LOFU has a spatial peak temporal average acoustic output intensity ($I_{spta}$) of about 1 to 1,000 W/cm². In some embodiments, the LOFU has an acoustic power of about 3 W to 32 W. In some embodiments, the LOFU is administered for a period of about 0.5 seconds to about 5 seconds. In some embodiments, the adjunct therapy is HIFU. In some embodiments, the HIFU has a spatial peak temporal average acoustic output intensity ($I_{spta}$) of about 1,000 to 2,000 W/cm². In some embodiments, the HIFU has an acoustic power of about 1 W to 20 W. In some embodiments, the HIFU is administered for a period of about 1 second to about 10 seconds. In some embodiments, the adjunct therapy is chemotherapy. In some embodiments, the chemotherapy comprises administering a chemotherapeutic. In some embodiments, the chemotherapeutic is a proteosome inhibitor, PI3-kinase inhibitor, autophagy inhibitor, mTOT inhibitor, PPARγ agonist, Cox-2 inhibitor, Ca channel inhibitor, ER stress inducer, CHOP modulator, nucleoside analog, eIF2α phosphatase inhibitor, protein ligand, or HSP90 inhibitor. In some embodiments, the chemotherapeutic is Bortezomib, 3-methyladenine, polyphenol (green tea) epigallocatechin gallate, genistein, curcumin, resveratrol, 15,16-dihydrotanshinone I (Tanshen root), chloroquine, rapamycin, temsirolimus, 4-O-carboxymethyl ascochlorin, Celecoxib, Verapamil, Ritonavir, 3-thia fatty acid, tetradecylthioacetic acid, Nelfinavir, cisplatin, gemcitabine, salubrinal, cycloheximide, TRAIL, 4-phenylbutyric acid, geldanamycin, 17-allyamino-17-demethoxy-geldanamycin (17AAG), 17-dimethylamino-ethylamino-17-demethoxy-geldanamycin (17DMAG), or vacuolin. In some embodiments, the chemotherapeutic is an HSP90 inhibitor. In some embodiments, the chemotherapeutic is 17-allyamino-17-demethoxy-geldanamycin (17AAG). In some embodiments, the adjunct therapy is immunotherapy. In some embodiments, the immunotherapy is selected from the group consisting of dendritic cell targeted therapy, effector T cell targeting, immune checkpoint inhibition. In some embodiments, the dendritic cell targeted therapy comprises a dendritic cell targeted therapy immunotherapeutic selected from the group consisting of Flt3L, CD40L, GM-CSF, RIG1 helicase activators, anti-CD40, NKG2D ligand, anti-CSF1R, anti-TLR, TLR ligands, INF-α, and TNF-β. In some embodiments, the effector T cell targeting comprises a T cell targeting immunotherapeutic selected from the group consisting of anti-OX40, 4-1BBL, anti-foxp40, TGF-β inhibitor, anti-CD137, artificial immunological synapse for T-cell activation, anti-CD47, anti-CD27 and anti-GD2. In some embodiments, the immune checkpoint inhibition comprises an immune checkpoint immunotherapeutic selected from the group consisting of anti-CTL4, anti-PD1, anti-VISTA, tim3, IDO inhibitor, Norharmane, Rosamarinic acid, COX-2 inhibitors, 1-Methyltryptophan, Epacadostat, and navoximod.

In some embodiments, disclosed herein is a method of treating a patient, the method comprising: administering an immunopriming energy selected from the group consisting of Irreversible Electroporation (IRE), Microwave, Low-Intensity Focused Ultrasound (LOFU), High-Intensity Focused Ultrasound (HIFU), Radiofrequency energy and cryotherapy; and administering an immunotherapy selected from the group consisting of dendritic cell targeted therapy, effector T cell targeting, immune checkpoint inhibition. In some embodiments, the dendritic cell targeted therapy comprises a dendritic cell targeted therapy immunotherapeutic selected from the group consisting of Flt3L, CD40L, GM-CSF, RIG1 helicase activators, anti-CD40, NKG2D ligand, anti-CSFIR,anti-TLR, TLR ligands, INF-α, and TNF-β. In some embodiments, the effector T cell targeting comprises a T cell targeting immunotherapeutic selected from the group consisting of anti-OX40, 4-1BBL, anti-foxp40, TGF-β inhibitor, anti-CD137, artificial immunological synapse for T-cell activation, anti-CD47, anti-CD27 and anti-GD2. In some embodiments, the immune checkpoint inhibition comprises an immune checkpoint immunotherapeutic selected from the group consisting of anti-CTL4, anti-PD1, anti-VISTA, tim3, IDO inhibitor, Norharmane, Rosamarinic acid, COX-2 inhibitors, 1-Methyltryptophan, Epacadostat, and navoximod.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

OTII mice were challenged with $3\times10^5$ B16-F1-OVA melanoma cells as described. T cells were stimulated with OVA323-339 peptide-loaded splenocytes and IL-2 and IFNγ production measured by ELISA. 1E-F. B16-F1 cells were used to induce tumors in Tyrp1 mice as described above. Isolated CD4+ T cells were stimulated with anti-CD3 and anti-CD28 antibodies and IL-2 and IFNγ production determined by ELISA. Graphs show mean±SEM from 4 (1A-B) or 3 (1C-F) independent experiments. Results are shown as mean±SEM from 3-5 mice for each experiment. Data were analyzed using ANOVA with a Tukey post-test (* $P<0.01$;  $P<0.01$;* $P<0.05$).

FIG. 2A-2D. Treatment of melanoma tumors with LOFU overcomes tumor induced CD4+ T cell tolerance: 2A-B. Tumors were induced in C57Bl/6 mice by s.c. injection of $3\times10^5$ B16-F1 melanoma cells in the lumbar flank. Tumors were left untreated or treated with LOFU. Thirty-six hours after FUS treatment, CD4+ T cells were isolated from tumor DLN or NDLNs and stimulated with anti-CD3 and anti-CD28 antibodies. IL-2 and IFNγ production was assessed by ELISA. The results (total cytokine production and ratio of the levels of cytokines produced by T cells from NDLN and DLN in each group) are presented as mean±SEM from 3 different mice per condition. Differences between cytokine production of DLN T cells in untreated or treated mice were analyzed using a 2-tailed t test (*$P<0.05$). 2C. Mice were challenged with $3\times10^5$ B16 melanoma cells to induce tumors. Following tumor development total RNA samples were extracted from CD4+ T cells isolated from the DLN and NDLN of tumor-bearing mice, and tumor-free control mice. Expression of anergy-associated genes was measured by quantitative RT-PCR. The results are shown as fold induction of gene expression in the DLN or NDLN resident T cells in tumor bearing mice compared to T cells isolated from tumor-free mice. The data represent mean±SEM from 3 independent experiments. 2D. B16-F1 melanoma tumors were induced in Tyrp1 mice that were then left untreated or treated with LOFU. The expression of different anergy-associated genes was measured by RT-PCR in CD4+ T cells isolated from the DLNs and NDLNs. Expression of the anergy-associated genes is presented as fold induction (mean±SEM from 5 independent experiments) over the values obtained in T cells from Tyrp1 mice bearing no tumor.

Figure 3A:
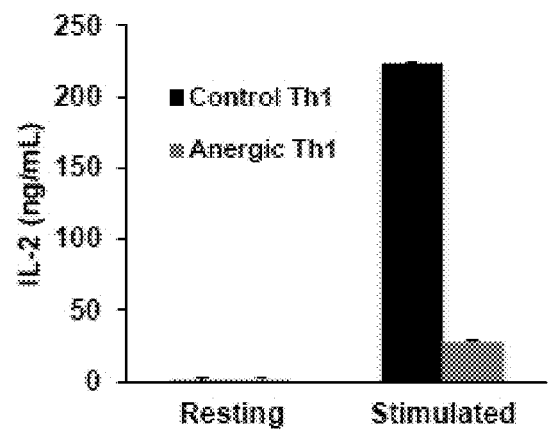
Figure 3B:
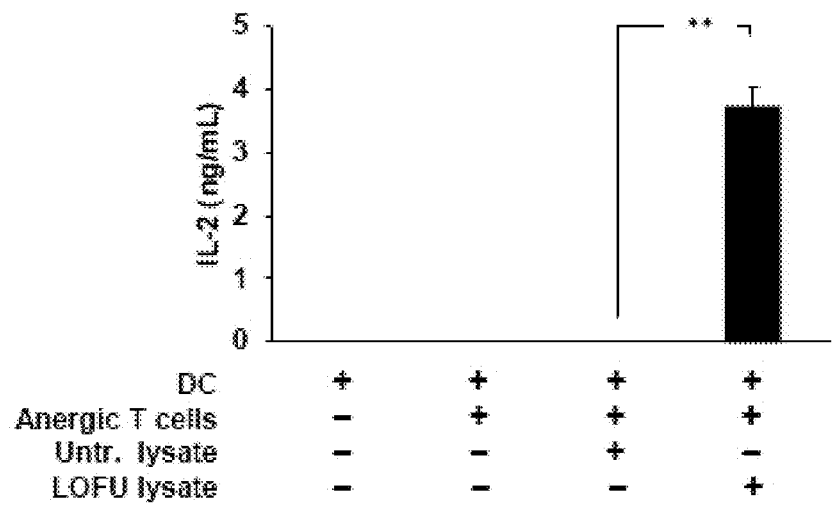

FIG. 3A-3B. Lysates from LOFU-treated B16-F1 melanoma tumors can reverse the hyporesponsive state of anergic T cells 3A. Naive CD4+ T cells were isolated from spleens and lymph nodes of Tyrp1 mice, and differentiated into TH1 cells. Cells were then either left untreated or treated with anti-CD3 alone for 16 hours to induce anergy. Cells were then rested for 72 hours in strict absence of IL-2 and re-stimulated with anti-CD3 and anti-CD28 antibodies. IL-2 levels were measured by ELISA. The results are shown as mean±SEM from 2 independent experiments. 3B. CD11c+ dendritic cells were isolated from spleens of tumor-free Tyrp1 mice. Anergic TH1 cells generated from Tyrp1 mouse-derived CD4+ T cells as described in (3A) were co-cultured with the dendritic cells and tumor lysates derived from untreated or LOFU-treated B16-F1 melanoma tumors. Supernatants were collected after 24 hours and assayed for IL-2 by ELISA. Results are shown as mean±SEM from 2 independent experiments with 3 independent sets of tumor lysates used in each experiment. Data were analyzed using ANOVA with a Tukey post-test (** $P<0.01$).

FIG. 4A-4D. FUS treatment causes changes in expression and cellular distribution of Hsp70 and calreticulin in B16-F1 melanoma cells. 4A. Total DLNs resident cells from untreated and LOFU-treated B16-F1 melanoma-bearing mice were isolated and immunostained for CD11c to gate dendritic cells. Surface expression of B7.1, B7.2 and MHCII was then assessed by flow cytometry. Appropriate isotype controls were used for each primary antibody. Representative histograms are shown. 4B. Representative FACS dot plot of B16 tumor cell suspension obtained from untreated or LOFU treated mice were stained with a viability marker (Live/dead Mk). Relative quantification of dead cells is reported. Box and arrow indicate dead cells (Live/dead MK+). 4C. Immunofluorescence staining of B16-F1 tumor tissues isolated from untreated mice or from mice treated with LOFU. Tissue sections were stained with antibodies to detect calreticulin or Hsp70 and TRP1. Nuclei were stained with DAPI. Magnification 60×. 4D. Cells from tumors of LOFU treated mice and untreated mice were stained for CD45 and for the expression of TRP1. CD45-TRP1+B16 cells were then analyzed for the expression of Hsp70. A representative histogram is shown. Gates and arrows indicate the selected population for the analysis.

Figure 5A:
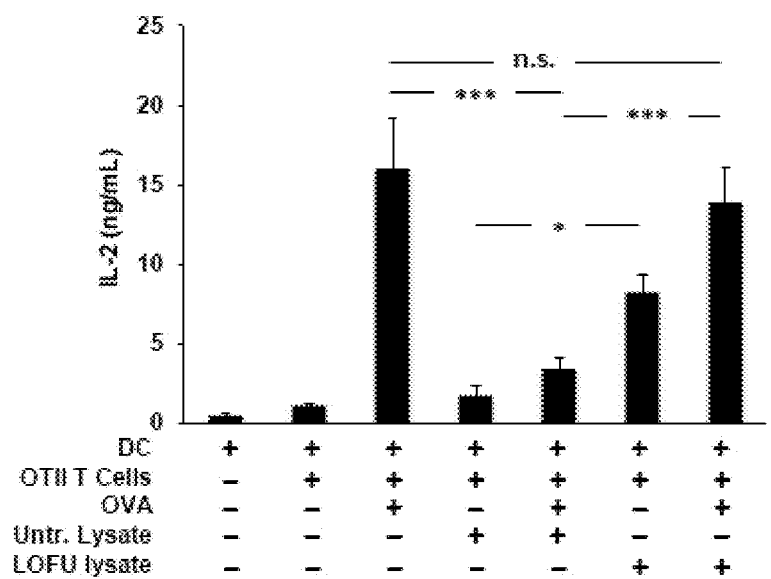
Figure 5B:
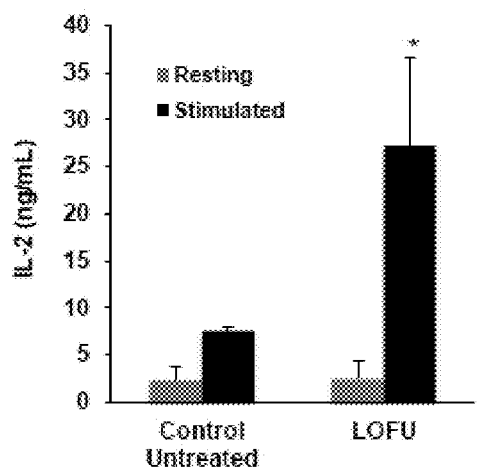
Figures 6A, 6B, 6C, 6D:
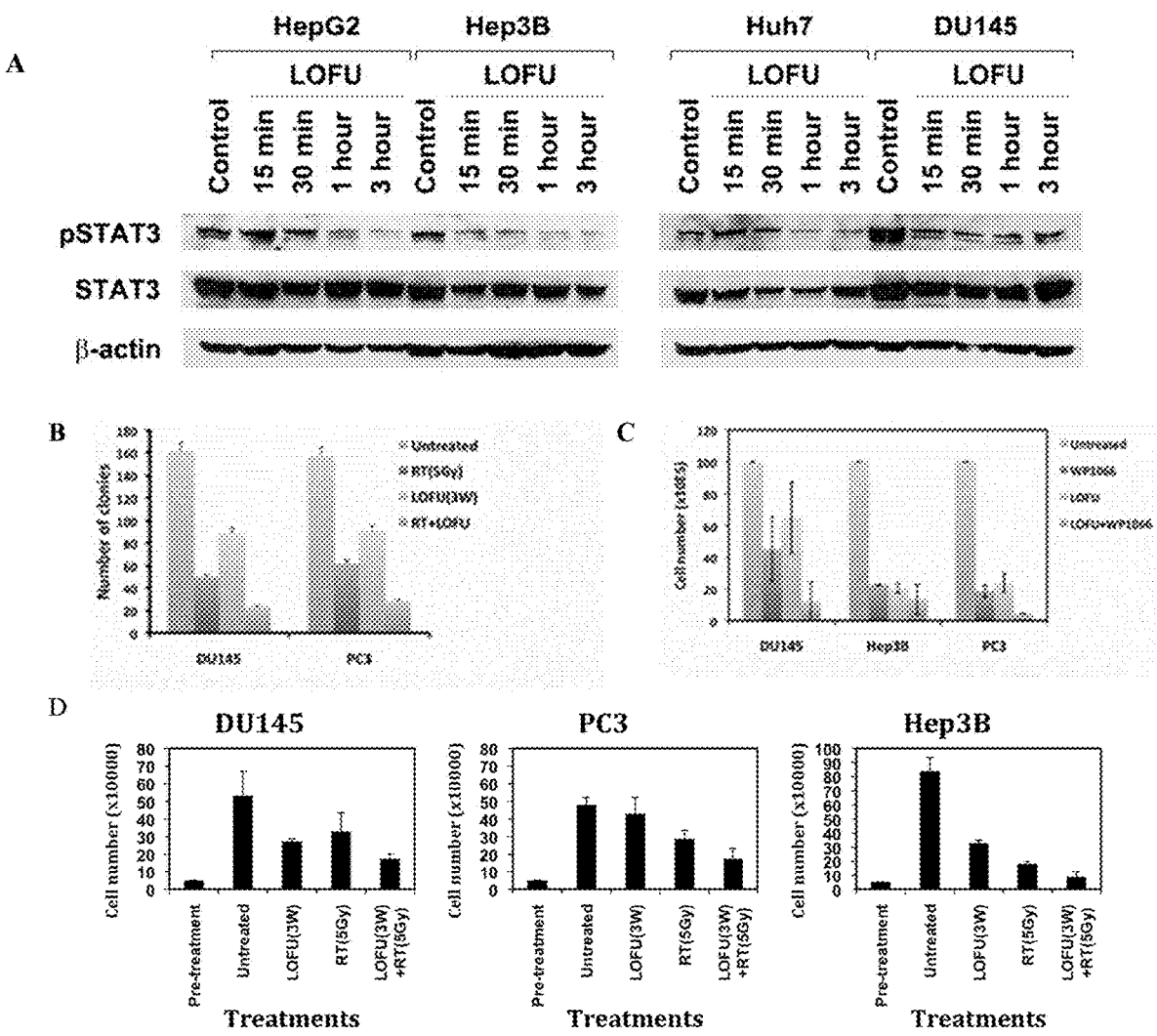

FIG. 5A-5B. FUS treatment of melanoma tumors potentiate dendritic cell-mediated priming of CD4+ T cells: 5A. CD11c+splenic dendritic cells were purified from C57Bl/6 mice and co-cultured with responder naive CD4+ T cells isolated from OT-II mice. B16-F1-OVA melanoma tumor lysates were prepared from untreated or LOFU treated tumor-bearing mice and added to the respective cultures to drive dendritic cell mediated T cell stimulation. In separate samples exogenous OVA323-339 peptide was also added along with tumor lysates. Supernatants were collected after 24 hours, and IL-2 production was assessed by ELISA. The results are shown as mean±SEM from 4 independent experiments and analyzed with one-way ANOVA followed by a Tukey posttest (*$P<0.05$; *** $P<0.001$; n.s., not significant). 5B. B16-F1 melanoma tumors were left untreated or treated with LOFU. Tumor DLN were isolated and depleted of T cells. DLN cells were then co-cultured with naive Tyrp1 CD4+ T cells and stimulated with B16 melanoma tumor lysates obtained from in vitro cultures. Supernatants were collected 24 hours later and analyzed for IL-2 levels by ELISA. The data is shown as mean±SEM from 3 independent experiments. Differences between cytokine production in cultures using DLN cells from untreated or LOFU-treated mice were analyzed using a 2-tailed t test (*$P<0.05$).

FIG. 6A-6D LOFU inhibits the constitutive STAT3 activation in human hepatocellular carcinoma cell lines. Three human HCC cell lines, HepG2, Hep3B and Huh7 were found to have constitutive activation of STAT3 and LOFU significantly inhibited STAT3 activation in all three HCC cell lines (6A). The response to LOFU in these three cell lines displayed different patterns with Hep3B responding in as early as 15 minutes and HepG2 and Huh7 at 1 hour. This result further proved the effect of LOFU on STAT3 deactivation and provided the evidence for using LOFU in HCCs in addition to prostate cancers. Since LOFU has been shown to downregulate STAT3 activity which is responsible for radioresistance of many cancer cells, LOFU may serve as a radiosensitizer for cancer radiation therapy. Cancer cells were first treated with LOFU and then exposed to radiation (5Gy) 1 hour later. Cells were incubated for 96 hours and the total number of cells was counted by trypan blue. Additionally, clonogenic assay was also performed and the number of colonies was counted 10 days after treatment. Combined LOFU and radiation had lowered number of cells (6B) and colonies (6D) as compared with LOFU and radiation alone. In addition, adding a STAT3 inhibitor, WP1066, prior LOFU treatment had yielded superior effect on inducing cell death (6C). LOFU and WP1066 showed similar effect on cell growth, which was consistent with the results on STAT3 inhibition by both agents.

FIG. 7A-7D. FUS followed by hypofractionated IGRT results in T-cell mediated long term primary tumor control and reduced distal metastases: 7A C57B1/6 mice with 50 mm$^3$ subcutaneous dorsal right hind limb tumors were separated into one of four treatment groups: untreated, LOFU, hypofractionated IGRT, or LOGU+IGRT and tumor growth monitored for 62 days or until primary tumor grew beyond 300 mm$^3$. Graph shows mean±SEM of tumor volume from one of two representative experiments (3-5 mice per group). Data were analyzed with either one-way ANOVA followed by a Bonferroni correction post test (before day 29) or by 2-tailed student t test (after day 29). Significant differences (defined as P<0.05) between untreated or LOFU-treated mice and IGRT or LOFU+IGRT treated mice occurred after day 25, and between IGRT treated and LOFU+IGRT treated mice after day 35. Individual graphs showing the distribution of tumor size at specific days are also shown in 7B. Similar experiments as the ones described in 7A were performed in BALB/c nude mice. No significant differences were observed among the different groups at any time point. 7C. C57B1/6 mice were monitored for primary tumor progression/recurrence, defined as either recurrence reaching a volume of 150 mm$^3$ or the development of local metastasis to the popliteal or inguinal lymph nodes. In addition, animals that died spontaneously were scored as having recurrence or progression of disease. Recurrence free survival data was analyzed using the Mantel-Cox test. 7D. Lungs were harvested from animals that either died spontaneously, required euthanasia due to overwhelming tumor burden, or were sacrificed at the end of a two month long experiment. Lung metastasis were then measured. Lungs with nodules that fuse into plaques, or exceed 250 were deemed too numerous to count and assigned a maximal value of 250. A representative specimen is shown for each treatment group. The results are shown as mean±SEM, with n=3-5 mice per group, analyzed with a Kruskal-Wallis test, followed by Dunn's posttest. * P<0.05.

Figures 8A, 8B, 8C, 8D:
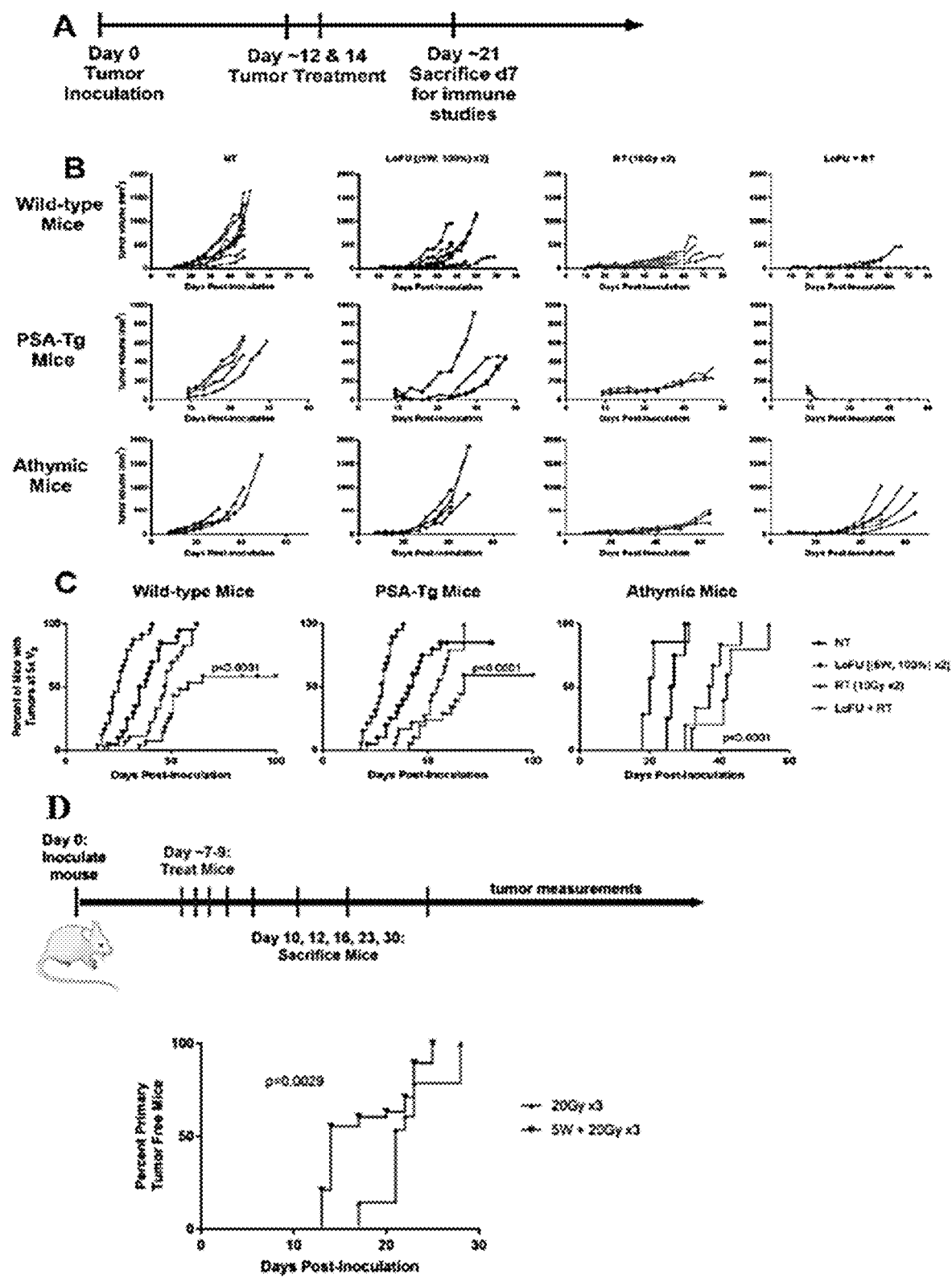
Figures 9A, 9B, 9C, 9D, 9E, 9F, 9G:
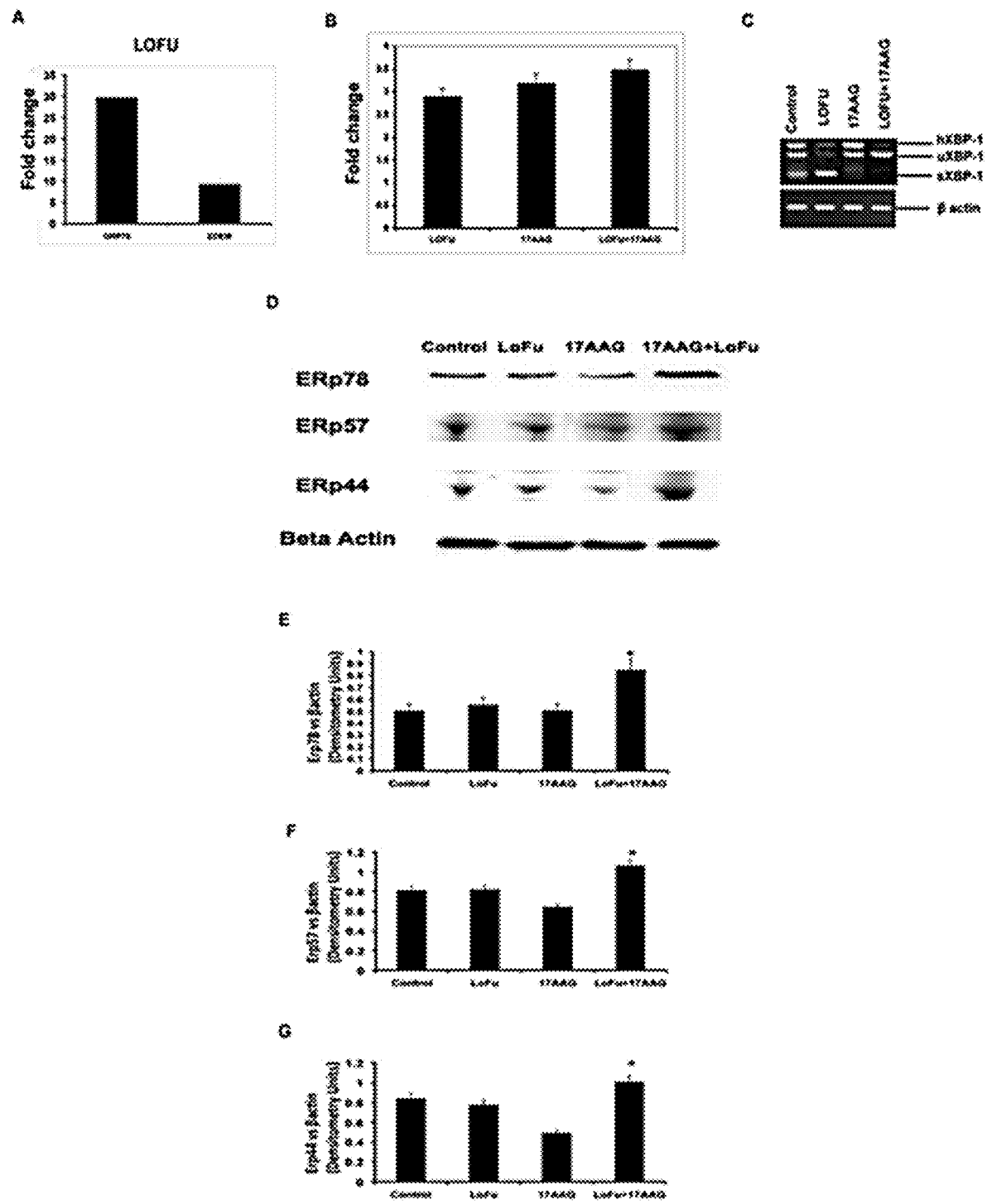

FIG. 8A-8D: LOFU and RT treatment of murine prostate cancer and breast cancer models. Two treatments with LOFU (5 W, 100%) and/or radiation (10Gy) were performed on two days with a 24 hour gap between (8A). Due to the higher intensity of this LOFU treatment, there was one-day gap between the treatments to allow for healing of the wound prior to a second treatment. For this tumor, the radiation dose of 10Gy×2 was able to significantly retard tumor growth without complete cure (8B top row). The median time for the tumor to reach 5 times the initial volume (V0) was 47 days, compared to 25 days for non-treated mice. The addition of LOFU prior to radiotherapy resulted in primary tumor cure of about 46.4% of the mice treated (8B top & 8C left). The addition of LOFU did result in some minor skin burns covering the majority of the tumor surface. These burns healed naturally within 1-2 weeks of treatment. In a wild-type mouse, the ability to mount an immune response against a foreign antigen, such as human PSA in this case, did not mimic the case of human prostate cancer, which while low on the mutation load, was full of self-antigens. PSA-Tg transgenic mouse, a model that best mimicked the human condition of prostate cancer, subjected to combination therapy with LOFU and RT had shown an reduction of 57.1 of primary tumors (8B middle row & C(center). These results indicated that either combination therapy with LOFU and RT was able to overcome tolerance to PSA or able to generate enough neo-antigens to make the tolerance to PSA irrelevant. To confirm the efficacy of LOFU and TR was mediated through T cells, the same experiment was conducted in athymic nude mice. While radiation did result in tumor growth retardation of the primary tumor, the addition of LOFU did not offer any benefit (8B bottom row & C right). These results indicate that T cells were required to cure the primary tumor using LOFU and RT combination. A triple negative breast cancer murine model, 4T1, was used to determine the efficacy of LOFU and RT combinatorial treatment. LOFU (5 W, 50% duty factor) and/or 20Gy of radiation was performed on 3 consecutive days about 7 days after tumor inoculation with 2×10$^5$cells(FIG. 8D). While both radiation alone as well as LOFU and radiation combination therapy resulted in primary tumor cure, combination therapy significantly accelerated the time to primary tumor cure by a median time of one week.

FIG. 9A-9G: LOFU induces UPR. 9A. LOFU increases the expression of Bip/Grp78 and EDEM mRNAs. Real Time-PCR analysis of RNA isolated from LOFU-treated Rill tumors showed 29.73+0.56 fold increase in Bip/Grp78 and 9.27+1.18 fold increase in EDEM mRNA level compared to untreated control. 9B. LOFU increases the expression of IRE1α mRNA by 2.8+0.4 folds. Real Time-PCR analysis demonstrates that LOFU induced increase in the IRE1α expression did not alter with the 17AAG treatment. 9C. LOFU induced the splicing of XBP1 mRNA. 17AAG treatment inhibits the splicing of XBP1. XBPIs, XBP1h, and XBP1u denote the spliced, hybrid, and un-spliced forms of XBP1, respectively. 9D-G. LOFU+17AAG combination therapy prolongs ER stress in RM1 tumor cells. Western blot and bar chart showing that the expression of ERP78 (9D & 9E), ERP57 (9D & 9F), and ERp44 (9D & 9G) proteins was induced in combination treatment group.

FIG. 10A-10E: LOFU+17AAG activates pro-apoptotic pathways of UPR and induces apoptosis in tumor cells. 10A & 10B. Western blot of pPERK (10A) and peIF2a (10B). LOFU+17AAG activates PERK by phosphorylation of PERK (pPERK), which further induces the phosphorylation of eIF2a phosphorylation (peIF2a). 10C. Real Time-PCR analysis of CHOP mRNA. There was a 25+1.3-fold increase in CHOP transcript in LOFU+17AAG treated group, compared to control. 10D. Real Time-PCR array of RNA isolated from LOFU+17AAGtreated tumors. Heat map analysis showed that LOFU+17AAG treatment group increased the transcript level of apoptotic genes several folds compared to untreated control or LOFU groups. 10E. TUNEL staining. Immunohistochemical staining showed predominantly tunel positive cells in LOFU+17AAG treatment group, compared to control or LOFU group. Note that 17AAG alone also induced apoptosis in tumor tissue that was augmented by LOFU.

Figures 11A, 11B, 11C:
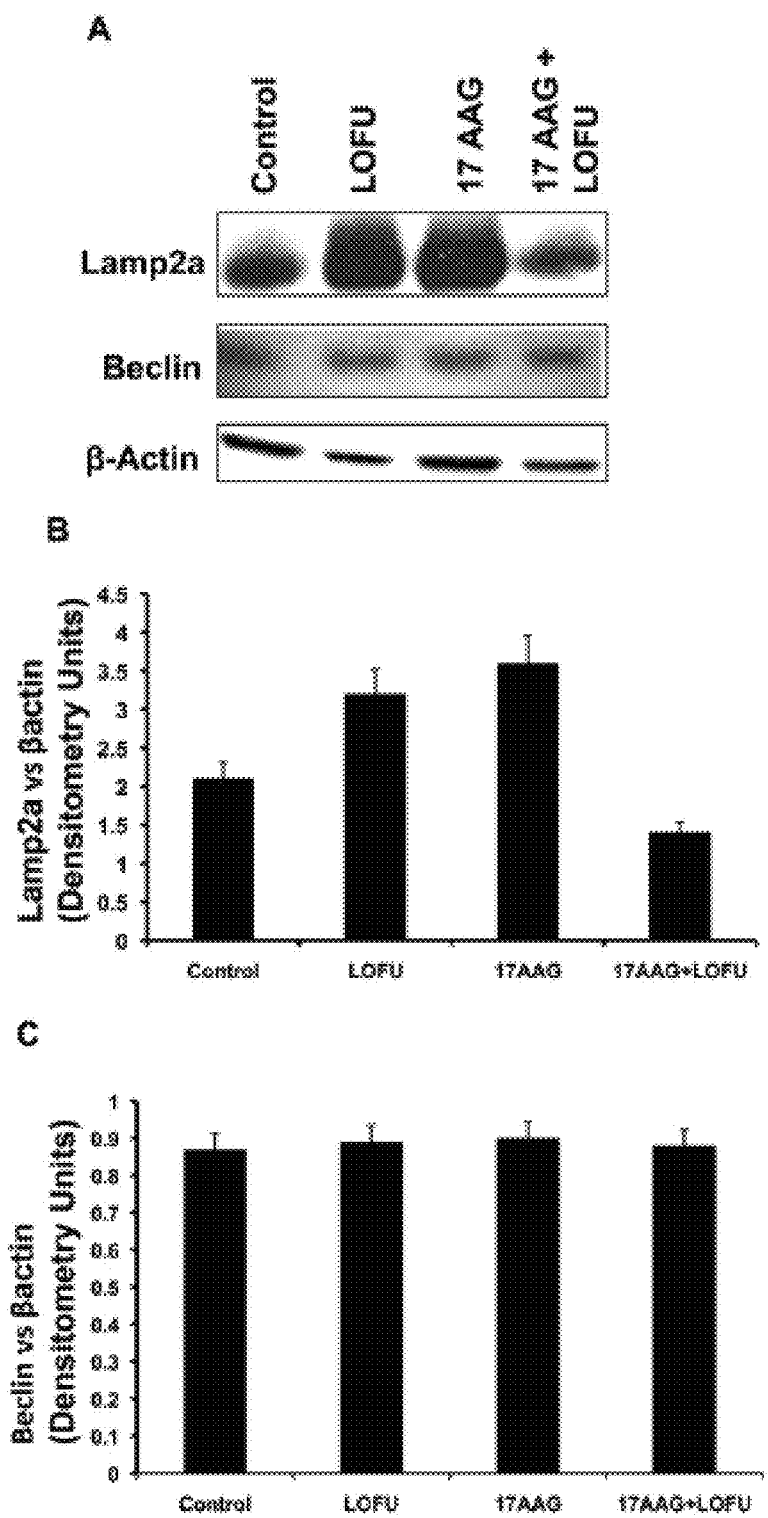

FIG. 11A-11C: LOFU+17AAG treatment inhibits Chaperone Mediated Autophagy (CMA) in RM1 tumor cells. (11A & 11B) Immunoblot analysis showed several fold down-regulation of SMA marker LAMP2a expression level in combination treatment group. Treatment with either LOFU or 17AAG upregulates the LAMP2a expression level. (11A & 11C) Combination treatment of LOFU and 17AAG did not alter the expression level of Beclin, a macroautophagy marker.

Figure 12A:
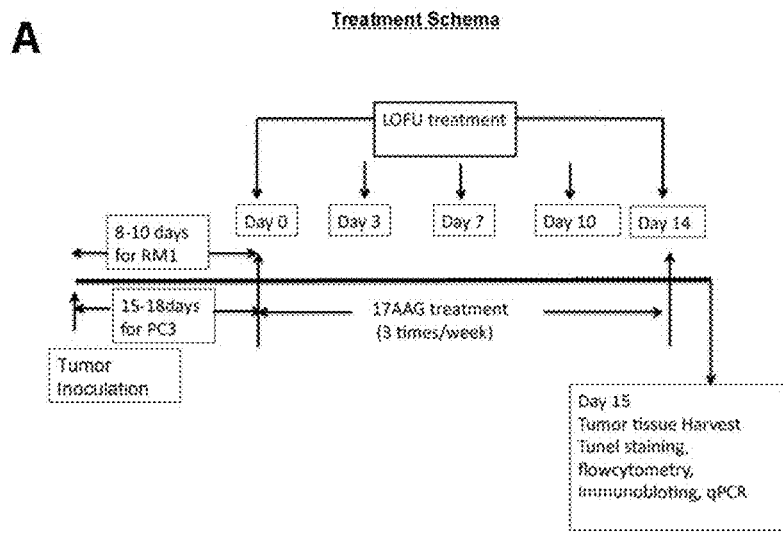
Figure 12B:
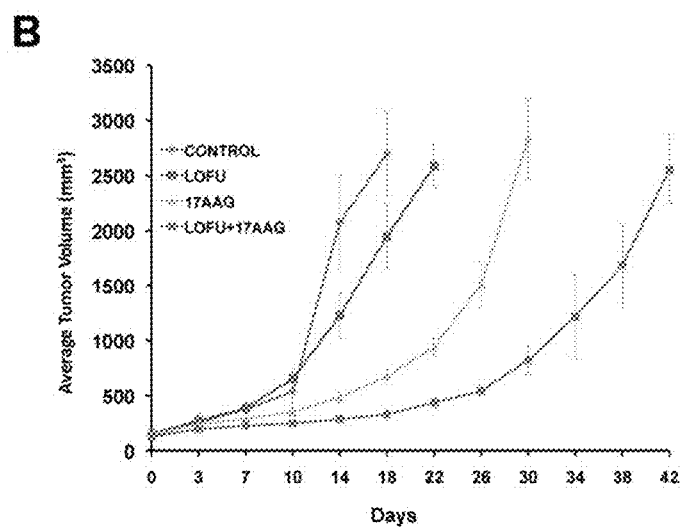
Figure 12C:
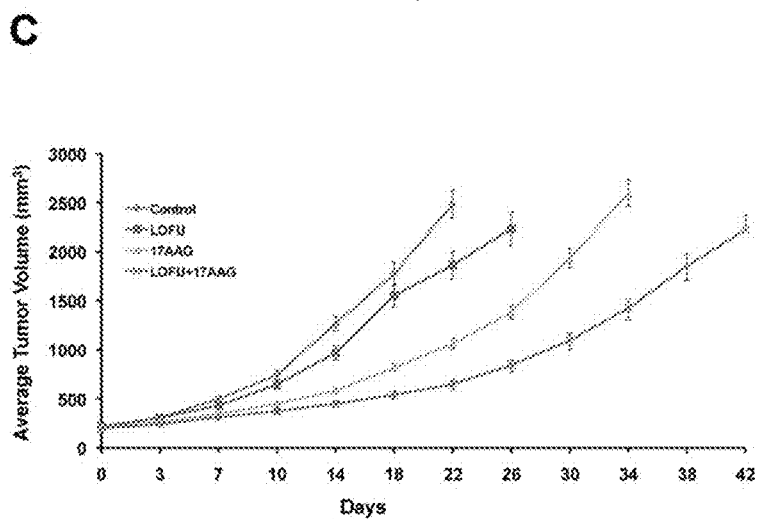
Figures 13A, 13B, 13C, 13D, 13E, 13F:
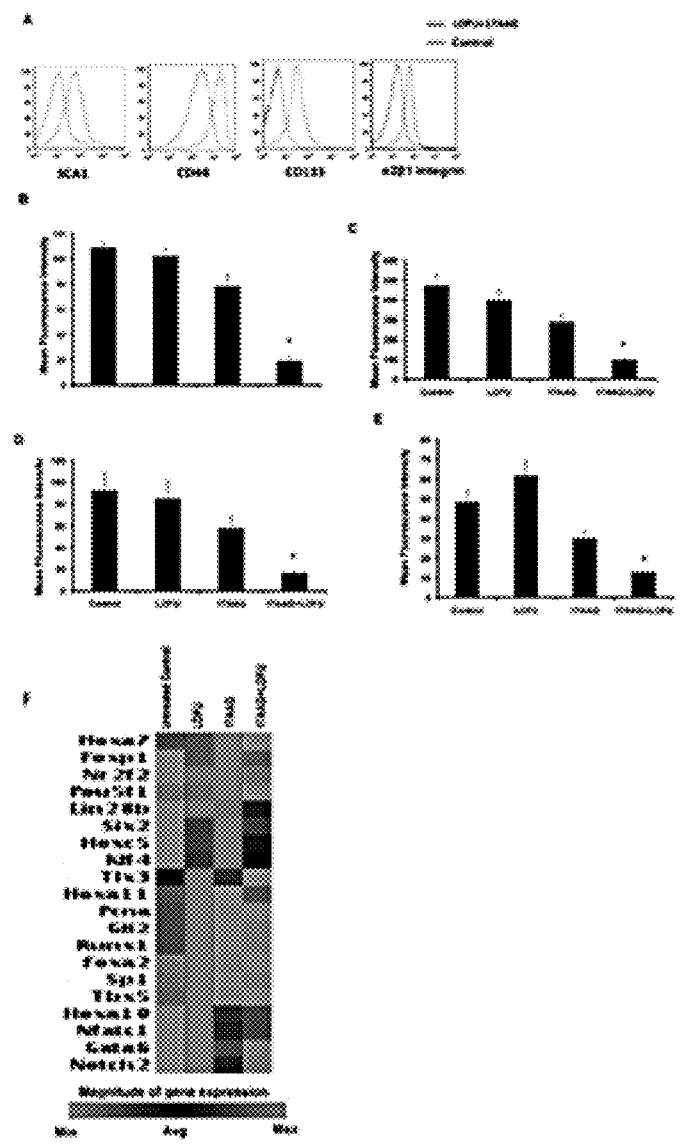

FIG. 12A-12C: Tumor growth retardation of murine and human prostate tumors after LOFU+17AAG treatment. 12A. Treatment schema. Palpable tumors were treated with LOFU every 3-4 days for five fractions administered over two weeks. Animals received 17AAG three times a week during this time. Tumors were harvested 24 hours after the last fraction of LOFU. 12B. RM1 tumor. In C57B16 mice, LOFU+17AAG combination treatment reduced RM1 tumor growth significantly (p<0.004), compared to controls. Note that either LOFU or 17AAG alone failed to control tumors significantly. LOFU sensitized the effects of a low dose (25 mg/kg of body weight) 17AAG. 12C. PC3 tumor. In BalbC nu/nu mice LOFU+17AAG combination treatment showed significant reduction in PC3 tumor growth (p<0.007).

FIG. 13A-13F: LOFU+17AAG treatment reduces the expression of prostate cancer stem cell markers in RM1 cells. Flow cytometry of isolated RM1 tumor cells showed significant decrease in SCA1 (13A & 13B), CD44 (13A & 13C), CD133 (13A & 13D), and a2131 integrin (13A & 13E) cell surface expression on RM1 tumor cells after LOFU+17AAG treatment. (13F) qRT-PCR array followed by heat map analysis showed that LOFU+17AAG combination treatment group down-regulates the mRNA levels of stem cell transcription factors.

FIG. 14A-14E: Pretreatment with LOFU, followed by HIFU induced tumor-specific T cell response. Pretreatment with non-ablative LOFU would enable the tumor cells to process misfolded proteins and subsequent treatment with HIFU, a day later, would allow the release of HSP-peptide complexes from dying tumor cells for DC uptake and induction of T cell immunity. Palpable OVA-expressing RM1-OT tumors were treated sequentially with LOFU, followed by HIFU, one day apart and animals were sacrificed on days 3, 7 and 14 post-LOFU treatment. While, no tumor-specific T cell response was detected with one cycle of LOFU and HIFU treatment, there was a modest increase in the total number of IFN-γ producing cells (stimulated by PMA and Ionomycin) on day 3 ($110\pm5/2.5\times10^5$ cells LOFU and HIFU versus $66\pm16/2.5\times105$ cells untreated, p<0.05, 14A), indicating that LOFU and HIFU treatment may tip the immune response towards a Th1 phenotype. However, the number of IFN-γ-secreting cells decreased to pre-treatment levels in days 7 and 14, with no statistical difference amongst various. Therefore, repeated treatment of tumors with LOFU and HIFU would facilitate release of HSP and tumor antigens for periodic immunization, simulating a vaccination schedule for the induction of tumor-specific immune response. Palpable RM1-OT tumors were treated three times with weekly cycles of sequential LOFU and HIFU administered one day apart and animals were sacrificed one week after the last HIFU treatment. Frequency of tumor-specific T cells in splenocytes was analyzed by IFN-γ ELISPOT assay and cytotoxic functions of these tumor reactive T cells were detected by CD107a mobilization assay. When splenocytes from mice treated with LOFU and HIFU were co-cultured with irradiated RM1-OT cells, there was an increase in the number of IFN-γ-secreting RM1-OT reactive T cells ($432\pm65$ cells per $2.5\times10^5$ splenocytes after LOFU+HIFU, versus $15+6$ cells per $2.5\times10^5$ splenocytes after HIFU alone; 14B). The frequency of tumor-specific IFN-γ releasing T cells in LOFU and HIFU-treated mice was 0.17+0.03%. These tumor reactive splenocytes were also found to specifically recognize both OVA-derived MHC class I restricted peptide, OVA257-264 ($149\pm28$ cells per $2.5\times10^5$ total splenocytes) and MHC class II restricted peptide, OVA323-339 ($132\pm32$ cells per $2.5\times10^5$ total splenocytes) when co-cultured with these peptides. In contrast, no significant immune response was detected in mice treated with either LOFU alone or HIFU alone ($15\pm6$ cells per $2.5\times10^5$ total splenocytes in both groups). These results indicate that LOFU and HIFU combination therapy can induce both CD4 and CD8 T cell response to surrogate cytoplasmic tumor antigen, OVA. Although HIFU treatment alone induced cell death and release of intra-tumoral HSPs, it failed to induce significant anti-tumoral cellular immunity. Tumor-specific cytotoxic T lymphocytes (CTL) were assessed by the CD107a mobilization assay, which measures the presence of cell surface CD107a in splenocytes following culture with irradiated RM1-OT cells. CD107a is a membrane protein of Perforin/Granzyme B vesicle that becomes transiently mobilized to the cell surface during the cytotoxic degranulation process by CTLs. Although, CTLs were present in all treatment groups, tumor-specific CD107a+ T cells were highest in LOFU and HIFU-treated mice ($27.88\pm4.80\%$ in LOFU and HIFU vs. $7.5+1.2\%$ in untreated, p<0.05; 14C). The percentage of CD8+ T cells that were reactive to the surrogate tumor antigen, . OVA, were quantified by H-2b/OVA257-264 tetramer staining (14D). While, untreated or single treatment cohorts had negligible OVA-reactive CD8 T cells, there was an increase in these cells after LOFU and HIFU treatment (0.12% LOFU+HIFU vs<0.01% untreated), which further confirmed the presence of tumor specific T cells in vivo. Finally, to investigate whether pretreatment with non-ablative LOFU augments the therapeutic effects of HIFU, the time intervals for HIFU exposure were kept the same between treatment groups in mice with tumors. The tumor size amongst various groups was not significantly different after 1 cycle of ultrasound therapy, but the growth retardation was seen after 2 cycles (14E, lower panel). As expected LOFU treatment alone did not alter the tumor growth rate, as compared to untreated controls (p>0.05). HIFU alone significantly suppressed tumor growth compared to LOFU and untreated cohorts (p<0.05). Pretreatment with LOFU significantly enhanced the tumoricidal effects of HIFU therapy (LOFU and HIFU vs. HIFU, p<0.01; LOFU and HIFU vs LOFU or No treatment (NT), p<0.001) as also shown by relative mouse pictures (14E, upper panel).

Figures 15A, 15B, 15C, 15D, 15E, 15F:
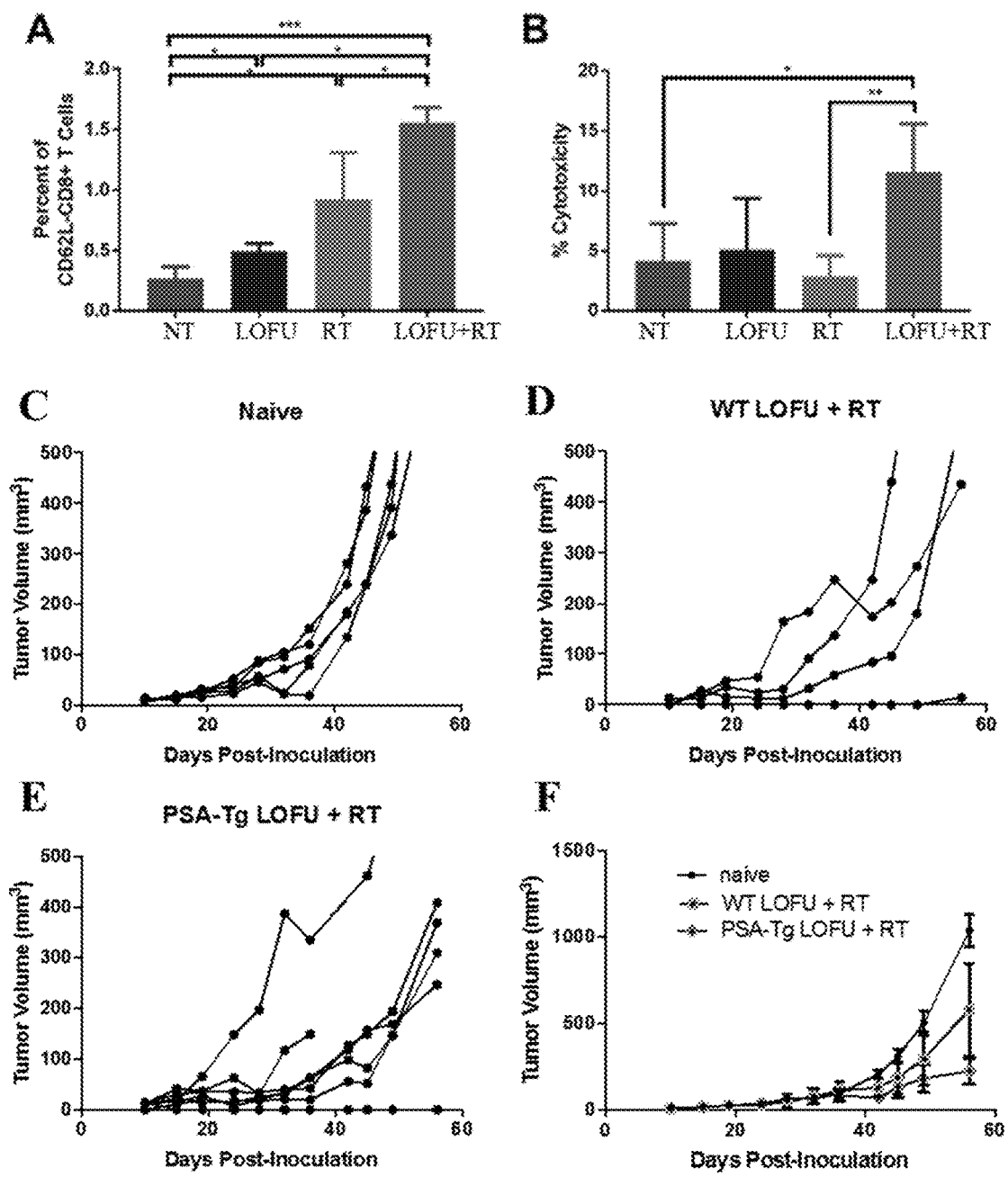

FIG. 15A-15F: LOFU and RT combinatorial treatment augments anti-tumoral cytotoxic T cell immunity and immune memory in a tumor rechallenge murine model. To determine the impact of combination therapy on CD8+ T cell responses, tumor antigen specific T cells were analyzed after treatments using a PSA-specific MHC Class I pentamer. There was an increase in the PSA-specific, activated, CD62L-CD8+ T cells across all the treatment groups, with LOFU+RT having the highest percentage of CD62L-/pentamer+CD8 T cells ($1.557\pm0.127\%$) compared to LOFU alone ($0.497\pm0.064\%$) and RT alone ($0.923\pm0.387\%$) groups (FIG. 15A). An LDH release assay indicative of cell death also confirmed that splenocytes from PSA-transgenic mice treated with the combination therapy increase cell death in tumor (NT: $4.186\pm3.1\%$, LOFU: $5.1\pm4.3\%$, RT: $2.91\pm1.7\%$, LOFU+RT: $11.613\pm3.98\%$; FIG. 15B). To determine if LOFU and RT combination treatment resulted in immunological memory, mice that were cured from primary tumor after LOFU+RT therapy were rechallenged with TPSA23 cells on the contralateral flank and measured the tumor growth profile up to 60 days post-inoculation. FIGS. 15C, 15D and 15E depicted the tumor growth in individual mice in each treatment group. At day 45 post-inoculation 7 out of 8 PSA-transgenic mice showed significant growth delay (naive: 307.6 mm$^3$, WT: 184.8 mm$^3$, PSA: 128.6 mm$^3$, p=0.10) and only 1 mouse showed complete lack of tumor memory. By day 56 post-inoculation, 2 out of 8 PSA-transgenic mice had complete tumor growth inhibition (FIG. 15E). Re-challenge response in WT mice (FIG. 15D) was different, at day 43 post-inoculation, only 1 out of 4 showed tumor growth inhibition and persisted in its tumor inhibition response until the end of the experiment. At day 56, the WT mice cured of primary tumor by LOFU and RT combination had a tumor growth delay of 52% and the PSA-transgenic mice cured of primary tumor by LOFU+RT combination had a tumor growth delay of 74% compared to naïve mice (FIG. 15F) indicative of immune memory generated by LOFU+RT treatment of the previously cured tumor. While both C57/BL6 (WT) and PSA-transgenic mice (C57/BL6 background) primary tumor-cured groups showed tumor growth retardation after rechallenge, only PSA-transgenic mice showed statistically significantly reduction in the tumor volume ($p=0.0043$, Mann-Whitney U) compared to the naïve group. While there was no statistically significant difference between the rechallenge tumor volume in wild-type rechallenged mice and naïve or PSA-transgenic mice, 1 out of 4 mice demonstrated no immunological memory, while 3 out of 4 mice had a statistically significant growth delay compared to non-treated ($p=0.04$). These experiments indicate that combination treatment of LOFU and RT not only resulted in primary tumor cure but also enhanced immunological memory, which resulted in significant inhibition of the secondary tumor growth.

Figures 16A, 16B, 16C:
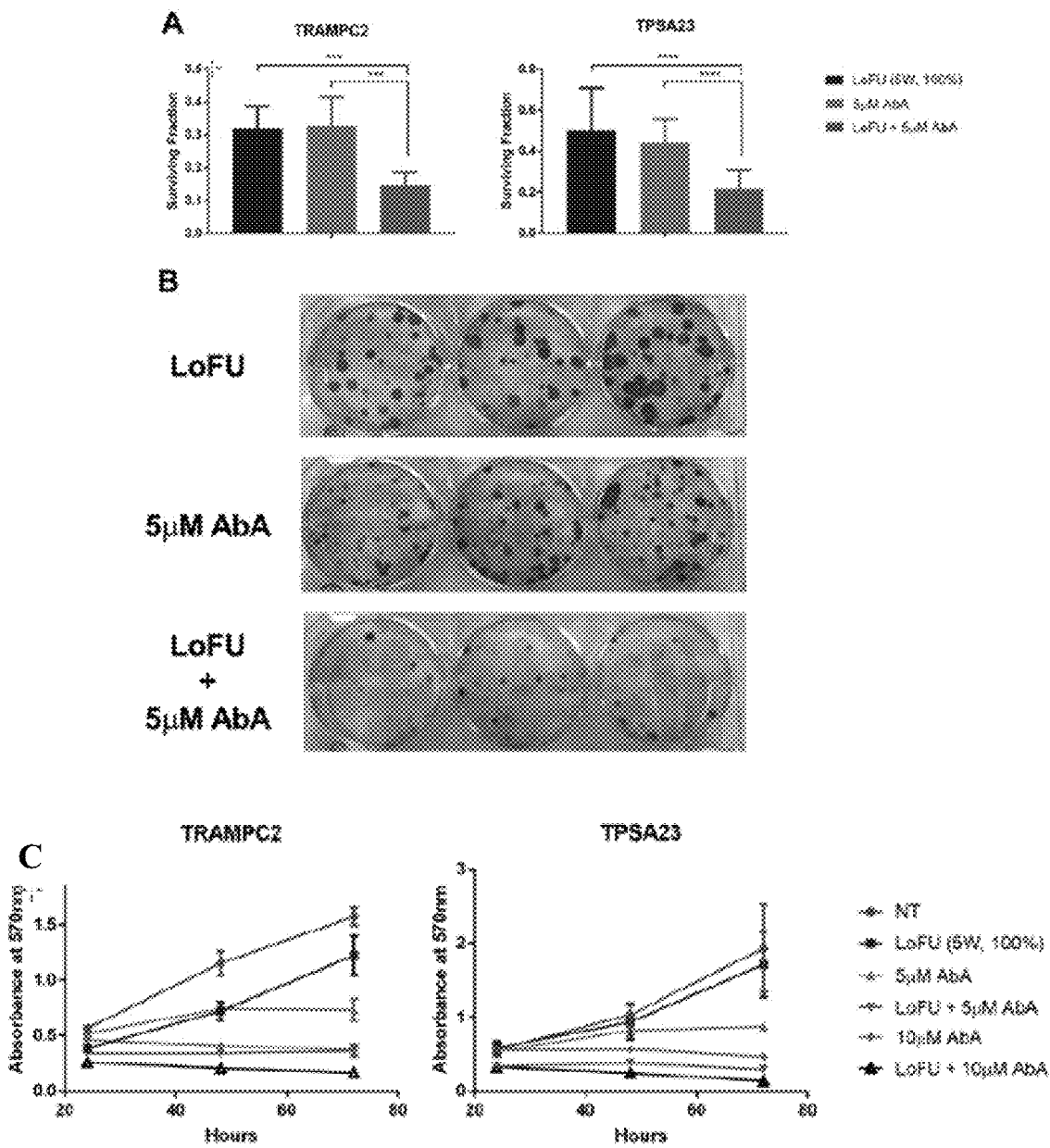
Figure 16D:
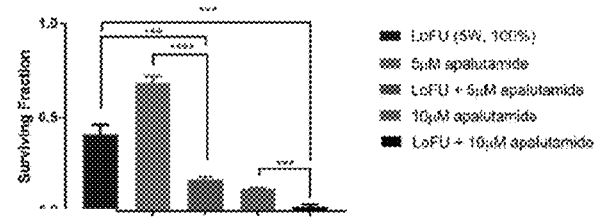
Figure 16E:
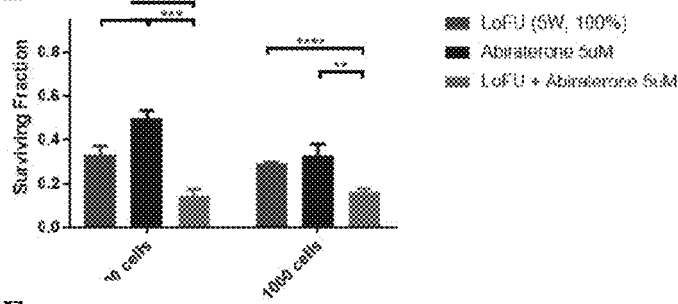
Figure 16F:
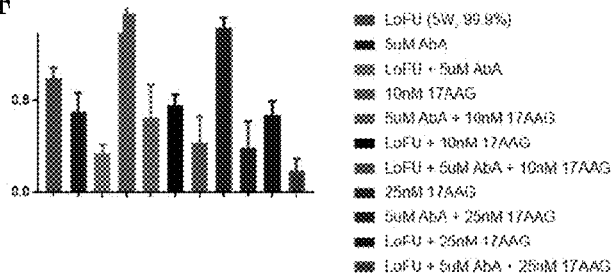
Figure 16G:
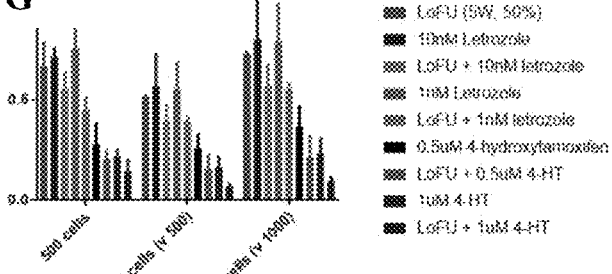
Figure 16H:
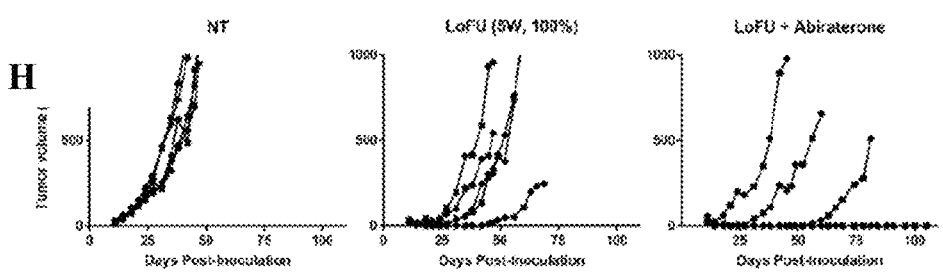

FIG. 16A-16H: Hormone based chemotherapy augmentation by LOFU. Clonogenicity is important in the context of cancer progression, especially when considering the formation of metastases. Clonogenicity refers to the ability of a single cell to produce 8 successful generations. A clonogenic assay was performed in conjunction with 5 µM of abiraterone (AbA), an antiandrogen, treatment. No significant difference was noted in the surviving fraction between LOFU alone and abiraterone alone (16A). However, as indicated in the representative picture below, colonies formed under abiraterone treatment were, on average, smaller than those formed with LoFU treatment (16B). Combination treatment led to a significant reduction in the surviving fraction in both TRAMPC2 and TPSA23 cell lines compared to the individual treatments. Proliferation assay of abiraterone alone or in combination with LOFU on TPSA23 and its parent cell line TRAMPC2 was conducted with crystal violet signal as the output of cellular proliferation. A lower dose of abiraterone (5 µM) significantly inhibited proliferation of the both cell lines (16C) beyond 48 hours of incubation compared to non-treated (TRAMPC2: $p=0.0003$; TPSA23: $p=0.04$; unpaired two-tailed T test). Higher dose of abiraterone (10 µM) eliminated the proliferation capacity of both cell lines. When LOFU was used in addition to 5 µM of abiraterone, the proliferation capacity was eliminated to similar extent as with 10 µM of abiraterone. The loss of proliferative capacity was statistically significant between LOFU and either dose of abiraterone when compared to the monotherapy ($p<0.005$, unpaired two-tailed T test). Apalutamide, an antagonist of the androgen receptor in combination with LOFU had a similar enhanced effect on the clonogenicity of TPSA23 tumor cells as abiraterone therapy. LOFU, in combination with a lower dose of apalutamide (5 µM) resulted in significantly fewer colonies than apalutamide or LOFU alone and was similar in efficacy to double the dose of apalutamide (16D). A higher dose of apalutamide (10 µM) resulted in significant reduction in clonogenicity, but the combination was still more effective. Similar results were also observed in murine prostate cancer (16E-16F) and human breast cancer cell lines (16G). Combination of LOFU, Aba, and 17AAG had synergistic effect on reduction of prostate cancer cells surviving the regiment. Letrozole and 4-hydroxytamoxifen (4-HT) both target estrogen receptors and used for breast cancer therapy. FIG. 16G entailed the survival fraction of MCF7 human breast cancer cell lines when treated either alone or in combination with LOFU, Letrozole, and 4-HT. Lastly, an in vivo murine model of TPSA23 were treated with LOFU (5 W, 100%) administered twice over three days. Abiraterone was given by daily oral gavage for 14 consecutive days (0.5 mg/mouse/day). The combination treatment resulted in significantly tumor growth retardation in 3 out of 5 of the mice and primary tumor cure in 40% of the mice treated (2 out of 5) (16H). On day 45 post inoculation, LoFU alone had a 66% tumor growth delay compared to non-treated and combination of LOFU and abiraterone resulted in a 100% tumor growth delay over either nontreated or LOFU alone.

Figure 17:
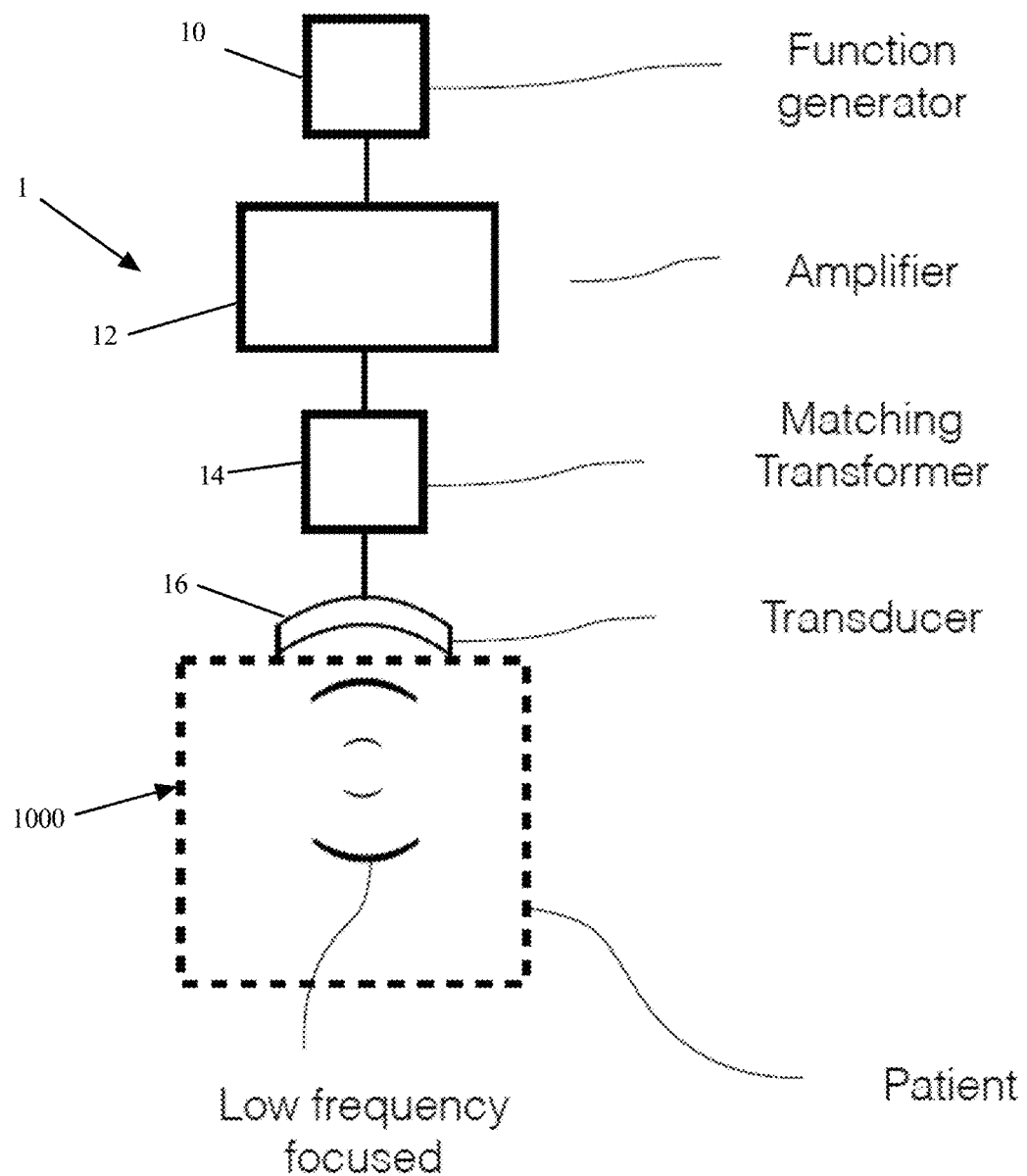

FIG. 17 is a block diagram of an APT device according to some embodiments of the present invention.

Figure 18:
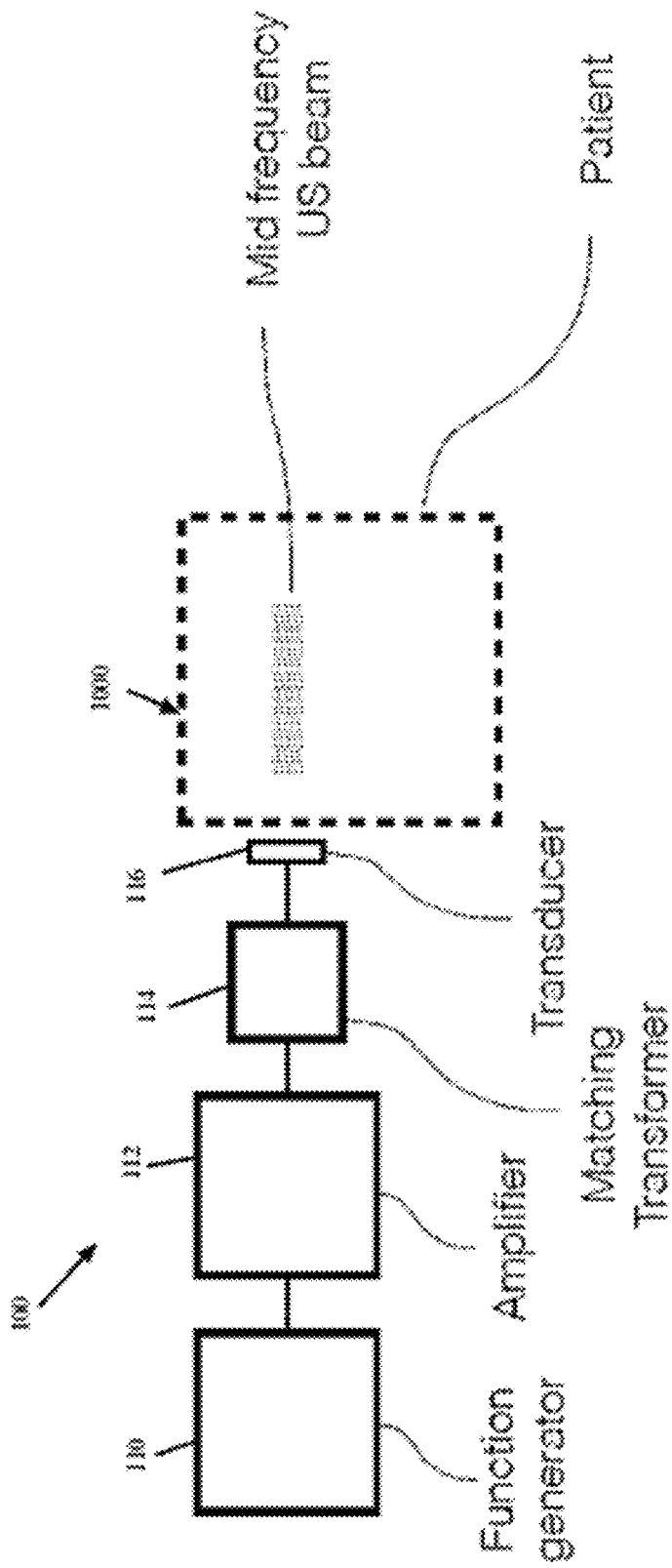

FIG. 18 is a block diagram of an APT device according to some embodiments of the present invention.

Figure 19:
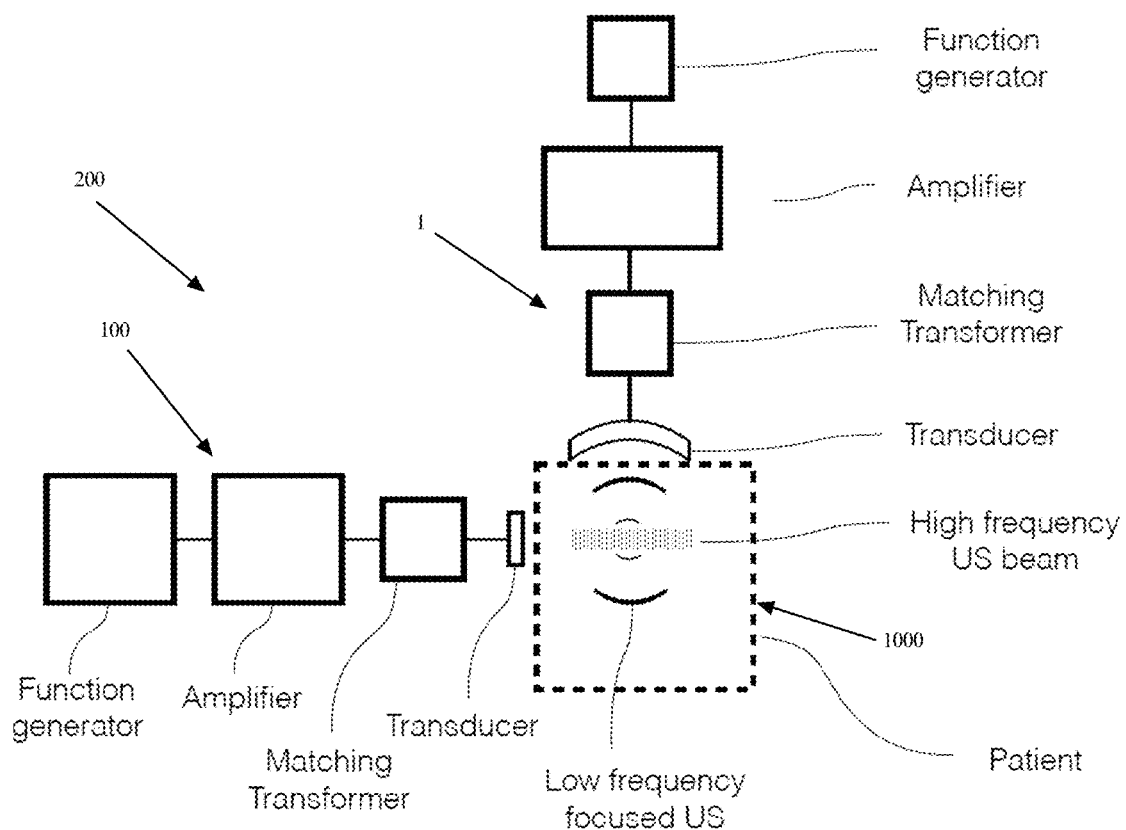

FIG. 19 is a block diagram of an APT device according to some embodiments of the present invention.

Figure 20:
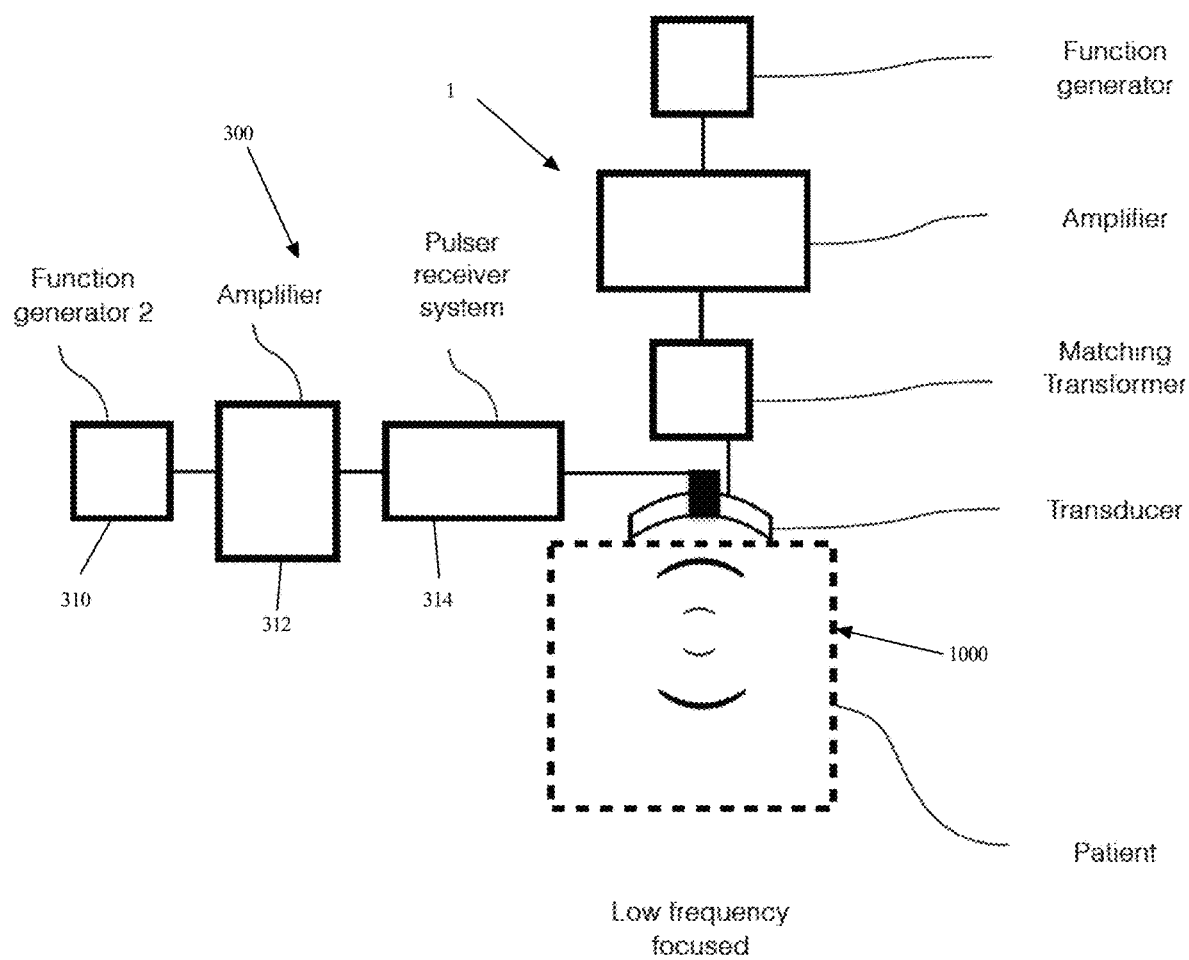
Figure 21:
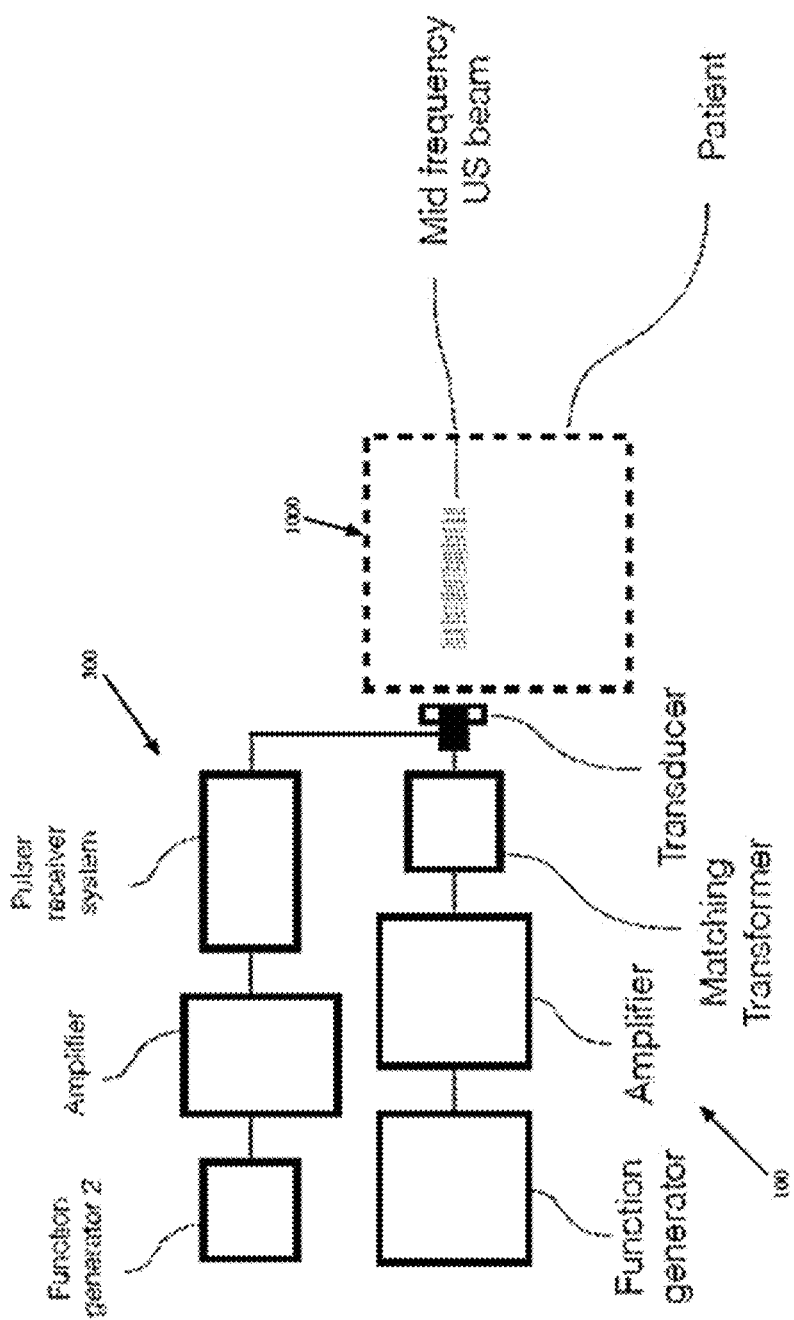
Figure 22:
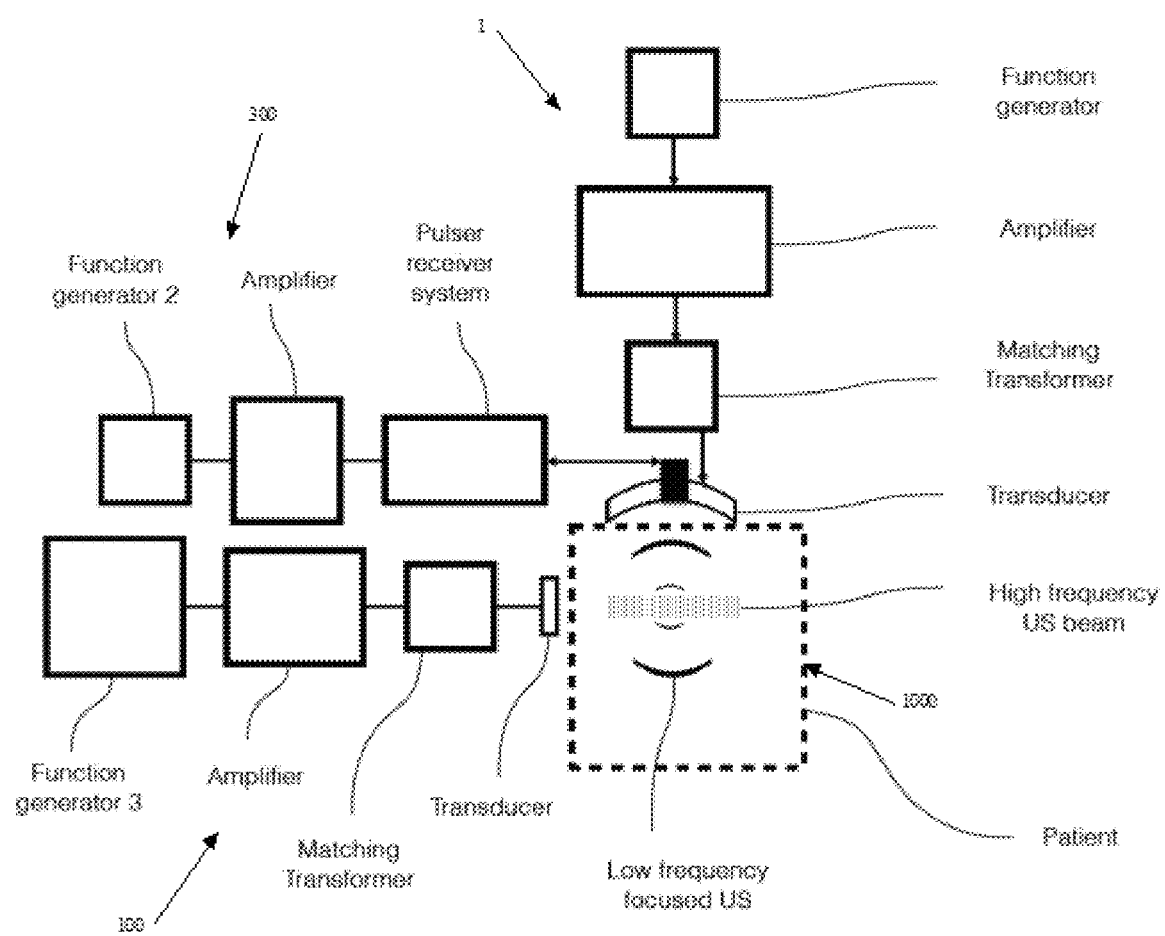

FIGS. 20, 21, and 22 are block diagrams of APT devices according to some embodiments of the present invention including an integrated ultrasound imaging device.

Figure 23:
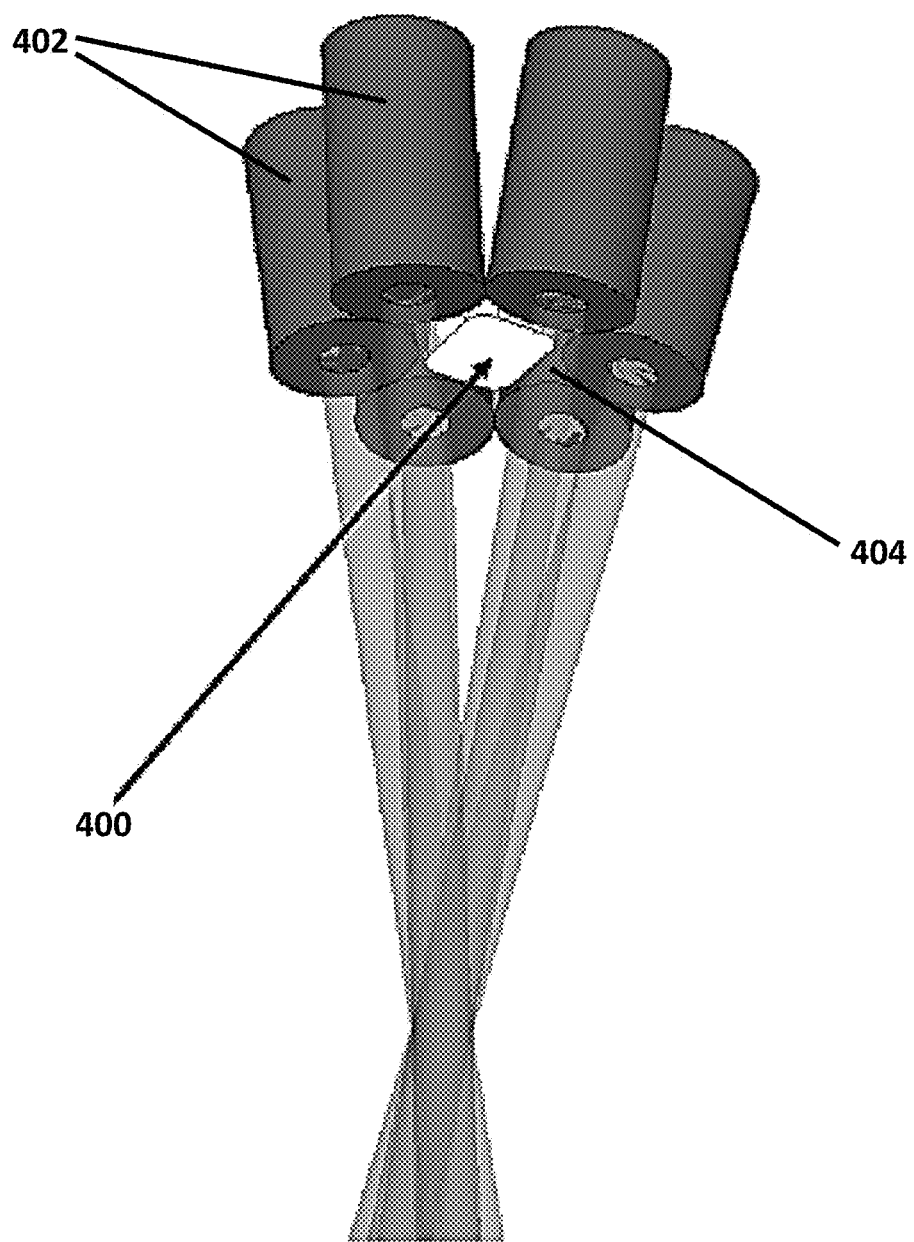

FIG. 23 is a perspective view of a transducer according to some embodiments of the present invention.

Figure 24:
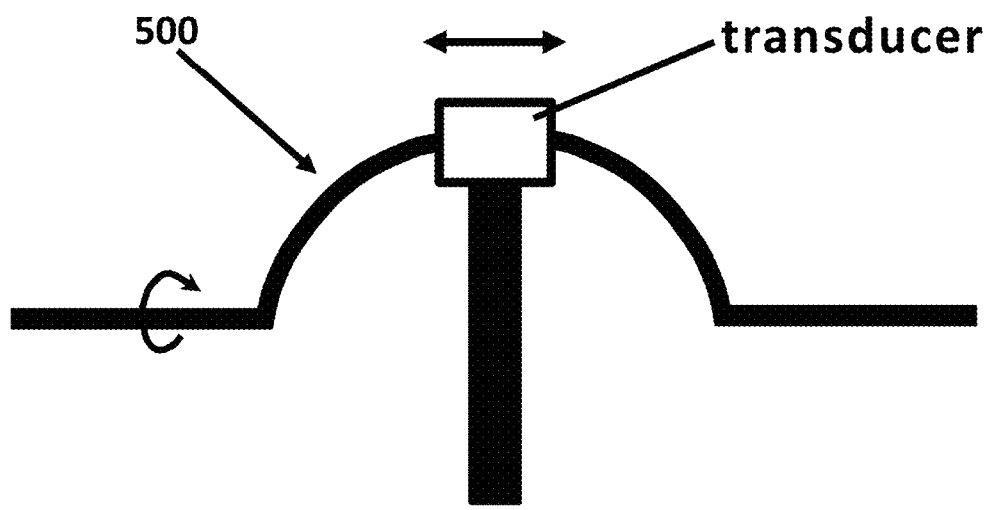

FIG. 24 illustrates a positioning apparatus according to some embodiments of the present invention.

Figure 25:
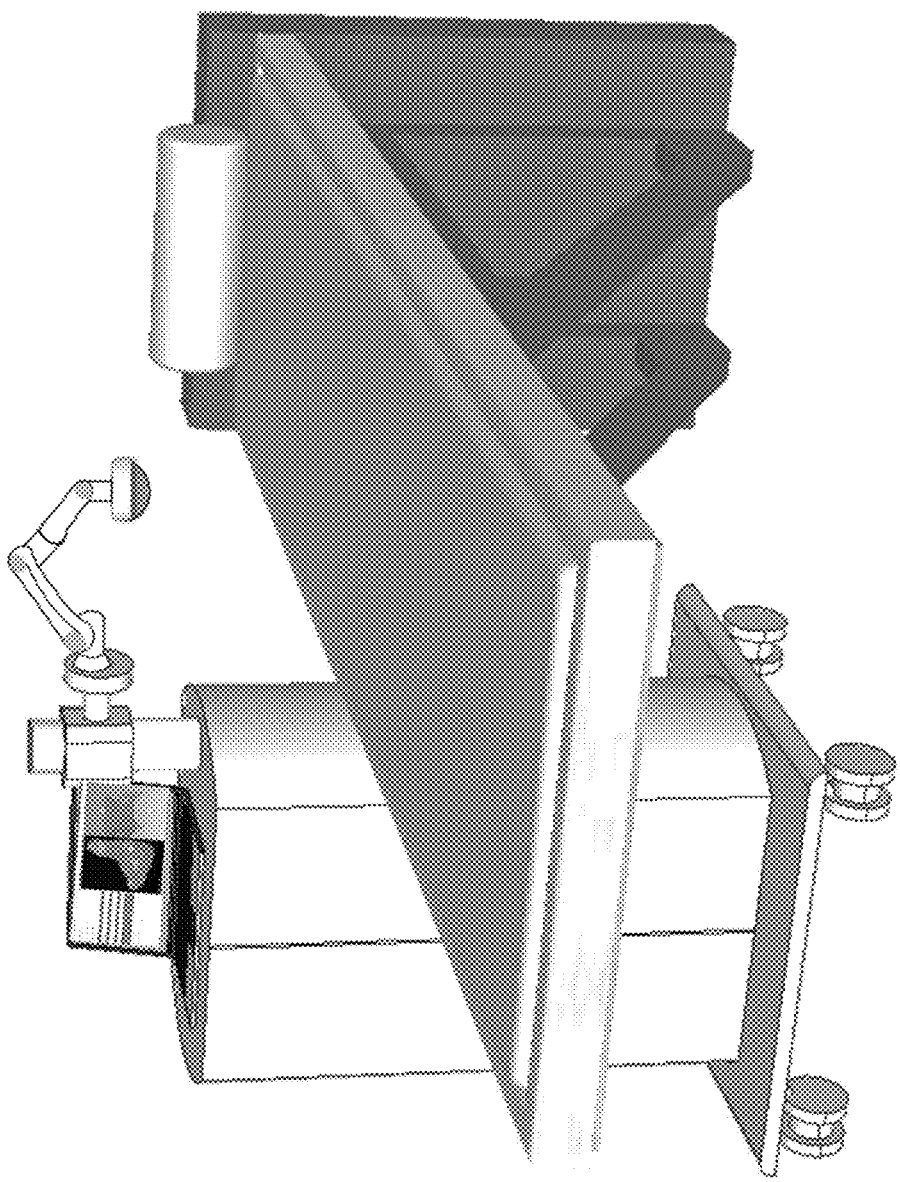

FIG. 25 shows an ultrasound transducer mounted on a robotic arm, in accordance with some embodiments.

Figure 26:
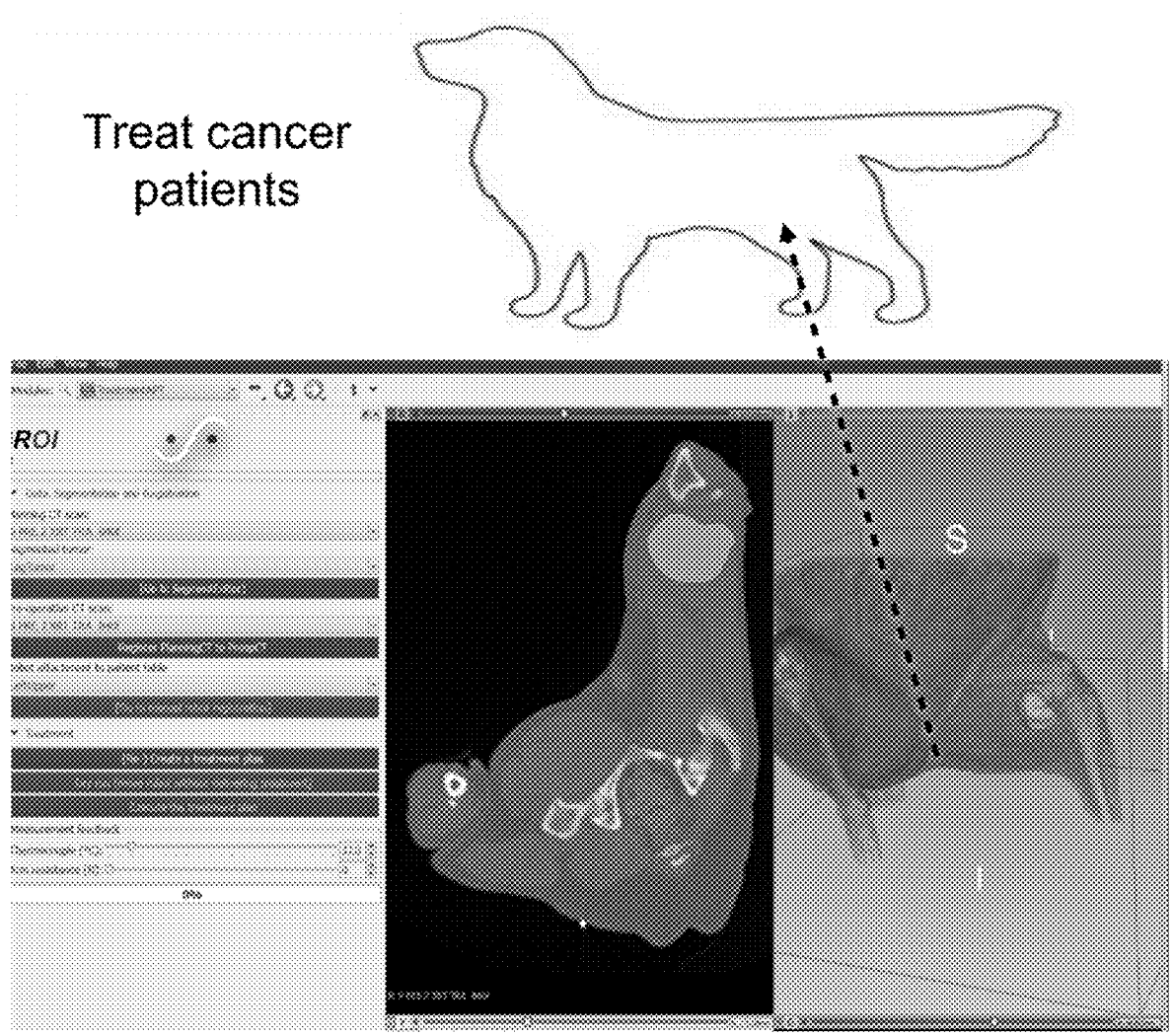

FIG. 26 illustrates a graphical user interface showing CT segmentation (images), in accordance with some embodiments.

Figure 27:
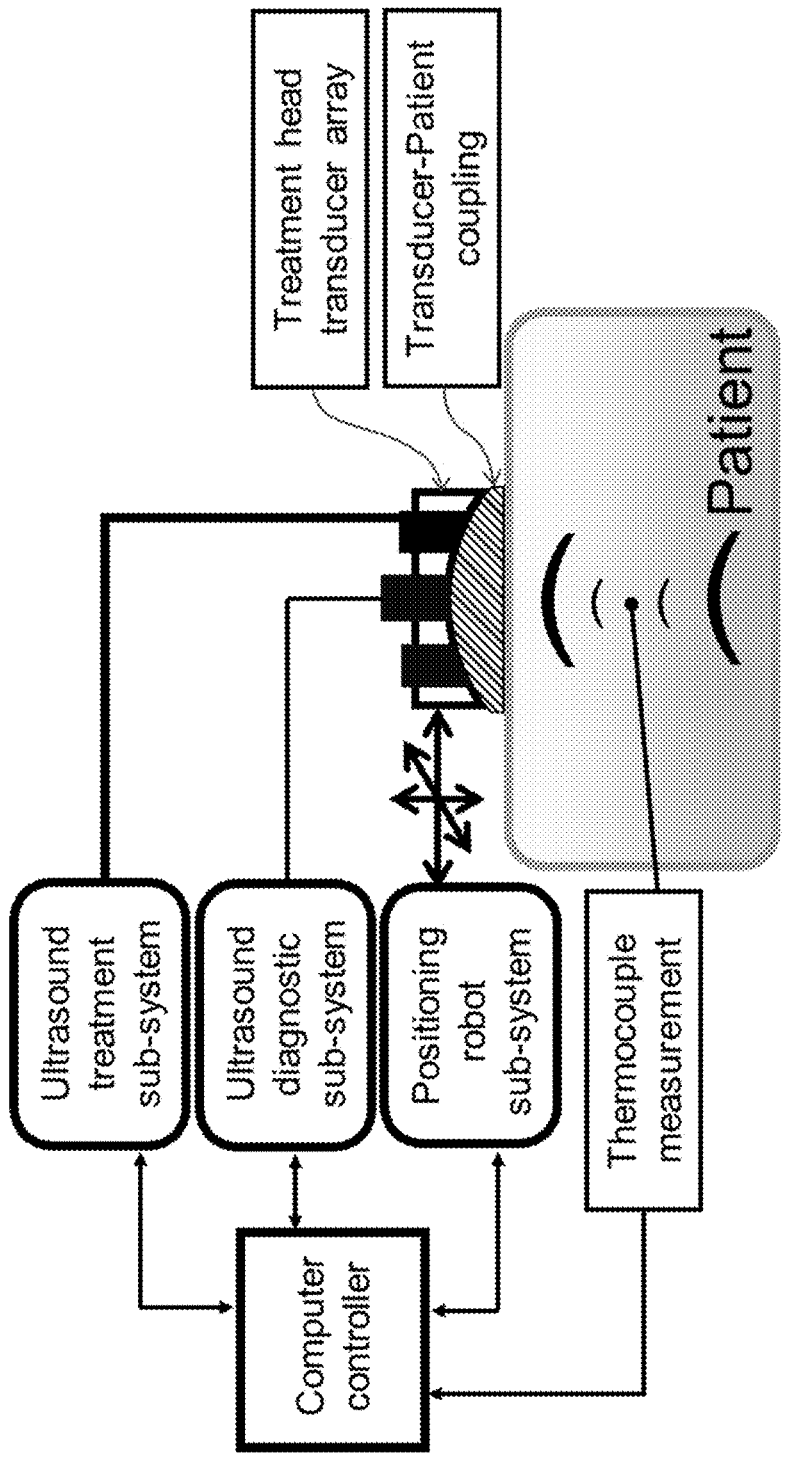

FIG. 27 illustrates the hardware architecture block diagram, in accordance with some embodiments.

Figure 28:
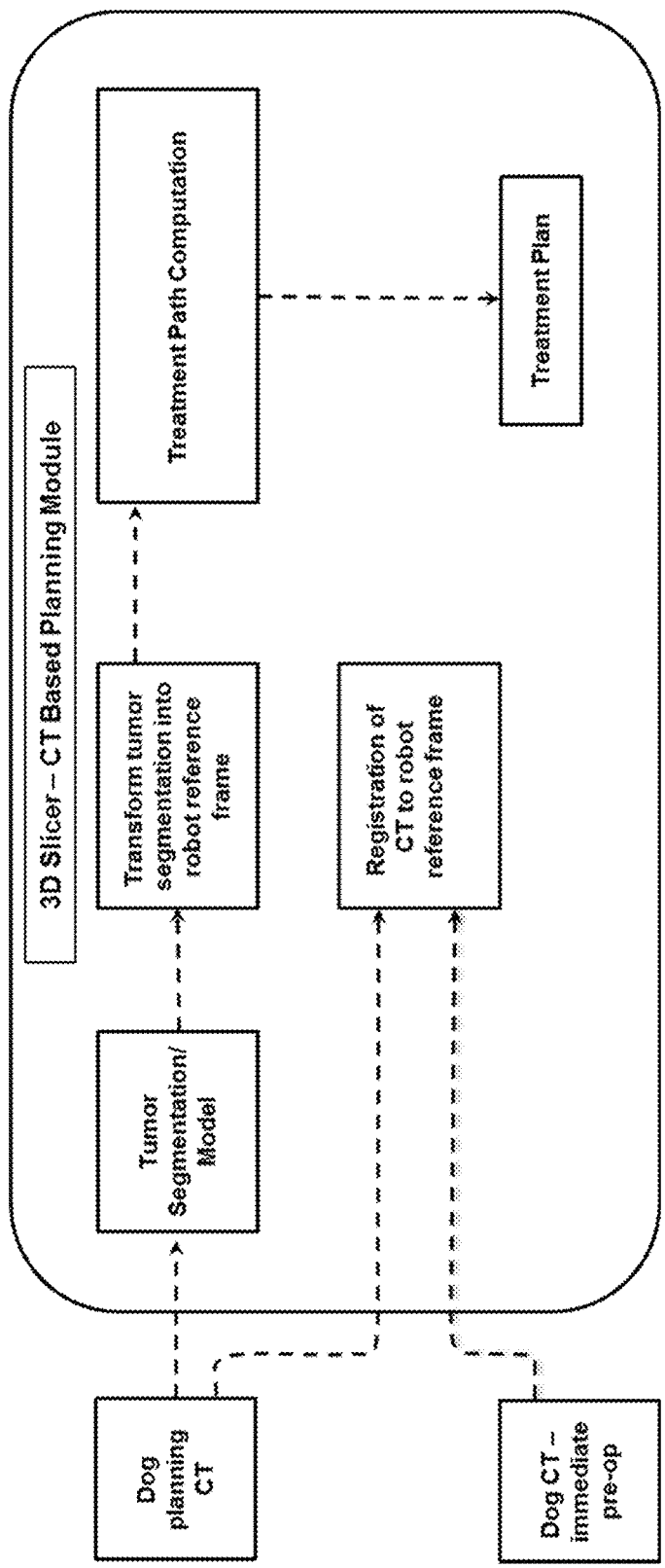

FIG. 28 illustrates the software architecture treatment plan block diagram, in accordance with some embodiments.

Figure 29:
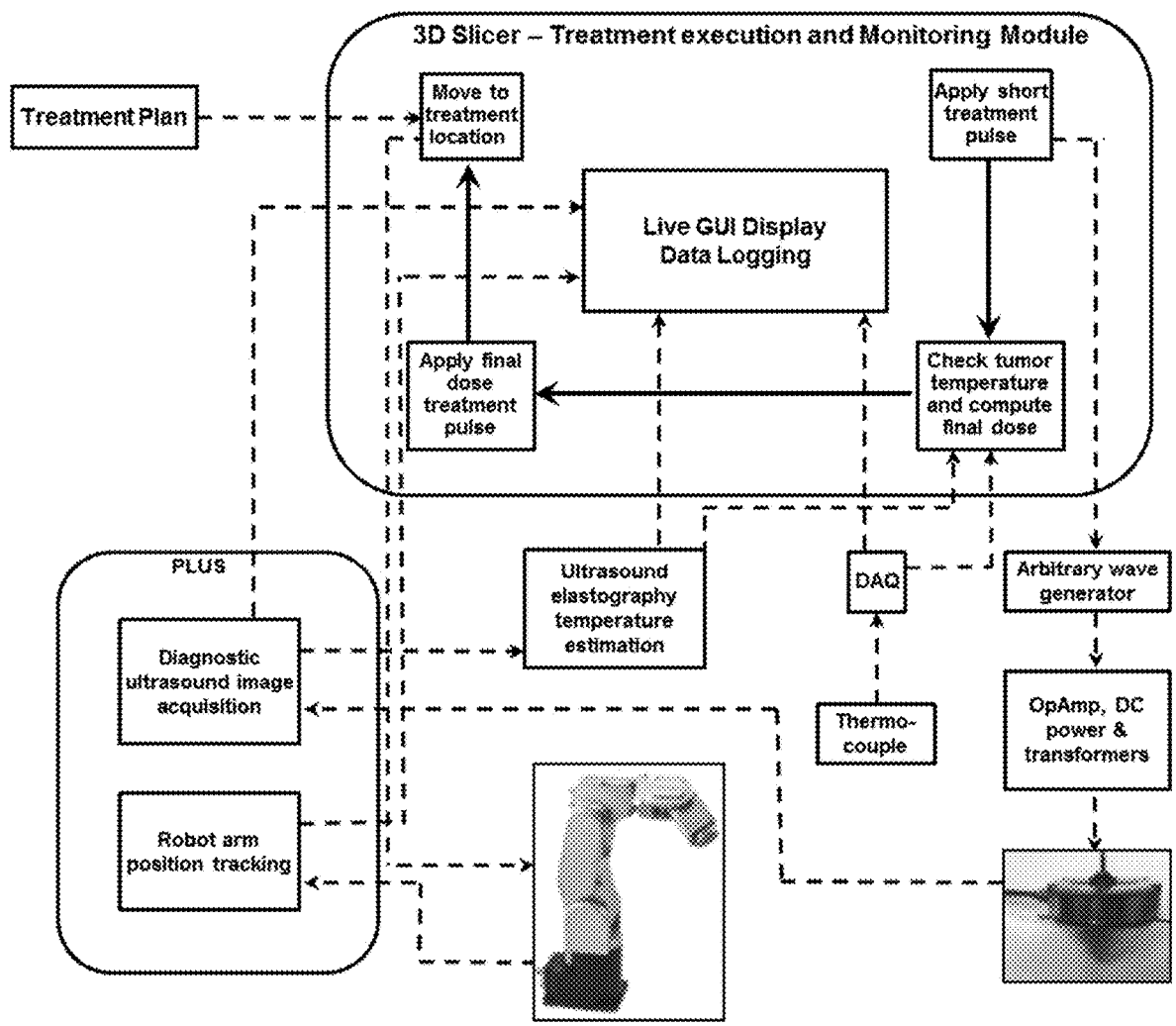

FIG. 29 illustrates the software architecture treatment execution block diagram, in accordance with some embodiments.

Figure 30:
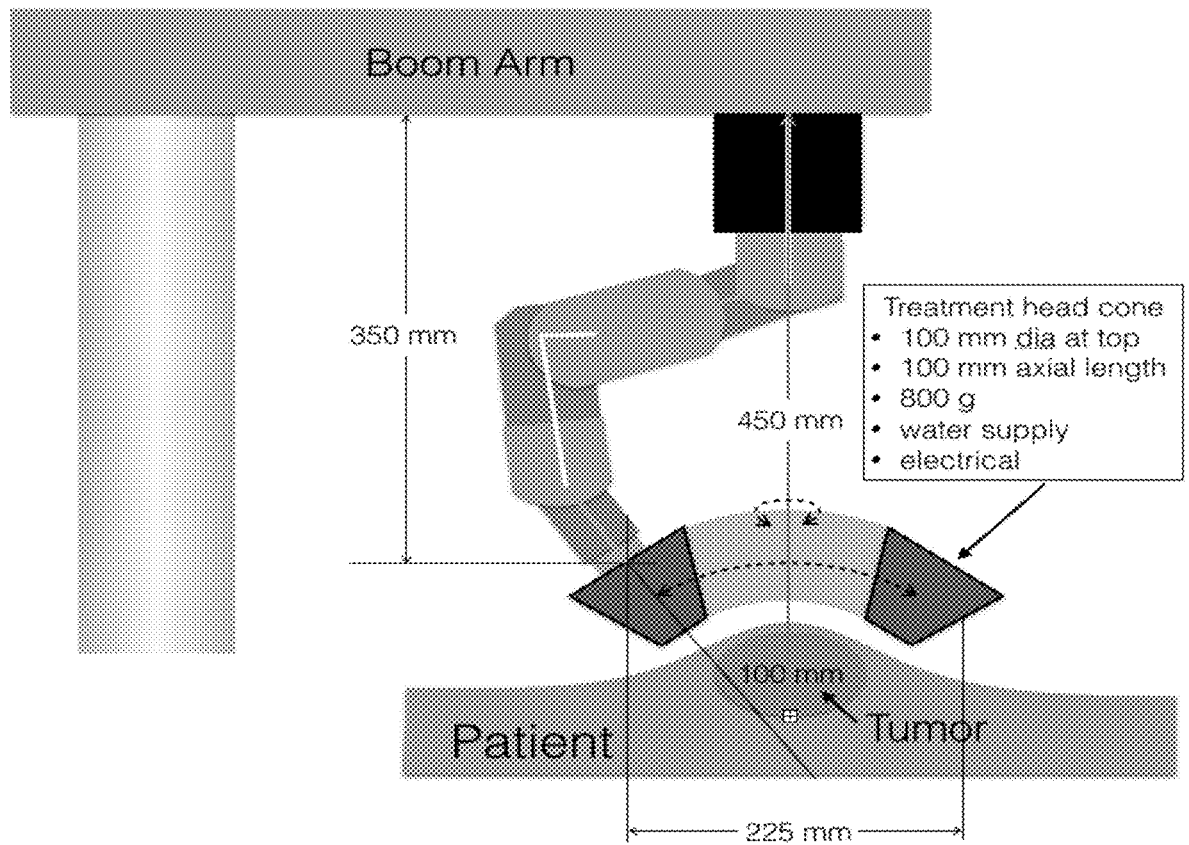

FIG. 30 illustrates translational motion of the robot and treatment, in accordance with some embodiments.

Figure 31:
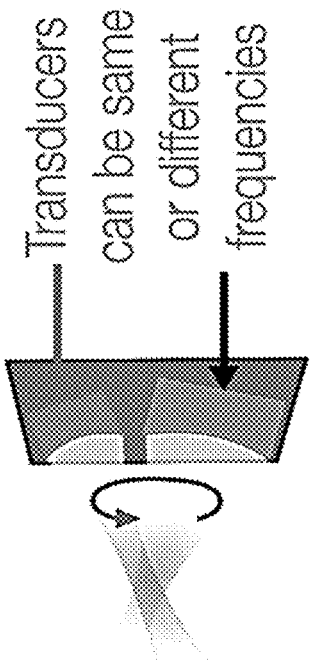

FIG. 31 illustrates a multi beam treatment head that increases the dose to focal zone relative to the surrounding tissue, in accordance with some embodiments.

Figure 32:
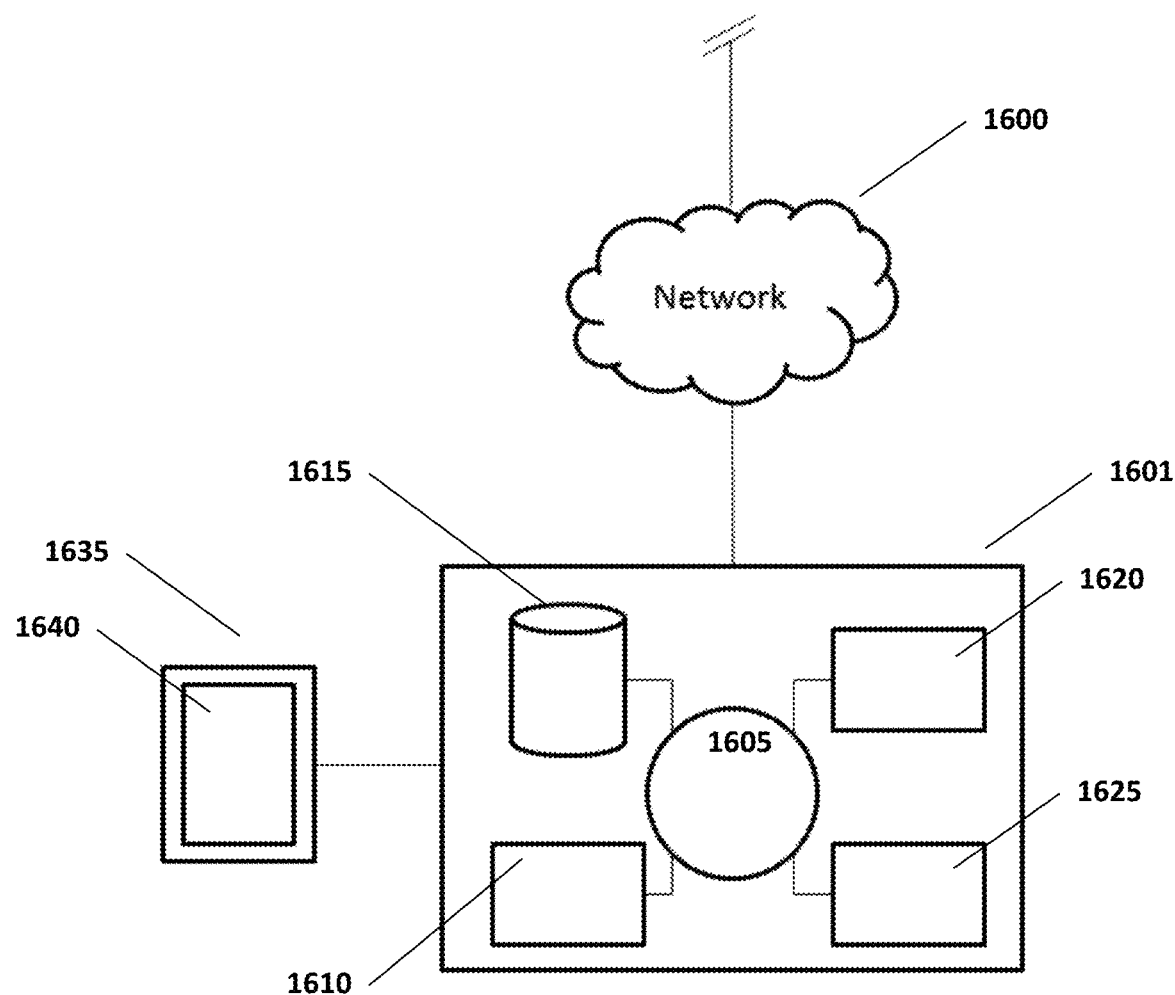

FIG. 32 illustrates an exemplary digital processing device, in accordance with some embodiments.

DETAILED DESCRIPTION OF THE INVENTION

Disclosed herein is an ultrasound (US) therapy that delivers a reduced level of energy to a treatment zone compared to high-intensity focused ultrasound (HIFU) configurations, for example sub-ablative levels. Ultrasound can readily penetrate to and throughout tumors, is localizable with millimeter precision, and provides an external, operator control of toxicity. In some instances, US may be utilized as an imaging modality. Such a characteristic can compare to other energy based modalities such as RF ablation and electroporation that do not offer imaging capability. Also, advantageously, US generally does not comprise an inherent toxicity of ionizing radiation, including the lifetime maximum tolerated dose (MTD) that limits the total dose. In other instances, the US toxicity can be tuned by varying the intensity and duration between nontoxic imaging and the ablative toxicity of HIFU. These treatments may utilize ultrasound treatment parameters and regimens that function in part through the unfolding of proteins, disruption of ER processes within cancer cells, and ensuing production and display of immunogenic DAMPs on cancer cells and within tumor microenvironments.

In an exemplary embodiment, the treatment of a particular lesion volume is for a short time (e.g. ~1.5 sec) at 1 MHz continuous power, with tumor tissue temperature elevated to less than about 45° C. This ultrasound treatment, generated using a concave transducer to focus the ultrasound in a treatment zone and herein termed "low energy non-ablative focused ultrasound" (LOFU), produces mild mechanical and thermal stress in tumor cells, while avoiding cavitation and coagulative necrosis both of which result in tissue damage. A non-ablative "sonic" stress response is induced in the tumor that increases the expression of heat shock proteins without actually killing them directly. LOFU has the potential to release immunomodulatory factors, including heat shock proteins, and can be effective in inducing tumor-specific immune activation. Using a murine B16 melanoma tumor model, it is disclosed that LOFU treatment reverses tumor-induced tolerance, resulting in increased effector cytokine production in tumor-antigen specific CD4+ T cells, which appears to be caused by the release of immunogenic molecules by the tumor cells. Also, the combination of LOFU with an ablative hypofractionated Cone Beam computed tomography (CT) image-guided radiation therapy (IGRT) results in synergistic control of primary tumors and also causes reduction in spontaneous pulmonary metastases and prolongs recurrence free survival in immunocompetent mice. In addition, LOFU was found to sensitize cancer cells (prostate cancer in the example) to a chemotherapeutic drug.

In some embodiments, tumor-focal energy may be combined with bioactive agents, including immune cell growth factors, and agents that target the PD-1 axis, CSF-1R, Tie2 and STING pathways. In some embodiments, energy may be combined with chemotherapies known to produce immunogenic patterns within typical tumor microenvironments (TMEs). In some embodiments, energy may be combined with bioactive molecules that reduce physical barriers in tumors, including non-cellular protein network density.

In an exemplary embodiment, the LOFU (also termed "acoustic priming therapy" herein) involves the application of ultrasound at an acoustic power between 10 and 1000 $W/cm^2$ spatial peak temporal average intensity ($I_{spta}$) in a treatment zone, with the ultrasound applied continuously for a time in the range of 0.5 to 5 seconds, wherein the frequency is in the range of 0.01 to 10 MHz and the mechanical index is less than 4. Mechanical Index (MI) is the rarefaction pressure in units of MPa over the square root of the central frequency in units of MHz. The energy and intensity of ultrasound applied is intended to fall between energies and intensities of ultrasound that either induce primarily ablative effects or primarily diagnostic effects.

As explained in more detail below, the various treatment methods discussed herein may be administered using a LOFU or acoustic priming therapy device that includes a transducer that generates acoustic power between 10 and 1000 $W/cm^2$ spatial peak temporal average intensity ($I_{spta}$) in a treatment zone. The ultrasound is applied continuously for a time in the range of 0.5 to 5 seconds or pulsed with pulse durations of 1 to 100 ms, wherein the frequency is in the range of 0.01 to 10 MHz. In some embodiments the frequency is in the range of 0.05 to 5 MHz. In some embodiments the frequency range is from 0.1 to 2 MHz. In some embodiments the minimum diameter of any ultrasound beam in the treatment zone is about 1 cm. In an embodiment, the LOFU is administered at 10 to 100 $W/cm^2$ $I_{spta}$ in the area of treatment. In an embodiment, the LOFU is administered at 100 to 200 $W/cm^2$ $I_{spta}$ in the area of treatment. In an embodiment, the LOFU is administered at 200 to 300 $W/cm^2$ $I_{spta}$ in the area of treatment. In an embodiment, the LOFU is administered at 300 to 400 $W/cm^2$ $I_{spta}$ in the area of treatment. In an embodiment, the LOFU is administered at 400 to 500 $W/cm^2$ $I_{spta}$ in the area of treatment. In an embodiment, the LOFU is administered at 500 to 600 $W/cm^2$ $I_{spta}$ in the area of treatment. In an embodiment, the LOFU is administered at 600 to 700 $W/cm^2$ $I_{spta}$ in the area of treatment. In an embodiment, the LOFU is administered at 700 to 800 $W/cm^2$ $I_{spta}$ in the area of treatment. In an embodiment, the LOFU is administered at 800 to 900 $W/cm^2$ $I_{spta}$ in the area of treatment. In an embodiment, the LOFU is administered at 900 to 1000 $W/cm^2$ $I_{spta}$ in the area of treatment. In an embodiment, the ultrasound is applied for a time in the range of 0.5 to 1 second. In an embodiment, the ultrasound is applied for a time in the range of 1 to 2 seconds. In an embodiment, the ultrasound is applied for a time in the range of 2 to 3 seconds. In an embodiment, the ultrasound is applied for a time in the range of 3 to 4 seconds. In an embodiment, the ultrasound is applied for a time in the range of 4 to 5 seconds. In embodiment, the ultrasound is applied at a frequency of 0.01 to 1 MHz. In embodiment, the ultrasound is applied at a frequency of 1 to 2 MHz. In embodiment, the ultrasound is applied at a frequency of 2 to 3 MHz. In embodiment, the ultrasound is applied at a frequency of 3 to 4 MHz. In embodiment, the ultrasound is applied at a frequency of 4 to 5 MHz. In embodiment, the ultrasound is applied at a frequency of 5 to 6 MHz. In embodiment, the ultrasound is applied at a frequency of 6 to 7 MHz. In embodiment, the ultrasound is applied at a frequency of 7 to 8 MHz. In embodiment, the ultrasound is applied at a frequency of 8 to 9 MHz. In embodiment, the ultrasound is applied at a frequency of 9 to 10 MHz. In an embodiment, the ultrasound is applied at a frequency of higher than 10 MHz.

A method is provided for increasing the efficacy of a chemotherapy in a subject comprising administering to the subject (i) an amount of low intensity focused ultrasound (LOFU) and (ii) an amount of a chemotherapeutic drug, wherein the chemotherapeutic drug effects endoplasmic reticulum (ER) stress and/or unfolded protein response (UPR) in a tumor cell, wherein the amounts (i) and (ii) together are sufficient to increase the efficacy of the chemotherapy.

Also provided is a method of increasing the efficacy of a chemotherapy in a predetermined volume of tissue in a subject which volume is less than the whole subject, comprising (i) administering to the subject an amount of a chemotherapeutic drug, wherein the chemotherapeutic drug effects endoplasmic reticulum (ER) stress and/or unfolded protein response (UPR) in a tumor cell and (ii) administering to the predetermined volume of tissue in a subject an amount of low intensity focused ultrasound (LOFU), wherein the amounts of (i) and (ii) together are sufficient to increase efficacy of the chemotherapy within the predetermined volume of tissue.

Also provided is a method of treating a tumor in a subject, wherein the tumor is resistant to a chemotherapeutic drug, comprising:
  receiving identification of the subject as having a tumor resistant to a specified chemotherapeutic drug;
  administering (i) an amount of low intensity focused ultrasound (LOFU) and (ii) an amount of the specified chemotherapeutic drug,
  wherein the amounts (i) and (ii) together are sufficient to treat the tumor.

Also provided is a method of treating a chemoresistant tumor in a subject, wherein the tumor has become chemoresistant to a previously administered chemotherapeutic drug, comprising:

administering to the subject (i) an amount of low intensity focused ultrasound (LOFU) and (ii) an amount of the chemotherapeutic drug, wherein the amounts (i) and (ii) together are sufficient to treat the chemoresistant tumor.

In an embodiment of the methods, the chemotherapeutic drug effects endoplasmic reticulum (ER) stress and/or unfolded protein response (UPR) in a tumor cell.

In an embodiment of the methods, the chemotherapeutic drug has previously been administered to the subject a plurality of times and wherein the tumor has been diagnosed as resistant to the chemotherapeutic drug subsequent to an initial administration of the chemotherapeutic drug.

In an embodiment of the methods involving chemoresistance, the methods can further comprising receiving identification of the subject as having the tumor chemoresistant to a previously administered chemotherapeutic drug.

In an embodiment of the methods, the chemotherapeutic drug effects UPR in a tumor cell.

In an embodiment of the methods, the chemotherapeutic drug effects effects ER stress in a tumor cell.

In an embodiment of the methods, the amounts of (i) and (ii) together are sufficient to induce apoptosis of tumor cells or increase apoptosis of tumor cells.

In an embodiment of the methods, the amount of administered chemotherapeutic drug alone, in the absence of increasing the efficacy, is a sub-therapeutic dose with regard to treating a tumor.

In an embodiment of the methods, the LOFU administered is directed at a location of the tumor in the subject.

In an embodiment of the methods, the low intensity focused ultrasound (LOFU) is administered to the subject prior to, or concurrent with, the chemotherapy or the radiotherapy or the immunotherapy. In an embodiment of the methods, the LOFU is administered to the subject prior to the radiotherapy being administered. In an embodiment of the methods, the LOFU is administered to the subject prior to the chemotherapy being administered. In an embodiment of the methods, the LOFU is administered to the subject prior to the immunotherapy being administered. In an embodiment of the methods, the LOFU is administered to the subject concurrent with the radiotherapy being administered. In an embodiment of the methods, the LOFU is administered to the subject concurrent with the chemotherapy being administered. In an embodiment of the methods, the LOFU is administered to the subject concurrent with the immunotherapy being administered.

In an embodiment of the methods, the chemotherapeutic drug is an HSP90 inhibitor. In an embodiment the HSP90 inhibitor is 17AAG (tanespimycin or 17-N-allylamino-17-demethoxygeldanamycinan). In an embodiment, the chemotherapy drug is an HSP90 inhibitor. An example of an HSP90 inhibitor is 17AAG (tanespimycin or 17-N-allylamino-17-demethoxygeldanamycinan). In an embodiment, the chemotherapy drug is an alkylating agent. In an embodiment, the chemotherapy drug is trabectidin. In an embodiment, the chemotherapy drug is a mustard gas derivative. In an embodiment, the chemotherapy drug is a metal salt. In an embodiment, the chemotherapy drug is a plant alkaloid. In an embodiment, the chemotherapy drug is a antitumor antibiotic. In an embodiment, the chemotherapy drug is an antimetabolite. In, an embodiment, the chemotherapy drug is a topoisomerase inhibitor. In an embodiment, the chemotherapy drug is a protesomal inhibitor. In an embodiment, the chemotherapy drug is a chemotherapeutic NSAID. In an embodiment, the chemotherapy drug is tamoxifen. In an embodiment, the chemotherapy drug is a nonsteroidal antiandrogen (NSAA). In an embodiment, the chemotherapy drug is apalutamide. In an embodiment, the chemotherapy drug comprises a hormonal therapy. In an embodiment, the chemotherapy drug is one of the miscellaneous antineoplastics listed herein below.

In an embodiment of the methods, the LOFU is delivered via an ultrasound beam from an ultrasound machine comprising a transducer and the machine and subject are positioned such that at least a portion of the tumor is positioned at the focus of the transducer. In an embodiment of the methods, the LOFU is delivered to at least a portion of the tumor and the position of the tumor in the subject is monitored via an imaging technique. In an embodiment of the methods, the imaging technique is magnetic resonance imaging. In an embodiment of the methods, the imaging technique is computed tomography. In an embodiment of the methods, the imaging technique is ultrasound imaging.

In an embodiment of the methods, the LOFU is administered to multiple volumes within the tumor at least once over a period of time of less than one hour.

In an embodiment of the methods, the LOFU is non-ablative. In an embodiment of the methods, the LOFU does not cause cavitation in the tissue it is administered to.

In an embodiment of the methods, an ultrasound component of the LOFU is administered at a frequency of from 0.5 MHz to 1.5 MHz. In an embodiment of the methods, the LOFU is administered for 1 to 3 seconds. In an embodiment of the methods, the LOFU is administered by an ultrasound beam such that in the treatment zone in situ intensity is from 250 W/cm$^2$ to 750 W/cm$^2$ at 1 mm to 75 mm tissue depth in the subject.

In an embodiment of the methods, the LOFU is administered over the entire tumor volume. In an embodiment of the methods, the method delivers energy in the range of 300 to 3000 joules per cc of tumor to the tumor. In an embodiment of the methods, high intensity focused ultrasound (HIFU) is not administered to the subject. In an embodiment, HIFU is focused ultrasound that affects a tissue temperature in the focal zone of about 80° C. or above. HIFU causes increase temperature up to 60 to 85ºC for few seconds of exposure time to solid tissue and/or causes thermal ablation in the tissue. Thermal ablation is usually achieved with power intensity of greater than 1 kW/cm$^2$ with reported frequency of 0.8 to 7 MHz. On the other hand, LOFU can be achieved with power intensity of, for example, 1 to 3 W/cm$^2$ and frequency of 0.5 to 3 MHz (see other LOFU ranges herein, however). LOFU can be continuous (100% DC) or pulsed (<100% DC, some literatures referred to as low intensity pulsed ultrasound or LIPUS) focused ultrasound by adjusting the duty cycle. Continuous LOFU at 1 MHz and 1 W/cm$^2$ for 10 minutes can produce a 0.1° C. elevation in tissue. In-vivo experiments on muscle tissue show that sonication at 1 MHz frequency increases temperature at a rate of 0.04° C./min at 0.5 W/cm$^2$; 0.16° C./min at 1.0 W/cm$^2$; 0.33° C./min at 1.5 W/cm$^2$; 0.38° C./min at 2.0 W/cm$^2$.

In an embodiment of the methods, the effect of the amount of radiotherapy and the amount of LOFU is synergistic in treating the tumor.

In an embodiment of the methods, the subject is human.

In an embodiment of the methods, the tumor is a tumor of the prostate, breast, nasopharynx, pharynx, lung, bone, brain, sialaden, stomach, esophagus, testes, ovary, uterus, endometrium, liver, small intestine, appendix, colon, rectum, bladder, gall bladder, pancreas, kidney, urinary bladder, cervix, vagina, vulva, prostate, thyroid or skin, head or neck, glioma or soft tissue sarcoma. In an embodiment of the methods, the tumor is a prostate cancer.

In an embodiment of the methods, the metastasis is a lung metastasis.

In an embodiment of the methods, the LOFU is administered with a device comprising: a control system that generates a frequency waveform; and one or more transducers configured to produce ultrasound based on a frequency waveform between 1 and 1000 W/cm$^2$ spatial peak temporal average acoustic output intensity ($I_{spta}$) in a treatment zone, wherein ultrasound is applied continuously to the treatment zone for a time in the range of from 0.5 to 5 seconds, wherein ultrasound frequency is in the range of 0.01 to 10 MHz and wherein mechanical index of any beam is less than 4. In an embodiment of the methods, each of the one or more transducers are configured to produce ultrasonic beams based on the frequency waveform with central frequencies in the range of 0.05 to 5 MHz and an acoustic output intensity of between 20 and 1000 W/cm$^2$. In an embodiment of the methods, each of the one or more transducers are configured to produce ultrasonic beams based on the frequency waveform with central frequencies in the range of 0.5 to 1.5 MHz and an acoustic output intensity of between 20 and 1000 W/cm$^2$. In an embodiment of the methods, each transducer is configured to produce columnated ultrasound such that the beam profile waist at −3 dB is not less than 5 mm in a treatment zone. In an embodiment of the methods, one or more beams are mechanically moved during treatment. In an embodiment of the methods, the one or more transducers comprise two or more transducers configured to operate sequentially or simultaneously and produce ultrasound of average spatial peak 250 W/cm$^2$ in a treatment zone during a treatment period. In an embodiment of the methods, the one or more transducers are configured produce ultrasound having a frequency within the range of 10 kHz to 300 kHz. In an embodiment of the methods, the one or more transducers are configured produce ultrasound having a frequency within the range of 300 kHz to 3 MHz. In an embodiment of the methods, one or more transducers operate at a frequency of 300 kHz to 3 MHz and one or more transducers operates at a frequency of between 30 and 300 kHz. In an embodiment of the methods, two or more ultrasound transducers generate ultrasound beams that pass through a treatment zone, with each beam having an $I_{spta}$ in the intersection zone in the range of 10 to 500 W/cm$^2$. In an embodiment of the methods, the treatment time is less than 5 seconds per cubic centimeter of tumor. In an embodiment of the methods, two transducers generate ultrasound beams that intersect within a treatment zone, with each beam having an $I_{spta}$ in the intersection zone in the range of 50 to 500 W/cm$^2$. In an embodiment of the methods, three transducers generate ultrasound beams that pass through a treatment zone, with each beam having an $I_{spta}$ in the intersection zone in the range of 50 to 500 W/cm$^2$. In an embodiment of the methods, the one or more transducers produce ultrasonic beams that are substantially in phase with one another within the treatment zone. In an embodiment of the methods, two ultrasound beams emanating from separate ultrasound transducers are substantially in phase and intersect within a treatment zone, and each beam has an acoustic power spatial peak intensity in the intersection zone in the range of 70 to 100 W/cm$^2$ and the ultrasound is applied continuously from 1 to 5 seconds.

In an embodiment of the methods, three ultrasound beams emanating from separate ultrasound transducers are substantially in phase and intersect within a treatment zone, and each beam has an acoustic power spatial peak intensity in the intersection zone in the range of 50 to 70 W/cm$^2$ and the ultrasound is applied continuously for 1 to 5 seconds. In an embodiment of the methods, ultrasonic beams originating from separate transducers each produce an $I_{spta}$ in the range of approximately 100 to 1000 W/cm$^2$ in the treatment zone. In an embodiment of the methods, at least one transducer generates an ultrasonic beam with a high intensity diameter that is substantially larger in size than the treatment zone and is directed such that the treatment zone is entirely within the beam. In an embodiment of the methods, an intense treatment zone is formed where two or more ultrasound beams cross paths, the intense treatment zone being equal to or greater than about 1 cm perpendicular to the transmitted energy direction and also equal to or greater than about 1 cm parallel to the transmitted direction. In an embodiment of the methods, acoustic pressure applied to a treatment zone from each transducer is 0.1 to 10 MPa. In an embodiment of the methods, the number of transducers that provide the intense ultrasound treatment zone is between 1 and 1000. In an embodiment of the methods, the ultrasound from the one or more transducers is applied continuously during the treatment time. In an embodiment of the methods, the ultrasound is produced with a duty cycle in the range of 1 on time units to 9 off time units. In an embodiment of the methods, the transducers are configured to produce ultrasound in single frequency tones or multi-frequency chirps. In an embodiment of the methods, the one or more transducers are operated sequentially in time. In an embodiment of the methods, the total energy delivered to the target tissue and desired margin around the target tissue for the entire course of the application is greater than that to surrounding tissues. In an embodiment of the methods, the one or more transducers are configured so that the frequency of ultrasound is swept during application. In an embodiment of the methods, the one or more transducers comprise two-dimensional phased arrays, In an embodiment of the methods, the one or more transducers comprise annular arrays. In an embodiment of the methods, the one or more transducers comprise three-dimensional phased arrays. In an embodiment of the methods, the one or more transducers are incorporated into one or more endoscopic devices. In an embodiment of the methods, the one or more transducers are incorporated into a magnetic resonance imaging machine.

In an embodiment of the methods, the one or more transducers are incorporated into a radiotherapy treatment machine.

In an embodiment of the methods, the one or more transducers are configured to produce ultrasound so that the maximum temperature reached in the treatment zone is less than 45° C. during a treatment where ultrasound is applied to the treatment zone for about 2 seconds or less.

In an embodiment of the methods, the one or more transducers are configured to produce ultrasound so that the maximum temperature reached in the treatment zone is less than 50° C. during a treatment where ultrasound is applied to the treatment zone for about 2 seconds or less.

In an embodiment of the methods, the one or more transducers are configured to produce ultrasound so that the maximum temperature reached in the treatment zone is less than 55° C. during a treatment where ultrasound is applied to the treatment zone for about 2 seconds or less.

In an embodiment of the methods, the LOFU and radiotherapy are administered by a system comprising:

a LOFU device comprising:
a control system that generates a frequency waveform; and
one or more transducers configured to produce ultrasound based on a frequency waveform between 1 and 1000 W/cm² spatial peak temporal average acoustic output intensity ($I_{spta}$) in a treatment zone, wherein the ultrasound is applied continuously for a time in the range of from 0.5 to 5 seconds, and wherein ultrasound frequency is in the range of 0.01 to 10 MHz; a radiotherapy treatment machine; and
a control system operatively configured to control the LOFU device and the radiotherapy treatment machine so that a first amount of the ultrasound and a second amount of radiotherapy are administered to a subject, wherein the first and second amounts together are sufficient to treat a tumor in the subject.

A method of treating a tumor in a subject is provided comprising administering to the subject (i) an amount of low intensity focused ultrasound (LOFU) and (ii) an amount of chemotherapy or an amount of radiotherapy or an amount of immunotherapy, wherein the amounts of (i) and (ii) together are sufficient to treat a tumor.

In an embodiment of the method, the amount of LOFU and the amount of radiotherapy are administered to the subject. In another embodiment of the method, the amount of LOFU and the amount of radiotherapy are administered to the subject. In another embodiment of the method, the amount of LOFU and the amount of immunotherapy are administered to the subject.

A method of treating a tumor in a subject is provided comprising administering to the subject (i) an amount of low intensity focused ultrasound (LOFU) and (ii) an amount of a targeted anti-cancer therapy wherein the amounts of (i) and (ii) together are sufficient to treat a tumor. In an embodiment, the targeted therapy comprises a mAb directed to Her2 or VEGFR. In an embodiment, the targeted therapy comprises a tyrosine kinase inhibitor.

Also provided is a method of inhibiting metastasis of a tumor in a subject, comprising administering to a subject having a tumor an amount of low intensity focused ultrasound (LOFU) and an amount of a radiotherapy, wherein the amounts together are sufficient to inhibit metastasis of a tumor in a subject.

In the methods, the radiotherapy can be ablative hypofractionated radiation therapy.

Preferably, in the methods the LOFU is directed at a location of the tumor in the subject.

Also provided is a method of reducing the effective dose of an anti-cancer chemotherapy required to treat a tumor in a subject comprising administering to the subject undergoing the anti-cancer chemotherapy an amount of low intensity focused ultrasound (LOFU) sufficient to reduce the effective dose of the anti-cancer chemotherapy required to treat a tumor.

In an embodiment of each of the methods, the LOFU is administered to the subject prior to, or concurrent with, the chemotherapy or the radiotherapy or the immunotherapy.

In an embodiment the LOFU is administered to the subject prior to the radiotherapy being administered.

In the methods wherein an anti-cancer chemotherapy is administered, in an embodiment the anti-cancer chemotherapy comprises administration of an HSP90 inhibitor to the subject. The HSP90 inhibitor can be 17AAG (tanespimycin or 17-N-allylamino-17-demethoxygeldanamycinan). In an embodiment, the chemotherapy drug is an alkylating agent. In an embodiment, the chemotherapy drug is trabectidin. In an embodiment, the chemotherapy drug is a mustard gas derivative. In an embodiment, the chemotherapy drug is a metal salt. In an embodiment, the chemotherapy drug is a plant alkaloid. In an embodiment, the chemotherapy drug is a antitumor antibiotic. In an embodiment, the chemotherapy drug is an antimetabolite. In an embodiment, the chemotherapy drug is a topoisomerase inhibitor. In an embodiment, the chemotherapy drug is a protesomal inhibitor. In an embodiment, the chemotherapy drug is a chemotherapeutic NSAID. In an embodiment, the chemotherapy drug is tamoxifen. In an embodiment, the chemotherapy drug is a nonsteroidal antiandrogen (NSAA). In an embodiment, the chemotherapy drug is apalutamide. In an embodiment, the chemotherapy drug comprises a hormonal therapy. In an embodiment, the chemotherapy drug is one of the miscellaneous antineoplastics listed hereinbelow.

In an embodiment of the methods, the LOFU is delivered via an ultrasound beam from an ultrasound machine comprising a transducer and the machine and subject are positioned such that the at least a portion of the tumor is positioned at the focal length of the transducer.

In an embodiment of the methods, the LOFU is delivered to at least a portion of the tumor and the position of the tumor is monitored via an imaging technique. Magnetic resonance imaging can be such an imaging technique.

In the methods, the LOFU can be administered to multiple points within the tumor at least once over a period of time of less than one hour.

In an embodiment of the methods, the LOFU is non-ablative.

In an embodiment of the methods, the LOFU is administered at a frequency of from 0.5 MHz to 1.5 MHz.

In an embodiment of the methods, the LOFU is administered for 1.5-3 seconds

In an embodiment of the methods, the LOFU is administered by an ultrasound beam such that at the focus of the ultrasound beam the in situ intensity is from 250 W/cm² to 750 W/cm². In an embodiment of the methods, the LOFU is administered by an ultrasound beam such that at the focus of the ultrasound beam the in situ intensity is from 250 W/cm² to 750 W/cm² at 1 mm to 75 mm tissue depth in the subject. In an embodiment of the methods, the LOFU is administered by an ultrasound beam such that at the focus of the ultrasound beam the in situ intensity is from 350 W/cm² to 650 W/cm² at 1 mm to 75 mm tissue depth in the subject. In an embodiment of the methods, the LOFU is administered by an ultrasound beam such that at the focus of the ultrasound beam the in situ intensity is from 450 W/cm² to 550 W/cm² at 1 mm to 75 mm tissue depth in the subject.

The LOFU can be administered over the entire tumor volume, or can be administered over a portion of the tumor volume. In a preferred embodiment the LOFU is administered over the entire tumor volume.

In an embodiment, of the method the LOFU delivers at least 500 to 5000 joules of energy per cc of tumor tissue through the tumor. In an embodiment, of the method the LOFU delivers at least 1000 to 4000 joules of energy per cc of tumor tissue. In an embodiment, of the method the LOFU delivers at least 2000 to 3000 joules of energy per cc of tumor tissue through the tumor.

In an embodiment, high intensity focused ultrasound (HIFU) is not administered to the subject. In an embodiment, high intensity focused ultrasound has not been administered to the subject. In an embodiment, high intensity focused ultrasound has not been administered to the tumor. In an embodiment where LOFU is administered to the subject before the anti-cancer therapy, high intensity focused ultrasound is not administered to the subject after the LOFU is administered and before the anti-cancer therapy is administered.

In an embodiment, the anti-cancer therapeutic effect of the amount of radiotherapy and the amount of LOFU is synergistic.

In an embodiment, the LOFU administration raises the tissue/tumor temperature to between 40° C.-45° C. In an embodiment, the LOFU administration raises the tissue/tumor temperature to no more than 40° C. In an embodiment, the LOFU administration raises the tissue/tumor temperature to no more than 45° C. In an embodiment, the LOFU administration raises the tissue/tumor temperature to no more than 50° C. HIFU will generally raise tissue temperatures more than this.

In an embodiment, the LOFU is administered for 0.5 to 3 seconds. In an embodiment, the LOFU is administered for 1.5 to 3 seconds. In an embodiment, the LOFU is administered with a 100% duty cycle. In an embodiment, the LOFU is administered with one of the separate embodiments of a 10, 20, 30, 40, 50, 60, 70, 80 or 90% duty cycle.

Also provided is a method of sensitizing a tumor in a subject to an amount of an anti-cancer therapy the method comprising administering to the subject, prior to, during or after the anti-cancer therapy, an amount of low intensity focused ultrasound (LOFU) effective to sensitize a tumor in a subject to an amount of an anti-cancer therapy. In an embodiment, the anti-cancer therapy comprises a chemotherapy, or a radiotherapy, or an immunotherapy, or a targeted therapy, or a surgery. In an embodiment, the anti-cancer therapy comprises a chemotherapy. In an embodiment, the anti-cancer therapy comprises an immunotherapy. In an embodiment, the anti-cancer therapy comprises a radiotherapy. In an embodiment, the anti-cancer therapy comprises surgery, for example, to excise the tumor. The method can further comprise administering the anti-cancer therapy to the subject. Sensitizing a tumor to an amount of an anti-cancer therapy makes the tumor more susceptible to the treatment. For example, a parameter by which tumor treatment may be measured, such as tumor volume reduction, is greater for a given amount of an anti-cancer therapy applied to the sensitized tumor as compared to the same amount of an anti-cancer therapy applied to a non-sensitized tumor of equivalent mass, vascularity, position and type in the same or an equivalent subject. In an embodiment, the amount of LOFU effective to sensitize a tumor in a subject to an amount of an anti-cancer therapy and the anti-cancer therapy are synergistic in effect.

In any of the methods described herein, the subject is a mammal. In an embodiment, the subject is a human.

The tumor referred to in the methods can be a tumor of the prostate, breast, nasopharynx, pharynx, lung, bone, brain, sialaden, stomach, esophagus, soft tissue, testes, ovary, uterus, endometrium, liver, small intestine, appendix, colon, rectum, bladder, gall bladder, pancreas, kidney, urinary bladder, cervix, vagina, vulva, prostate, thyroid or skin, head or neck, or is a glioma or a soft tissue sarcoma. In one embodiment, the tumor is a prostate cancer. In one embodiment, the tumor is a soft tissue sarcoma. In an embodiment the primary tumor is treated. In an embodiment the secondary tumor is treated, and the secondary tumor may comprise a metastatic or recurrent tumor, for example. In an embodiment, treatment of the tumor reduces the likelihood of a secondary tumor. In one embodiment, the metastasis comprises one or more lung metastases.

The term "tumor," as used herein, and unless otherwise specified, refers to a neoplastic cell growth, and includes pre-cancerous and cancerous cells and tissues. Tumors usually present as a lesion or lump. In an embodiment, the tumor is a malignant neoplasm.

As used herein "metastasize" (or grammatical equivalent) means, in regard to a cancer or tumor, the spread of the cancer or tumor from one organ or tissue of a subject to another organ or tissue of the subject spatially apart from the first organ or tissue.

As used herein, "treating" a tumor means that one or more symptoms of the disease, such as the tumor itself, vascularization of the tumor, or other parameters by which the disease is characterized, are reduced, ameliorated, inhibited, placed in a state of remission, or maintained in a state of remission. "Treating" a tumor also means that one or more hallmarks of the tumor may be eliminated, reduced or prevented by the treatment. Non-limiting examples of such hallmarks include uncontrolled degradation of the basement membrane and proximal extracellular matrix, migration, division, and organization of the endothelial cells into new functioning capillaries, and the persistence of such functioning capillaries. In an embodiment, treating the tumor means reducing the size or volume of the tumor.

As used herein, "inhibiting metastasis" of a tumor in a subject means that one or more symptoms or one or more other parameters by which metastatic disease is characterized, are reduced, ameliorated, or inhibited. Non-limiting examples of such parameters include uncontrolled degradation of the basement membrane and proximal extracellular matrix, and travel of tumor cells through the bloodstream or lymphatics, invasion, dysregulated adhesion, and proliferation at secondary site, either distal or local. In an embodiment, treating the metastasis means reducing the development or inhibiting the development of metastases.

Radiotherapy is well-known in the art. Radiotherapy as encompassed herein includes medically therapeutic radiation delivered by a machine outside the body (external-beam radiation therapy), or from radioactive material placed in the body near cancer cells (internal radiation therapy, also called brachytherapy) or systemic radiation therapy. Radiotherapy as encompassed herein includes 3-dimensional conformal radiation therapy (3D-CRT), intensity-modulated radiation therapy (IMRT), image-guided radiation therapy (IGRT), external beam radiation therapy (EBRT), and tomotherapy. The radiotherapy may also be part of a stereotactic radiosurgery or stereotactic body radiation therapy (SBRT). Delivery by any particle beam known in the art is encompassed also, for example proton therapy, carbon ion therapy, or other charged particle beams.

In an embodiment, the radiotherapy is CT image guided. In an embodiment, the radiotherapy is hypofractionated, cone beam CT image-guided radiotherapy. All combinations of the various elements described herein are within the scope of the invention unless otherwise indicated herein or otherwise clearly contradicted by context.

Chemotherapeutic drugs which may be used in the invention are various. Examples of chemotherapeutic drugs include:
  tamoxifen; apalutamide; hormonal therapies;
  alkylating agents (e.g. trabectidin ((1'R,6R,6aR,7R,13S,14S,16R)-6',8,14-trihydroxy-7',9-dimethoxy-4,10,23-trimethyl-19-oxo-3',4',6,7,12,13,14,16-octahydrospiro[6,16-(epithiopropano-oxymethano)-7,13-imino-6aH-1,3-dioxolo[7,8] isoquino[3,2-b][3]benzazocine-20,1' (2'H)-isoquinolin1-5-yl acetate));
  mustard gas derivatives (e.g. mechlorethamine, cyclophosphamide, chlorambucil, melphalan, and ifosfamide);

ethylenimines (e.g. thiotepa and hexamethylmelamine);
alkylsulfonates (e.g. busulfan);
hydrazines and triazines (e.g. altretamine, procarbazine, dacarbazine and temozolomide);
nitrosureas (e.g. carmustine, lomustine and streptozocin);
metal salts (e.g. carboplatin, cisplatin, and oxaliplatin);
plant alkaloids (e.g. *vinca* alkaloids such as vincristine, vinblastine and vinorelbine, taxanes such as paclitaxel and docetaxel, podophyllotoxins such as etoposide and tenisopide, camptothecan analogs (topoisomerase inhibitors) such as irinotecan and topotecan);
antitumor antibiotics (e.g. anthracyclines: doxorubicin, daunorubicin, epirubicin, mitoxantrone, and idarubicin; chromomycins: dactinomycin and plicamycin; miscellaneous ones such as mitomycin and bleomycin);
antimetabolites (e.g. folic acid antagonists: methotrexate; pyrimidine antagonists: 5-fluorouracil, foxuridine, cytarabine, capecitabine, and gemcitabine; purine antagonist: 6-mercaptopurine and 6-thioguanine; adenosine deaminase inhibitors: cladribine, fludarabine, nelarabine and pentostatin);
topoisomerase inhibitors (e.g. ironotecan, topotecan; amsacrine, etoposide, etoposide phosphate, teniposide);
protesomal inhibitors;
Chemotherapeutic NSAIDS; and
miscellaneous antineoplastics (e.g. ribonucleotide reductase inhibitor: hydroxyurea;
adrenocortical steroid inhibitor: mitotane; enzymes: asparaginase and pegaspargase;
antimicrotubule agent: estramustine; retinoids: bexarotene, isotretinoin, tretinoin (ATRA).

Chemotherapeutic drugs which effect endoplasmic reticulum (ER) stress and/or effect unfolded protein response (UPR) in cells are known in the art. For example, protesomal inhibitors such as e.g. Bortezomib (Velcade®; previously known as PS-341), elicit an ER stress response. Also, protesomal inhibitors such as e.g. Bortezomib elicit the UPR. Histone deacetylase (HDAC) inhibitors elicit an ER stress response. Chemotherapeutic NSAIDS (e.g. indomethacin, diclofenac, and celecoxib) can elicit an ER stress response and can elicit the UPR. Estrogen receptor a inhibitors such BHPI (1, 3-dihydro-3,3-bis(4-hydroxyphenyl)-7-methly-2H-indol-2-one) can activate the UPR. Platinum-containing anti-cancer drugs: cisplatin is known to elicit an ER stress response. The taxane family of drugs: paclitaxel is known to elicit an ER stress response. Anthracycines such as doxorubicin are known to elicit ER stress. Cyclophosphamide is known to elicit ER stress. See also Table 2 of Hetz et al., Nature Reviews, Drug Discovery, 12:703-719 (Sept., 2013), hereby incorporated by reference.

The endoplasmic reticulum (ER) is the site of synthesis and folding of secreted, membrane-bound and some organelle-targeted proteins. The ER is highly sensitive to stresses that perturb cellular energy levels, the redox state or $Ca^{2+}$ concentration. Such stresses reduce the protein-folding capacity of the ER, which can result in the accumulation and aggregation of unfolded proteins and/or an imbalance between the load of resident and transit proteins in the ER and the organelle's ability to process that load. This condition is referred to herein, and in the art, as "ER stress". The ER stress response can promote cellular repair and sustained survival by reducing the load of unfolded proteins through global attenuation of protein synthesis and/or upregulation of chaperones, enzymes and structural components of the ER, which enhance protein folding. This response is collectively termed as the unfolded protein response (UPR). Accumulation of unfolded proteins causes dissociation of GRP78 from PERK, ATF6 and IRE1, thereby initiating the UPR.

TABLE 1

Non-limiting examples of bioactive molecules that can be used with LOFU

| Types of action | Drug name | Mechanism of Action | Selected interactions with LOFU |
|---|---|---|---|
| Block proteosome/ degradation of misfolded protein | | | Decrease the degradation of misfolded protein that LOFU induces thereby increasing the amount of unfolded protein response to tip towards apoptosis. |
| | Bortezomib | proteosome inhibitor | ATF-4 induction by UPR can confer resistance to Bortezomib |
| | 3-methyladenine | an inhibitor of phosphatidyl inositol 3-kinase (PI3-kinase) prevented induction of ATG5 and activation of LC3-II and blocked autophagosome formation | |
| | polyphenol (green tea) epigallocatechin gallate | proteosome inhibitor | |
| | genistein | Proteosome inhibitor | |
| | curcumin | Proteosome inhibitor | |
| | resveratrol | Proteosome inhibitor/ represses XBP-1 prosurvival signaling | |

TABLE 1-continued

Non-limiting examples of bioactive molecules that can be used with LOFU

| Types of action | Drug name | Mechanism of Action | Selected interactions with LOFU |
|---|---|---|---|
| Inhibitor of autophagy | | | During times of stress, the cells will induce autophagy to immediately replenish depleting building blocks. Inhibiting the process of autophagy in cells treated with LOFU is expected to result in cells that are not able to immediately respond to the stress and thereby inducing apoptosis. |
| | 15,16-Dihydrotanshinone I (Tanshen root) | induce UPR via proteosome inhibition | |
| | Chloroquine | inhibitor of autophagy | |
| Inducer of autophagy | | | Decreasing the unfolded protein response sparked by LOFU and making cells less sensitive. If autophagy is activated for long enough then can push cells into pro-apoptotic state. A combination of increase macroautophagy plus increased UPR can provide an immunological response. |
| | rapamycin | mTOR inhibitor | |
| | temsirolimus | mTOR inhibitor | |
| | 4-O-carboxymethyl ascochlorin | agonist of the nuclear hormone receptor PPARγ; ER stress-induced autophagy and apoptosis | |
| ER stress inducer | | | Combining two different sources of UPR inducing agents can provide an additive effect to cancer killing. |
| | Celecoxib | Cox-2 inhibitor - by causing leakage of calcium from ER into cytosol | |
| | Verapamil | Ca channel inhibitor | Enhancing ER stress signaling |
| | Ritonavir | inhibits protein degradation that's synergistic with proteosome inhibitor | |
| | 3-thia fatty acid tetradecylthioacetic acid | Inducer of ER stress | |
| | Nelfinavir | modulates CHOP expression | |
| Damage DNA structure/prevents DNA synthesis | | | Inhibiting the repair mechanism to prevent cellular repair after LOFU damage. |
| | cisplatin | induce ER stress and dmg DNA | |
| | gemcitabine | Nucleoside analog | |
| Block protein synthesis | | | |
| | salubrinal | inhibitor of eIF2α phosphotase | |
| | Cycloheximide | | |

TABLE 1-continued

Non-limiting examples of bioactive molecules that can be used with LOFU

| Types of action | Drug name | Mechanism of Action | Selected interactions with LOFU |
|---|---|---|---|
| Increase death signaling | | | |
| | TRAIL | Protein ligand | |
| chemical chaperones | | | |
| | 4-phenylbutyric acid | chemical chaperone which rescue the mutant alpha1-antitrypsin phenotype | |
| chaperones inhibitor | | | |
| | geldanamycin | HSP90 inhibitor | |
| | 17-allyamino-17-demethoxy-geldanamycin (17AAG) | HSP90 inhibitor | |
| | 17-dimethylamino-ethylamino-17-demethoxygeldanamycin (17DMAG) | HSP90 inhibitor | |
| blocking sonoporation repair | | | |
| | vacuolin | a newly discovered small organic molecule that blocks the wounding- and Ca2+-triggered fusion of lysosomes with the plasma membrane | |
| | tamoxifen | selective estrogen receptor modulator used to prevent breast cancer | |
| | apalutamide | nonsteroidal antiandrogen (NSAA) medication which is used in the treatment of prostate cancer | |

TABLE 2

Non-limiting examples of immunotherapies that can be used with energy based immune priming such as LOFU.

| Category | Non-limiting examples |
|---|---|
| Dendritic cell and Tumor-associated macrophage targeted therapy Monocyte and macrophage Myeloid Derived Suppressor cell Targeted therapies | Flt3L, CD40L, GM-CSF, STING ligands and agonists, RIG1 helicase activators, anti-CD40, NKG2D ligand, anti-CSF1R, anti-Tie2, anti-TLR, TLR ligands, INF-α, TNF-β, |
| Effector T cell targeting | anti-OX40, 4-1BBL, anti-foxp40, TGF-β inhibitor, anti-CD137, artificial immunological synapse for T-cell activation, anti-CD47, anti-CD27, anti-GD2 |
| Immune checkpoint inhibition | anti-CTL4, anti-PD1, anti-VISTA, tim3, IDO inhibitor (e.g., Norharmane, Rosamarinic acid, COX-2 inhibitors, 1-Methyltryptophan, Epacadostat, navoximod) |
| HSP targeted agents | HSP105, HSP90, HSP70, HSP60, HSP27 |

The HSP targeted agents may comprise antibodies or targeting proteins, for example.

In some embodiments, exemplary agonists (activating antibodies) are anti-CD40, anti-CD27, and anti-OX40.

In some embodiments, exemplary antagonists (inhibitory or blocking antibodies) are anti-CTLA4, anti-PD1, anti-PDL1, anti-VISTA, and anti-TIM3.

In some embodiments, exemplary adjuvants are STINGL, RIG1 helices inhibitor, CpG olives, and TLR agonist.

In some embodiments, exemplary cytokines are IL-2, IL-7, IL-12, IL-15, IFNgamma.

In an embodiment of the methods, the chemotherapy drug is an HSP90 inhibitor. An example of an HSP90 inhibitor is 17AAG (tanespimycin or 17-N-allylamino-17-demethoxy-geldanamycinan). In an embodiment, the chemotherapy drug is an alkylating agent. In an embodiment, the chemotherapy drug is trabectidin. In an embodiment, the chemotherapy drug is a mustard gas derivative. In an embodiment, the chemotherapy drug is a metal salt. In an embodiment, the chemotherapy drug is a plant alkaloid. In an embodiment, the chemotherapy drug is an antitumor antibiotic. In an embodiment, the chemotherapy drug is an antimetabolite. In an embodiment, the chemotherapy drug is a topoisomerase inhibitor. In an embodiment, the chemotherapy drug is a proteasomal inhibitor. In an embodiment, the chemotherapy drug is a chemotherapeutic NSAID. In an embodiment, the chemotherapy drug is one of the miscellaneous antineoplastics listed hereinabove.

Other non-limiting examples of chemotherapy drugs or agents encompassed by the invention, unless otherwise stated, include anthracyclines, maytansinoids, alkylating agents, anti-metabolites, plant alkaloids or terpenoids, and cytotoxic antibiotics. In embodiments, the chemotherapy agent is cyclophosphamide, bleomycin, etoposide, platinum agent (cisplatin), fluorouracil, vincristine, methotrexate, taxol, epirubicin, leucovorin (folinic acid), or irinotecan.

Anti-tumor immunotherapies encompassed herein (i) include monoclonal antibodies (including naked, chemo-, radio- or toxin-conjugated antibodies and also bispecific antibodies), relevant antigen-binding fragments thereof such as fragments comprised of Fab or scFv fragments, that that bind with high affinity to cancer-associated biomolecular targets; (ii) those that are non-specific with respect to tumor cells and tumor cell antigens; anti-tumor immunotherapies e.g. cytokines, interleukins, interferons, Flt3L, CD40L, GM-CSF, ligands and agonists, RIG1 helicase activators, anti-CD40, NKG2D ligand, anti-CSFIR, anti-TLR, TLR ligands, INF-α, TNF-β, anti-Tie2, small organic molecules (e.g. 1,500 daltons or less) or other drugs that bind to cytokines or cytokine receptors; and materials that target checkpoints including but not limited to one of CTLA-4, PD-1, PDL-1, and other small organic molecules, peptides and aptamers that target immune responses. In an embodiment, immunotherapy as used herein excludes bacteria-based anticancer or anti-tumor immunotherapies. In one embodiment, immunotherapy as used herein excludes *Listeria*-based immunotherapies.

In an embodiment, increasing efficacy of a treatment means an increase in the extent of therapeutic effect achieved versus the extent achieved for the same amount of treatment (e.g. a given treatment dose) in the absence of the efficacy-increasing method being applied.

Also provided is an acoustic priming therapy device comprising:
  a control system that generates a frequency waveform; and
  one or more transducers configured to produce ultrasound based on a frequency waveform between 1 and 1000 W/cm² spatial peak temporal average acoustic output intensity ($I_{spta}$) in a treatment zone, wherein ultrasound is applied continuously to the treatment zone for a time in the range of from 0.5 to 5 seconds, wherein ultrasound frequency is in the range of 0.01 to 10 MHz and wherein mechanical index of any beam is less than 4.

In an embodiment of the device, each of the one or more transducers are configured to produce ultrasonic beams based on the frequency waveform with central frequencies in the range of 0.05 to 5 MHz and an acoustic output intensity of between 20 and 1000 W/cm².

In an embodiment of the device, each of the one or more transducers are configured to produce ultrasonic beams based on the frequency waveform with central frequencies in the range of 0.5 to 1.5 MHz and an acoustic output intensity of between 20 and 1000 W/cm².

In an embodiment of the device, each transducer is configured to produce columnated ultrasound such that the beam profile waist at −3 dB is not less than 5 mm in a treatment zone.

In an embodiment of the device, one or more beams are mechanically moved during treatment.

In an embodiment of the device, the one or more transducers comprise two or more transducers configured to operate sequentially or simultaneously and produce ultrasound of average spatial peak less than 250 W/cm² in a treatment zone during a treatment period.

In an embodiment of the device, the one or more transducers are configured produce ultrasound having a frequency within the range of 10 kHz to 300 KHz.

In an embodiment of the device, the one or more transducers are configured produce ultrasound having a frequency within the range of 300 kHz to 3 MHz.

In an embodiment of the device, one or more transducers operate at a frequency of 300 kHz to 3 MHz and one or more transducers operates at a frequency of between 30 and 300 kHz In an embodiment of the device, two or more ultrasound transducers generate ultrasound beams that pass through a treatment zone, with each beam having an $I_{spta}$ in the intersection zone in the range of 10 to 500 W/cm²

In an embodiment of the device, the treatment time is less than 5 seconds per cubic centimeter of tumor.

In an embodiment of the device, two transducers generate ultrasound beams that intersect within a treatment zone, with each beam having an $I_{spta}$ in the intersection zone in the range of 50 to 500 W/cm².

In an embodiment of the device, three transducers generate ultrasound beams that pass through a treatment zone, with each beam having an $I_{spta}$ in the intersection zone in the range of 50 to 500 W/cm².

In an embodiment of the device, the one or more transducers produce ultrasonic beams that are substantially in phase with one another within the treatment zone.

In an embodiment of the device, two ultrasound beams emanating from separate ultrasound transducers are substantially in phase and intersect within a treatment zone, and each beam has an acoustic power spatial peak intensity in the intersection zone in the range of 70 to 100 W/cm² and the ultrasound is applied continuously from 1 to 5 seconds.

In an embodiment of the device, three ultrasound beams emanating from separate ultrasound transducers are substantially in phase and intersect within a treatment zone, and each beam has an acoustic power spatial peak intensity in the intersection zone in the range of 20 to 70 W/cm² and the ultrasound is applied continuously for 1 to 5 seconds.

In an embodiment of the device, ultrasonic beams originating from separate transducers each produce an $I_{spta}$ in the range of approximately 100 to 1000 W/cm² in the treatment zone.

In an embodiment of the device, at least one transducer generates an ultrasonic beam with a high intensity diameter that is substantially larger in size than the treatment zone and is directed such that the treatment zone is entirely within the beam.

In an embodiment of the device, an intense treatment zone is formed where two or more ultrasound beams cross paths, the intense treatment zone being equal to or greater than about 1 cm perpendicular to the transmitted energy direction and also equal to or greater than about 1 cm parallel to the transmitted direction.

In an embodiment of the device, acoustic pressure applied to a treatment zone from each transducer is 0.1 to 10 MPa.

In an embodiment of the device, the number of transducers that provide the intense ultrasound treatment zone is between 1 and 1000.

In an embodiment of the device, the ultrasound from the one or more transducers is applied continuously during the treatment time.

In an embodiment of the device, the ultrasound is produced with a duty cycle in the range of 1 on time units to 0 to 9 off time units.

In an embodiment of the device, the transducers are configured to produce ultrasound in single frequency tones or multi-frequency chirps.

In an embodiment of the device, the one or more transducers are operated sequentially in time.

In an embodiment of the device, the total energy delivered to the target tissue and desired margin around the target tissue for the entire course of the application is greater than that to surrounding tissues. In an embodiment of the device, the one or more transducers are configured so that the frequency of ultrasound is swept during application. In an embodiment of the device, the one or more transducers comprise two-dimensional phased arrays. In an embodiment of the device, the one or more transducers comprise annular arrays. In an embodiment of the device, the one or more transducers comprise three-dimensional phased arrays. In an embodiment of the device, the one or more transducers are incorporated into one or more endoscopic devices. In an embodiment of the device, the one or more transducers are incorporated into a magnetic resonance imaging machine. In an embodiment of the device, the one or more transducers are incorporated into a radiotherapy treatment machine.

In an embodiment of the device, the one or more transducers are configured to produce ultrasound so that the maximum temperature reached in the treatment zone is less than 45° C. during a treatment where ultrasound is applied to the treatment zone for about 2 seconds or less. In an embodiment of the device, the one or more transducers are configured to produce ultrasound so that the maximum temperature reached in the treatment zone is less than 50° C. during a treatment where ultrasound is applied to the treatment zone for about 2 seconds or less.

In an embodiment of the device, the one or more transducers are configured to produce ultrasound so that the maximum temperature reached in the treatment zone is less than 55° C. during a treatment where ultrasound is applied to the treatment zone for about 2 seconds or less.

Also provided is a system comprising:
an acoustic priming therapy device comprising:
a control system that generates a frequency waveform; and
one or more transducers configured to produce ultrasound based on a frequency waveform between 1 and 1000 W/cm$^2$ spatial peak temporal average acoustic output intensity ($I_{spta}$) in a treatment zone, wherein the ultrasound is applied continuously for a time in the range of from 0.5 to 5 seconds, and wherein ultrasound frequency is in the range of 0.01 to 10 MHz; a radiotherapy treatment machine; and a control system operatively configured to control the acoustic priming therapy device and the radiotherapy treatment machine so that a first amount of the ultrasound and a second amount of radiotherapy are administered to a subject, wherein the first and second amounts together are sufficient to treat a tumor in the subject.

Also provided is a system comprising:
an acoustic priming therapy device comprising:
a control system that generates a frequency waveform; and
one or more transducers configured to produce ultrasound based on a frequency waveform between 1 and 1000 W/cm$^2$ spatial peak temporal average acoustic output intensity ($I_{spta}$) in a treatment zone, wherein the ultrasound is applied continuously for a time in the range of from 0.5 to 5 seconds, and wherein ultrasound frequency is in the range of 0.01 to 10 MHz;
the acoustic priming therapy device for use in combination with chemotherapy so that a first amount of the ultrasound and a second amount of the chemotherapy are administered to a subject, wherein the first and second amounts together are sufficient to treat a tumor in the subject.

Also provided is a system comprising:
an acoustic priming therapy device comprising:
a control system that generates a frequency waveform; and
one or more transducers configured to produce ultrasound based on a frequency waveform between 1 and 1000 W/cm$^2$ spatial peak temporal average acoustic output intensity ($I_{spta}$) in a treatment zone, wherein the ultrasound is applied continuously for a time in the range of from 0.5 to 5 seconds, and wherein ultrasound frequency is in the range of 0.01 to 10 MHz;
the acoustic priming therapy device for use in combination with immunotherapy so that a first amount of the ultrasound and a second amount of the immunotherapy are administered to a subject, wherein the first and second amounts together are sufficient to treat a tumor in the subject.

Example 1

Figures 1A, 1B, 1C, 1D, 1E, 1F:
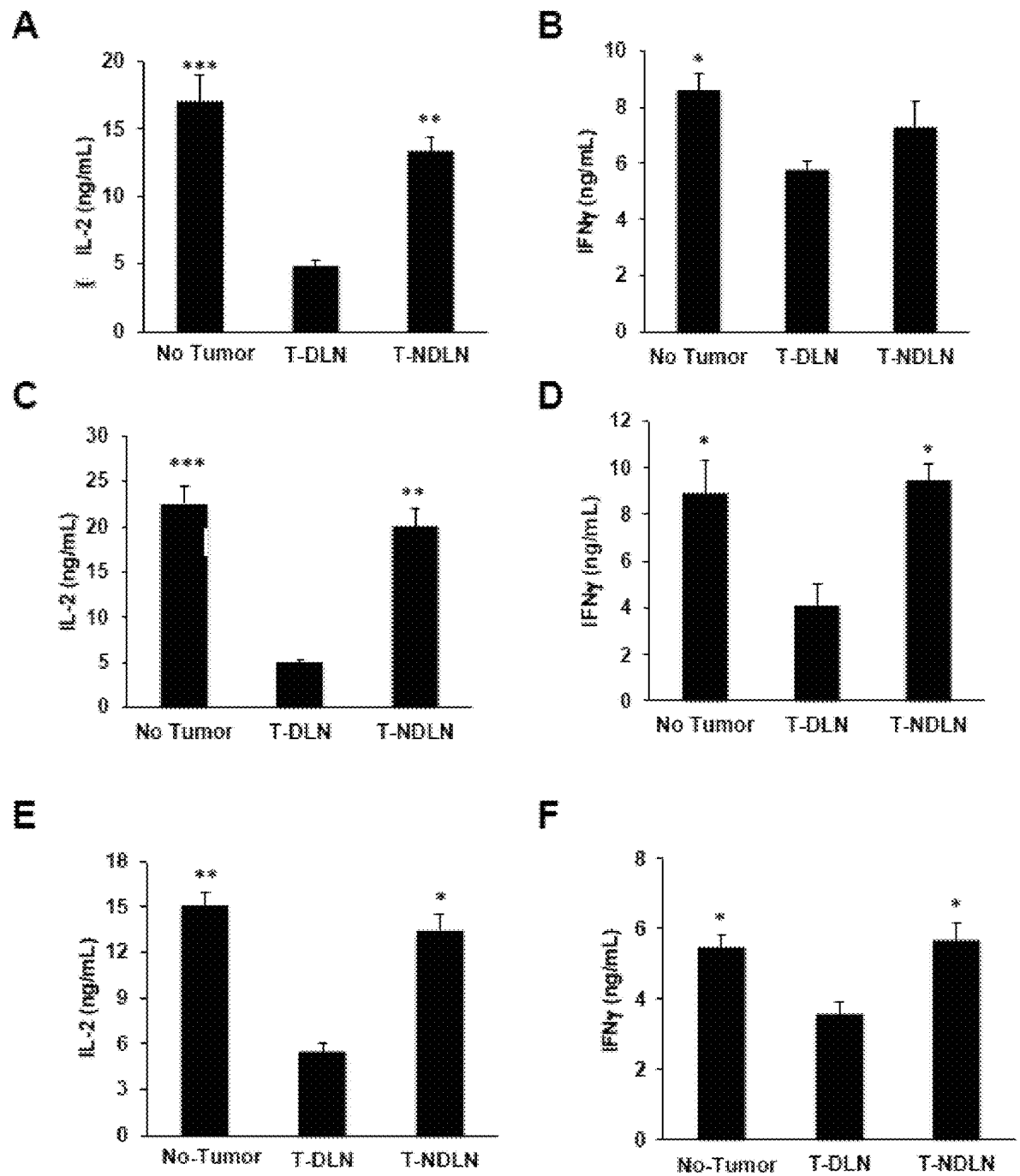
FIG. 1A-1F. Melanoma tumors suppress cytokine output of CD4+ T cells: 1A-B: C57B1/6 mice were challenged in the lumbar flanks with 3×10⁵ B16-F1 melanoma cells. Tumors were allowed to grow to 7-8 mm³ in size. CD4+ T cells were isolated from the tumor DLN and distal contralateral NDLN, and stimulated with anti-CD3 and anti-CD28 antibodies. IL-2 and IFNγ were measured by ELISA. CD4+ T cells from tumor-free mice were used as controls. 1C-D.

B16 melanoma tumors suppress IL-2 and IFNγ production by tumor-specific CD4+ T cells. To determine how melanoma cells may modulate tumor induced effector CD4+ T cell responses, three different mouse models were used. First, B16-F1 melanoma tumors were induced in C57B1/6J mice by subcutaneous injection of B16 cells in the lumbar flanks. Tumors were allowed to grow to a size of 7-8 mm and CD4+ T cells were then isolated from both the ipsilateral inguinal draining lymph nodes (DLN) and distal-contralateral non-draining cervical lymph nodes (NDLN). T cells were also obtained from control mice that did not harbor any tumors. CD4+ T cells isolated from the tumor DLN produced significantly less IL-2 than cells isolated from the distal contralateral NDLN of the same mice, or from lymph nodes of control tumor-free mice, when stimulated ex vivo with anti-CD3 and anti-CD28 antibodies. A similar but less pronounced effect was also observed for IFNγ (FIGS. 1A and B).

To confirm these data, a B16-F1 melanoma cell line that had been stably transfected to express OVA as a surrogate tumor antigen was used. These cells were subcutaneously injected into OT-II mice, a mouse strain with T cells expressing a transgenic MHC class II-restricted TCR that recognizes the OVA323-339 peptide. T cells were collected from these mice as described, and stimulated ex vivo using splenocytes loaded with OVA323-339 peptide. CD4+ T cells from the ipsilateral DLN again produced significantly reduced amounts of IL-2 and IFNγ compared to cells from the contralateral NDLN or from tumor free mice (FIGS. 1C and 1D).

These results were further corroborated in a third model using Tyrp1 mice, which are deficient in tyrosinase-related protein 1 and bear T cells expressing a MHC class II-restricted TCR specific for the TRP-1113-127 peptide of this endogenous melanocyte differentiation antigen. Those mice were injected with B16-F1 cells. As in the previous two models, IL-2 and IFNγ production by CD4+ T cells harvested from the ipsilateral DLN was significantly reduced compared to cells harvested from contralateral NDLN or from tumor-free mice. (FIGS. 1E and 1F). Altogether, these results support that melanoma tumors induce hyporesponsiveness in tumor antigen-specific CD4+ T cells, which translates in a reduced capacity to produce effector cytokines upon re-stimulation.

Figures 2A, 2B, 2C, 2D:
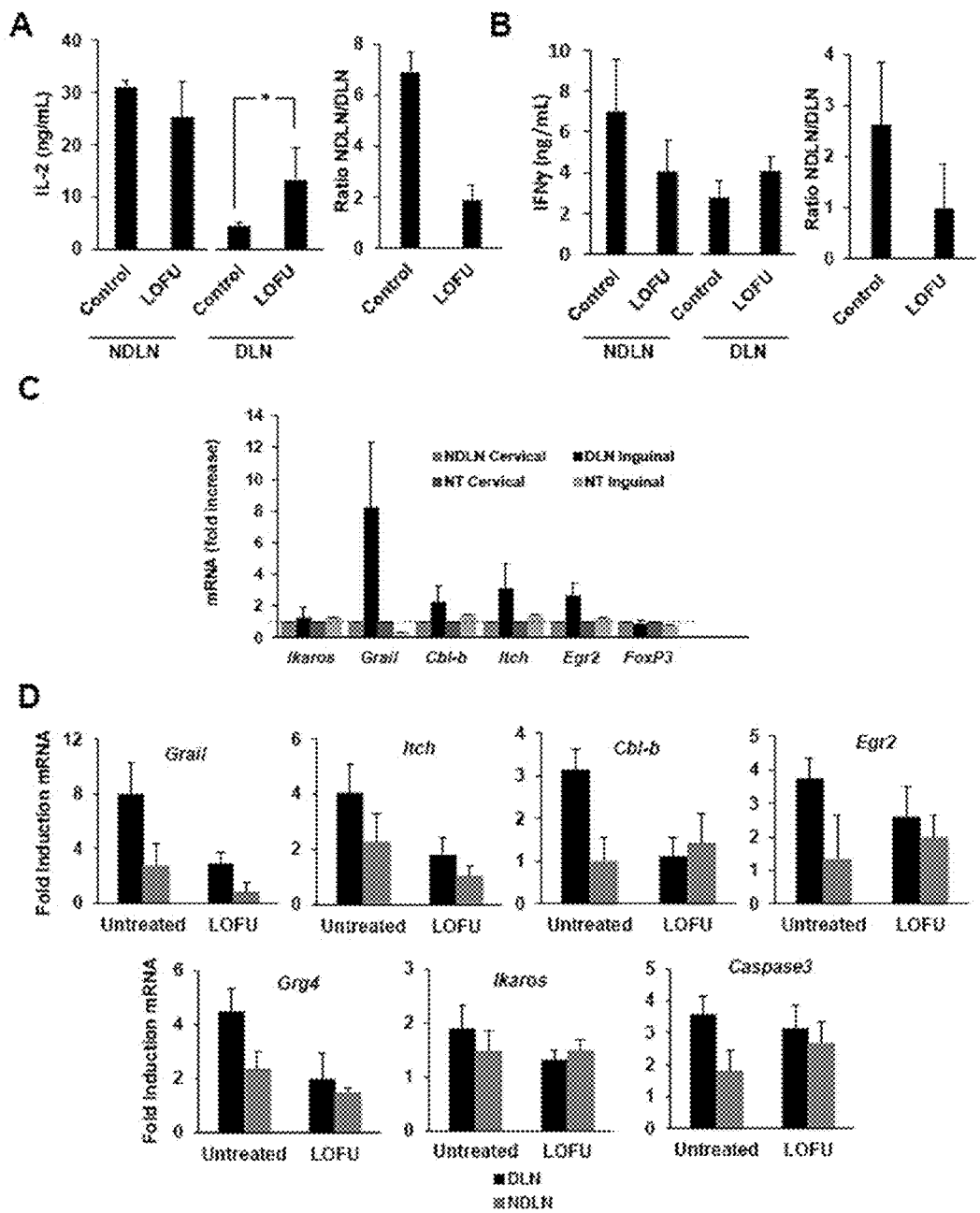

Treatment of primary B16 melanoma with LOFU overcomes tumor-induced tolerance in CD4+ T cells: HIFU is currently being used to predominantly cause tumor ablation through the generation of high amounts of heat inside the tumor tissue leading to coagulative necrosis. Although HIFU is a very effective, noninvasive ablative procedure to achieve local tumor control, it destroys the vasculature and tissue infrastructure almost instantaneously, thereby limiting the infiltration of dendritic cells and immune cells for antigen presentation and recognition. It was explored whether administering LOFU would induce a non-lethal thermal/ mechanical stress in the tumor tissue that could generate novel tumor antigens and/or induce the expression of stress-induced proteins, which could increase the immunogenicity of the tumor and overcome tumor-induced tolerance of CD4+ T cells. In order to examine this possibility, primary B16-F1 melanoma tumors grown on separate groups of C57B1/7J mice were either left untreated or treated with LOFU. Thirty six hours after LOFU treatment, DLN and NDLN resident CD4+ T cells were isolated from both groups of mice, and re-stimulated ex-vivo with antiCD3 and antiCD28 antibodies. CD4+ T cells from the DLN of the LOFU-treated mice produced significantly more IL-2 compared to the cells obtained from the group of mice bearing untreated tumors. In contrast, T cells from the corresponding NDLN produced comparable amounts of IL-2 in treated and untreated mice (FIG. 2A). A similar but less pronounced effect was observed on IFNγ production in these same experimental groups of mice (FIG. 2B). Overall, these results indicated that LOFU treatments of B16 melanoma tumors appear to bolster CD4+ T cells to overcome the hyporesponsive state induced by the melanoma tumor microenvironment, suggesting improved activation and reduced tumor-induced T cell tolerance.

Melanoma tumors can induce an NFAT1-dependent program of gene expression that produces a set of proteins which interfere with TCR signaling and directly inhibit expression of cytokines, resulting in the establishment of functional anergy in CD4+ T cells. To determine the possibility that LOFU treatment could inhibit tumor-induced T cell tolerance by preventing anergy induction and be responsible for the increased cytokine expression observed in the DLN resident CD4+ T cells following treatment with LOFU, the expression of those anergy-associated genes in CD4+ T cells isolated from the DLN of mice bearing B16 tumors was first monitored and compared with the expression of those genes in T cells harvested from NDLN of the same mice. T cells from the DLN of tumor-bearing mice expressed higher levels of anergy-associated genes, including the E3 ubiquitin ligases Grail, Cb1-b and Itch and the transcription factor Egr2 (FIG. 2C). However, no difference in the expression of Foxp3 was observed between the DLN and NDLN T cells in tumor bearing mice, suggesting that an increased presence of regulatory T cells was not likely contributing to the decreased CD4+ T cell responses under the conditions used in this study (FIG. 2C).

It was then determined if treatment of B16 melanomas with LOFU would have an effect on the expression of those anergy-associated genes in T cells. To assess responses induced by endogenous tumor antigens, B16 tumors growing on Tyrp1 mice were either left untreated or treated with LOFU. CD4+ T cells were isolated from the DLN and NDLN and the expression of several anergy-associated genes was assessed. T cells derived from the DLN showed varying degrees of upregulation of 6 of the 7 anergy genes analyzed, including Grail, Itch, and Cb1b, as well as the transcription factors Egr2 and Grg4, and the protease Caspase3 (FIG. 2D). Another transcription factor, Ikaros, which is also upregulated in several in vitro and in vivo T cell anergy models, was not significantly upregulated in this melanoma model of tumor-induced anergy, and its levels remained largely similar in both the DLN and NDLN derived T cells (FIG. 2D). Interestingly, when the tumors were treated with LOFU, the expression of 5 of those genes, Grail, Itch, Cb1b, Egr2 and Grg4 in the T cells isolated from the DLN was not upregulated and showed levels comparable to the expression of these genes in the NDLN (FIG. 2D), supporting that LOFU treatment inhibited the induction of the expression of anergy-inducing genes in tumor antigen-specific CD4+ T cells.

LOFU treated melanoma tumors are able to reactivate anergic tumor antigen-specific T cells: The results supported that tumor-induced T cell tolerance could be overcome following LOFU treatment. This observation was substantiated by the fact that the expression of several anergy-associated genes was decreased in T cells from tumor DLN following LOFU treatment of the tumor site, while activation-induced cytokine expression was restored to levels close to those detected in T cells isolated from distal NDLN or in T cells isolated from control non-tumor bearing mice.

Whether LOFU might not only prevent the induction of tumor-antigen specific T cell anergy but also reverse established anergy and generate a productive effector response in previously tolerized T cells was investigated. Naïve CD4+ T cells were isolated from spleen and lymph nodes of Tyrp1 mice, in vitro differentiated into TH1 cells and anergized by activating them through partial stimulation using with anti-CD3 antibodies in the absence of co-stimulation. T cells became hyporesponsive and showed a profound decrease in IL-2 production upon re-stimulation with anti-CD3 and anti-CD28 antibodies (FIG. 3A). These anergic cells were then re-activated with CD11c+dendritic cells loaded with lysates derived from either untreated or LOFU treated melanoma tumors. Anergic Tyrp1 T cells stimulated with dendritic cells loaded with tumor lysates from untreated B16-F1 melanoma produced negligible amounts of IL-2. However, when dendritic cells were loaded with tumor lysates prepared from LOFU-treated tumors, previously anergized T cells produced significantly more IL-2 than those activated with untreated lysates (FIG. 3B). These results indicate that LOFU treatment of melanoma tumors might result in the generation of immunogenic molecules that can enable dendritic cells to deliver activating signals that can breach tolerance, enabling otherwise anergic T cells to respond to antigen re-encounter and generate a productive response.

Figures 4A, 4B, 4C, 4D:
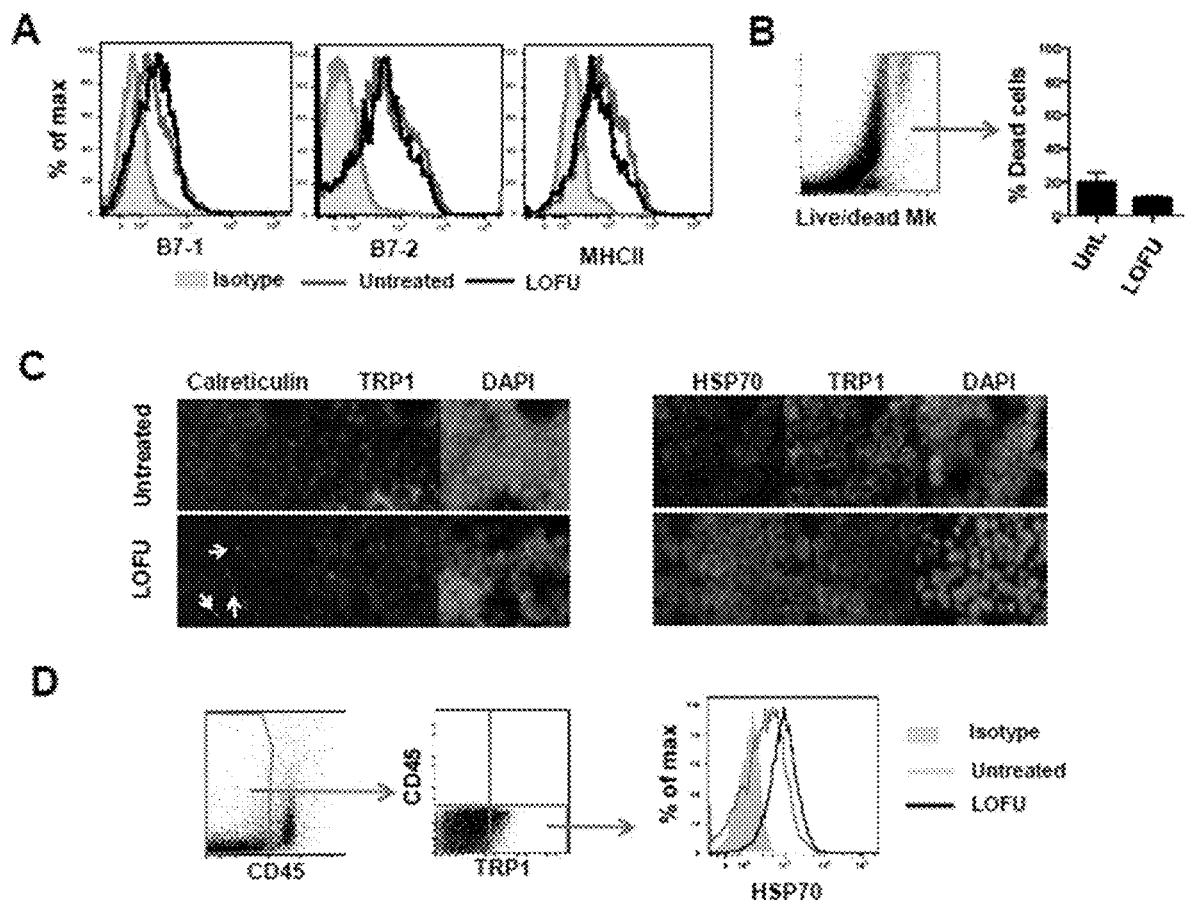

Treatment of melanoma with LOFU induces changes in the expression and subcellular distribution of the molecular chaperones calreticulin and Hsp70 in melanoma tumor cells: Activation of melanoma-specific T cells by dendritic cells is a crucial event in determining their fate. A successful antigen presentation event that is able to elicit an effector T cell response is critically dependent on the activation state of dendritic cells that would otherwise deliver tolerogenic stimuli. The results indicate that treatment of melanoma tumors with LOFU resulted in increased CD4+ T cell activation as consequence of hindering tumor-induced T cell tolerance. This could potentially result from the generation of more immunogenic dendritic cell populations. To test the effect of LOFU on the ability of dendritic cells of efficiently present antigens to T cells, total cells from the DLNs of tumor-bearing mice were first isolated, untreated or treated with LOFU, and immunostained to measure the expressions of B7.1, B7.2, and MHCII on CD11c+dendritic cell populations by flow cytometry. No significant enhancement of the expression of these proteins in the LOFU-treated mice was detected (FIG. 4A).

Trafficking of tumor antigens by molecular chaperones, including calreticulin and Hsp70, is also crucial for the subsequent productive presentation of antigens to T cells. Both in vivo and in vitro approaches were employed to detect membrane calreticulin and Hsp70 in untreated and LOFU treated B16 melanoma tumors. Tumors, either left untreated or treated with LOFU, were harvested from tumor bearing mice, made into single cell suspensions and stained with a live/dead marker to assess cell viability. No differences in cell viability were observed in response to LOFU treatment, supporting the notion that the low energy form of FUS was not directly inducing tumor cell death (FIG. 4B). B16 melanoma tumors were left untreated or exposed to LOFU treatment and tumor tissue sections were put on slides. Slides were subjected to staining with anti-Hsp70 or anti-calreticulin antibodies for a subsequent detection by immunofluorescence. Immunofluorescence analyses of LOFU treated melanomas confirmed that LOFU induced increased expression of Hsp70 (FIG. 4C). Interestingly, compared to untreated cells, LOFU treated cells also showed a change in the distribution of calreticulin, which appeared to accumulate in discrete regions of the plasma membrane on B16 cells (FIG. 4C). To determine if the increased Hsp70 expression also correlated with increased presence in the membrane of this protein, non-permeabilized CD45-TRP-1+B16 melanoma cells were stained for Hsp70 and cell surface expression following LOFU treatment assessed by FACS. This analysis confirmed that LOFU treatment of B16 melanomas caused increased membrane presence of Hsp-70 in tumor cells (FIG. 4D).

LOFU treatment of melanoma tumors potentiates dendritic cell-mediated tumor antigen presentation to elicit a stronger CD4+ T cell response: To determine the possibility that LOFU treatment of tumors could result in enhanced stimulatory capacity of resident dendritic cells, it was directly tested if lysates prepared from LOFU treated tumors could elicit enhanced priming of antigen specific T cells leading to a more robust effector response. For this experiment, B16-F1-OVA melanoma cells were used to induce tumors in C57BL/6 mice. Lysates were prepared from untreated and LOFU treated tumors. Splenic dendritic cells and responder naïve CD4+ T cells were isolated from C57BL/6 and OT-II tumor-free mice, respectively, and were co-cultured in the presence or absence of the different tumor lysates described above. Though the OVA containing tumor lysates could act as a source of tumor antigen to prime responder T cells, exogenous OVA323-339 peptide was also added to ensure uniform loading of dendritic cells with this peptide in all conditions and more accurately determine the tolerogenic or activating nature of the different tumor lysates.

Control responder OT-II T cells, upon activation with dendritic cells loaded with OVA323-339 peptide, showed a strong response with elevated levels of IL-2 production. However, lysates obtained from untreated tumors markedly inhibited OT-II responses and resulted in a profound decrease in IL-2 production, even though exogenous OVA323-339 peptide was added to the culture (FIG. 5A). Interestingly, as opposed to untreated lysates, lysates derived from LOFU treated tumors did not only have no negative effect on the responses of OT-II cells to OVA323-339 but were also able to elicit a strong activation of OT-II responder T cells even in the absence of exogenous peptide (FIG. 5A). These results extended further support the observation that LOFU treatment of B16 melanoma tumors prevents the negative effect on the T cell priming capacity of dendritic cells that normally occurs in the tumor microenvironment.

Next it was determined whether tumor DLN resident antigen presenting cells would be functionally more efficient at activating target T cells following LOFU treatment of melanoma tumors. To that effect, B16-F1 melanomas were induced on C57BL/6 mice and were either left untreated or treated with LOFU. DLN cell suspensions were depleted of T cells and used to test the capacity and DLN antigen presenting cells to activate tumor antigen specific T cells. T-cell depleted DLN cells were thus co-cultured for 24 hours with naïve Tyrp1 CD4+ T cells and lysates prepared from B16 in vitro cultures. IL-2 production was measured by ELISA to monitor responder T cell priming. Cells isolated from the DLN of LOFU treated tumor-bearing mice showed a significantly increased ability to activate Tyrp1 CD4+ T cells compared with cells isolated from untreated mice. (FIG. 5B). These data support that LOFU treatment of B16 melanoma results in the generation of antigen presenting cells that are functionally more efficient at activating tumor-antigen responder T cells.

Figures 7A, 7B, 7C, 7D:
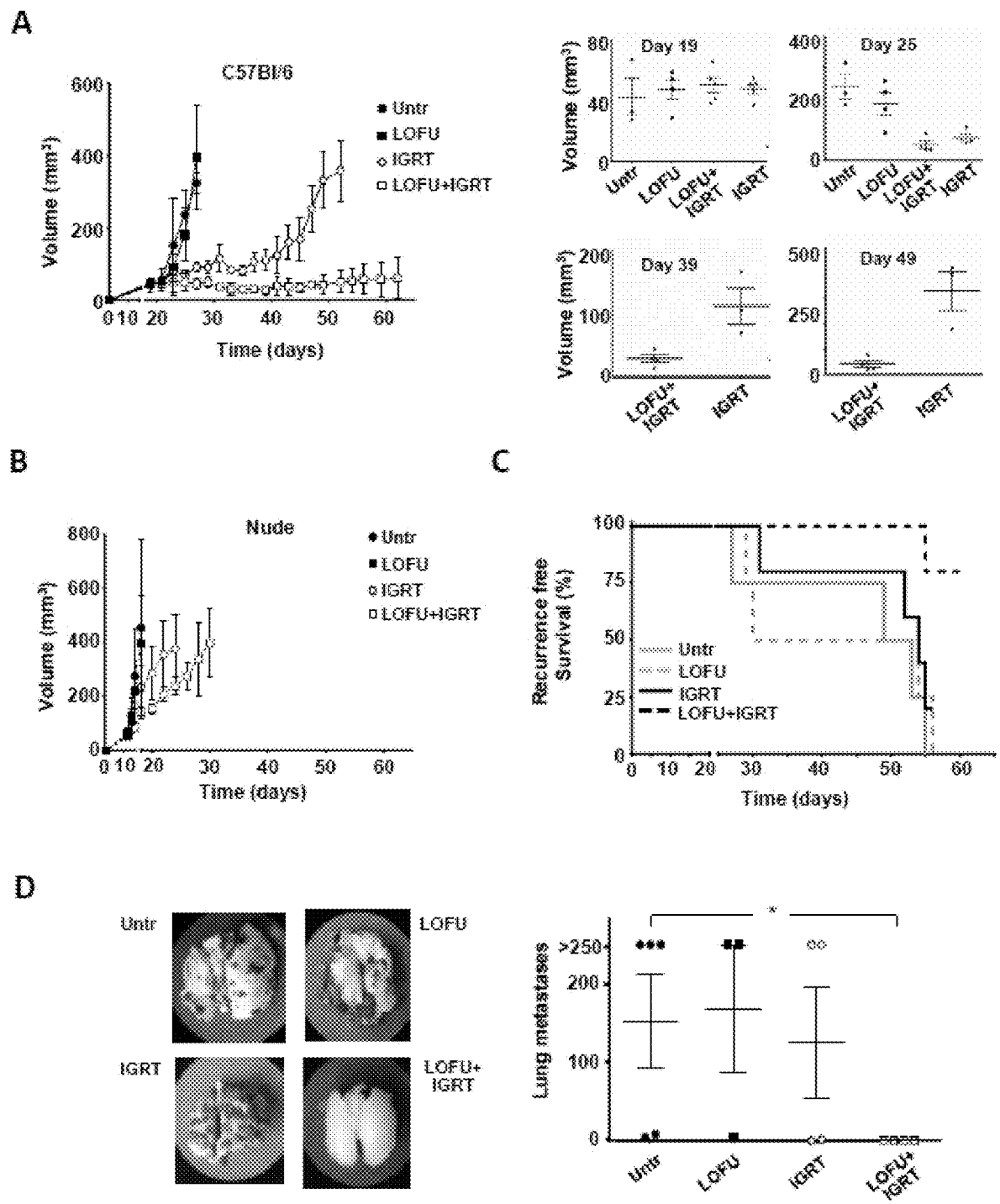

LOFU followed by ablation of tumor by hypofractionated IGRT results in enhanced T-cell mediated control of primary melanoma lesions: In order to further determine the consequences of our observation that LOFU therapy can modulate tumor immunogenicity and enhance anti-tumor immune responses, a series of in vivo treatment strategies evaluating primary tumor control were performed using a combination of LOFU with or without tumor ablation using daily 10 Gy hypofractionated IGRT to a total dose of 30 Gy per mouse with established B16-M1 tumors located subcutaneously in the right dorsal hindlimb. Treatment was initiated for all mice when tumor volume reached ~50 mm$^3$. Tumor volumes in each group were then measured three times a week for up to 62 days (FIG. 7A). Untreated C57BL/6 or mice treated with LOFU alone continued to experience rapid primary tumor growth, reaching a volume of >300 mm$^3$ within 10 days of treatment, at which point a below-the-knee amputation (BKA) was performed (FIG. 7A). In contrast, mice within the hypofractionated IGRT or LOFU+IGRT groups experienced significant growth delay for up to 3-weeks following treatment after which mice treated with IGRT alone began to exhibit primary tumor regrowth, reaching a volume≥300 mm$^3$ at approximately 5-weeks. Remarkably, the mice in the LOFU+IGRT group had a sustained response, with limited tumor growth for more than 6-weeks following treatment. The reduction in tumor volume in the group receiving LOFU+IGRT or IGRT when compared with the untreated or LOFU alone groups was statistically significant by day 25 ($P<0.05$). Moreover, the reduction in tumor volume in the LOFU+IGRT group compared with IGRT alone was statistically significant by day 35 and remained statistically significant ($P<0.05$) for the duration of the experiment. (FIG. 7A). In addition, mice in the LOFU+IGRT group demonstrated regression of tumors from their baseline measurements and a complete tumor-free response was seen in 4 out of 5 mice.

To corroborate the immunomodulatory effect of LOFU, similar experiments were performed using the immunocompromised BALB/c nude model. In these mice B16-M1 tumors grew much more rapidly, reaching≥300 mm$^3$ approximately 1-week earlier than C57BL/6 mice. The overall treatment response was similar, with untreated and LOFU alone resulting in no significant primary tumor control, while IGRT and LOFU+IGRT delayed primary tumor growth (FIG. 7B). However, in both the IGRT and LOFU+IGRT treatments, primary control was short lived. In fact, BKA was required in the IGRT group less than 2-weeks after starting treatment and in less than 3-weeks in the LOFU+IGRT group. Additionally, LOFU+IGRT in immunocompromised mice failed to result in statistically significant primary tumor control when compared to IGRT alone (FIG. 7B).

LOFU followed by hypofractionated IGRT results in prolonged recurrence free survival and reduced pulmonary metastasis: Based on the data, it was hypothesized that LOFU-induced enhanced anti-tumor T cell responses might augment therapeutic IGRT not only achieving better control of local disease, but also of microscopic disease and distant metastases. As B16-F10 is an aggressive cell line that rapidly grows to an unacceptable size if not treated, mice with primary tumors>300 mm³ required BKA. Of note, by the time a BKA was performed, cells from the primary tumor had already spread to the draining popliteal LN (data not shown). Within the subsequent weeks, the draining popliteal LN grew rapidly and became visibly enlarged, while the more distal inguinal LN became clearly palpable. When the tumors reached this point, there are no procedures that can be performed to alleviate discomfort and these mice were euthanized. Consequently, overall survival cannot be adequately assessed in mice with massive tumor burden. Therefore, it was decided to assess two other parameters: recurrence free survival, where spontaneous death or euthanized animals with excessive local recurrence tumor burden were scored as positive events; and the development of lung metastases.

The combination of LOFU+IGRT provided a statistically significant (P=0.04) recurrence free survival advantage over either treatment alone in C57BL/6 mice (FIG. 7C). Notably, in all groups except C57BL/6 LOFU+IGRT, local metastasis to the draining popliteal or inguinal LN frequently necessitated the use of euthanasia. Furthermore, while mice that were treated with LOFU+IGRT showed a strict control of lung metastases, in the other three groups, even animals with relatively little local recurrence ultimately died due to overwhelming lung metastasis (FIG. 7D).

Mice: 6-8 week old C57BL/6, B6. Cg-Rag1 tm1MomTyrp1B-wTg(TcraTcrb)9Rest/J (Tyrp1) and B6.Cg-Tg(TcraTcrb)425Cbn/J (OT-II) mouse strains were purchased from The Jackson Laboratory. BALBc/Nude mice were obtained from National Cancer Institute, distributed through Charles River. All mice were housed and maintained in pathogen-free facilities.

Culture of B16 cell lines and primary CD4+ T cells: B16-F1 and B16-F10 melanoma cell lines were purchased from the American Type Culture Collection (ATCC). A highly aggressive subclone of B16-F10 (B16-M1) was generated by isolating and expanding a metastatic clone that arose in a C57BL/6 mouse 6 weeks after surgical removal of an established primary tumor. The B16-OVA melanoma cell line was kindly provided by E. M. Lord (University of Rochester Medical Center, Rochester, NY). The expression of OVA by B16-OVA cells was confirmed by real time PCR. All melanoma cells were cultured in DMEM (Thermo Scientific) supplemented with 10% heat inactivated FBS, 2 mM L-Glutamine and 250 IU of penicillin/streptomycin.

CD4+ T cells were isolated using anti-CD4 conjugated magnetic Dynabeads (Life Technologies) according to the manufacturer's protocol. Where indicated, CD4+ T cells were differentiated into TH1 helper cells by activation with plate-bound anti-CD32 (clone 2C11; 0.25 [g/mL) and anti-CD28 (clone 37.51; 0.25 [g/mL) antibodies (BD Biosciences) and cultured for six days in DMEM supplemented with 10% heat inactivated FBS, 2 mM L-glutamine, 50 [M 2-mercaptoethanol, nonessential amino acids and essential vitamins (Cambrex), in the presence of murine IL-12 (10 ng/mL) (eBioscience), anti-mouse IL-4 antibody (clone 11C.11; 10 μg/ml) and 10 U/mL recombinant human IL-2 (Biological Resources Branch of the National Cancer Institute).

Tumor models: $3\times10^5$ B16-F1 melanoma cells suspended in Hanks' Balanced Salt Solution (Invitrogen) were injected s.c. in the lumbar flanks of mice. Melanoma tumors were induced in the footpads by injecting $2\times10^5$ B16-M1 cells in the dorsum of the right hind limb.

Tumor growth monitoring: Primary B16-M1 melanoma dorsal hind limb tumors were measured three times per week with vernier calipers. Tumor volume was calculated using an ellipsoid formula: $V=(\pi/6\times length\times width\times height)$. Primary dorsal hind limb tumors exhibit Gompertzian growth, with a phase I volume of 30-50 mm³, phase II volume of 90-150 mm³, and phase III volume of 300-500 mm³. Therefore, treatment efficacy was determined by determining the tumor growth delay (TGD) to 90-150 mm³, in which the tumor is in the exponential phase II. Tumors that reach 300-500 mm³ begin to enter phase III due to anatomical and vascular limitations. Consequently, below-the-knee amputations were performed on mice with tumors≥300-500 mm³, in accordance with IACUC approved protocol.

ELISA: 1.5 to 2.5×104 T cells were left rested or stimulated with either anti-CD3+anti-CD28 antibodies, T cell depleted OVA peptide 323-339 (OVA323-339)-loaded splenocytes at a 1:5 T cell:splenocyte ratio, or CD11c+purified dendritic cells (using CD11c-beads; Miltenyi Biotech) loaded with OVA323-339 or melanoma tumor lysates at a 1:3 dendritic cell:T cell ratio. Culture supernatants were typically harvested 24 hours after stimulation, and IL-2 or IFNlevels were measured by a sandwich ELISA (BD Biosciences).

Tumor lysates: Tumors were resected from tumor bearing mice, cut into 1-2 mm pieces and passed through 40 [m nylon meshes. Cells were washed in PBS and resuspended in serum-free DMEM. Cell suspensions were then snap frozen in liquid nitrogen, and thawed at 37° C. for five cycles with visual confirmation of complete lysis by light microscopy. The lysates were spun at 10,000g for 15 minutes at 4° C., and the pellets with cellular debris were discarded. The supernatant was used along with purified dendritic cells to stimulate T cells.

Immunofluorescence staining tumor tissue was isolated, washed in PBS and embedded in OCT compound (Electron Microscopy Sciences). Tissue sections (Sum) were prepared and permeabilized with acetone for 5 min and incubated with goat serum for 30 min to block non-specific protein-protein interactions. Tissue sections were incubated overnight with the following antibodies: anti-Calreticulin (Pierce, PAS-25922), anti-Trp1 (Abcam, ab3312; clone TA99) and anti-Hsp70 (Novus Biologicals, NBP1-77455). Appropriate secondary antibodies were used for 30 min at room temperature. DAPI (Invitrogen) was used to detect nuclei. At least 10 fields/sample were blindly analyzed with an Inverted Olympus IX81 fluorescence microscope.

Focused ultrasound therapy system. A therapy and imaging probe system (TIPS, Philips Research North America, Briarcliff Manor, NY, USA) was utilized for all ultrasound exposures. The system is capable of delivering focused and spatiotemporally controlled ultrasound energy and consists of a therapy control workstation, RF generators and control electronics, an 8-element spherical shell annular array ultrasound transducer (80 mm radius of curvature, 80 mm aperture), as well as a motion stage to allow for in-plane transducer movement and accurate positioning perpendicular to ultrasound beam axis. The focused ultrasound beam can also be steered approximately +15 mm out-of-plane using electronic deflection of the focal point. The ultrasound beam propagates vertically into the target through a thin (25 pm) circular plastic membrane, with acoustic coupling provided by degassed water. During therapy, the system allows adjustments of acoustic output power, ultrasound exposure duration, duty cycle, and ultrasound frequency.

In vivo focused ultrasound (FUS) therapy. Mice were anesthetized with a continuous flow 1.5 liters/minute of 1.5% isoflurane in pure oxygen. To ensure proper acoustic coupling, the tumor-bearing leg or lumbar flank were carefully shaved. Once the animal was positioned for therapy, the tumor was acoustically coupled to the TIPS system using degassed water and ultrasound gel. The center of the tumor was then placed at the focal length of 80 mm from the transducer. Ultrasound exposures were delivered to the tumor using a 1 mm grid pattern extending over the entire tumor volume. Two layers of grid points (spaced 5 mm apart) were performed in each tumor, resulting in approximately 160 discrete foci and 5 min exposure duration per tumor. The ultrasound transducer was operated at 1.0 MHz, resulting in an ellipsoid focal spot approximately 1.5 mm in diameter and 12 mm in length (−6 dB of pressure), as measured along the ellipsoid axes. Ultrasound exposures were delivered to the tumor using a 1 mm grid pattern extending over the entire tumor volume. Prior to therapy, the tumor volume was measured to calculate the grid size for the particular treatment. The duration of ultrasound exposure at each grid point was 1.5 s, after which the transducer was automatically positioned over the next grid point and the procedure repeated until the entire tumor volume was covered. Two layers of grid points were performed in each tumor. The therapeutic ultrasound device was operated in continuous wave mode at a specific acoustic power/pressure regimen: acoustic power 3 W, peak negative pressure-2.93 MPa (80 mm focal length)/3.81 MPa (85 mm focal length); to provide non-ablative low-energy FUS (LOFU). The resulting in situ intensity ($I_{spta}$) at the focus was estimated to be 550 W/cm$^2$ at a depth of 4 mm in tissue. Total energy deposition to a tumor was approximately 900 J.

In vivo hypofractionated cone beam CT image-guided Radiation Therapy (IGRT): All radiation was delivered using Xstrahl Limited's Small Animal Radiation Research Platform (SARRP) to deliver a 10 Gy dose to a target tumor in 341 seconds. Anesthetized animals were placed on stage attached to a motorized platform and the tumor-bearing right hind limb was extended, elevated, and secured to a 1.5 cm adhesive platform to minimize extraneous tissue exposure. Once secure, a cone beam CT (CBCT) was performed and the data opened in 3D Slicer for tissue segmentation and treatment planning. 10 Gy each was delivered for three successive days for a total hypofractionated dose of 30 Gy. In the combination therapy groups, LOFU was performed 2-4 hours prior to CBCT.

Pulmonary Metastasis Evaluation: Lungs were isolated from animals that died spontaneously, were euthanized or were sacrificed at the end of the 8-week experiment. 1 mL of Fekete's solution (Ethanol, Glacial acetic acid and formaldehyde based bleaching fixative) was injected to insufflate the lungs. The trachea was then clamped, and the entire lungs and heart removed en bloc and washed with PBS. The lungs were then placed in Fekete's solution and allowed to bleach for 48 hours prior to analysis. The left lung and the 4 lobes of the right lung were isolated and nodules counted with the aid of a dissecting microscope. Indistinct or fused nodules cannot be reliably enumerated; therefore, the lung was labeled as too numerous to account and assigned an arbitrary metastasis count of 250. Statistical analysis was performed using the non-parametric Kruskal-Wallis test, followed by the Dunn's posttest for multiple comparisons.

Recurrence Free Survival: The following events were scored as positive events in our recurrence free survival analysis: spontaneous death with necropsy validation of tumor involvement, euthanasia due to extensive local metastasis to the draining popliteal or inguinal lymph nodes, or euthanasia due to moribund appearance indicating extensive systemic tumor burden. The following non-tumor-dependent deaths were processed as censored data: death within 24-48 hours of amputation or sacrifice of any animals at the end of the 8-week experiment. In order to prevent selective sacrifice of control or treated animals, cages were labeled using an alphanumeric code such that animal institute veterinarians were blinded from treatment and control groups. Recurrence free survival was analyzed using a Mantel-Cox test, with statistical significance defined as P<0.05.

Real time PCR: Total RNA was extracted from cells using RNeasy Micro kit (Qiagen), and cDNA was synthesized using qScript cDNA supermix (Quanta Biosciences). The cDNA samples were subjected to real time PCR using PowerSYBR (Applied Biosystems) as the reporter dye on a StepOnePlus real time PCR system (Applied Biosystems). Expression of the transcripts studied was normalized to beta actin. The primer sets used are the following:

```
actinb:
                                  (SEQ ID NO: 1)
     F-GTGACGTTGACATCCGTAAAGA, (SEQ ID NO: 2)
     R-GCCGGACTCATCGTACTCC;

Cblb:
                                  (SEQ ID NO: 3)
     F-GCAGCATCATTGACCCTTTCA, (SEQ ID NO: 4)
     R-ATGTGACTGGTGAGTTCTGCC;

Grail:
                                  (SEQ ID NO: 5)
     F-ATGCAAGAGCTCAAAGCAGGAAGC, (SEQ ID NO: 6)
     R-GTGCGCAGCTGAAGCTTTCCAATA;

Ikaros:
                                  (SEQ ID NO: 7)
     F-GCTGGCTCTCGGAGGAG, (SEQ ID NO: 8)
     R-CGCACTTGTACACCTTCAGC;

Caspase3:
                                  (SEQ ID NO: 9)
     F-ACGCGCACAAGCTAGAATTT, (SEQ ID NO: 10)
     R-CTTTGCGTGGAAAGTGGAGT;

Egr2:
                                  (SEQ ID NO: 11)
     F-TCAGTGGTTTTATGCACCAGC, (SEQ ID NO: 12)
     R-GAAGCTACTCGGATACGGGAG;

Grg4:
                                  (SEQ ID NO: 13)
     F-TCACTCAAGTTTGCCCACTG, (SEQ ID NO: 14)
     R-CACAGCTAAGCACCGATGAG;

Itch:
                                  (SEQ ID NO: 15)
     F-GTGTGGAGTCACCAGACCCT, (SEQ ID NO: 16)
     R-GCTTCTACTTGCAGCCCATC;
```

-continued

Foxp3:
F-GGCCCTTCTCCAGGACAGA; (SEQ ID NO: 17)
R-GCTGATCATGGCTGGGTTGT. (SEQ ID NO: 18)

Flow cytometry: Cells were pre-blocked with Fc block (CD16/CD32) antibody prior to immunostaining. The following fluorochrome conjugated antibodies were used: anti-B7.1, B7.2, CD11c, MHC-II, CD45, as well as their respective isotype control antibodies (eBiosciences); anti-Hsp70 (Novus Biologicals) and anti-TRP1 (Abcam). Dead cells were detected by using a UV LIVE/DEAD® Fixable Dead Cell Stain Kit (Invitrogen). The immunostained cells were analyzed on an LSR-II Flow Cytometer (Becton Dickinson), and post-acquisition analyses were carried out using the FlowJo software.

Example 2

The hypoxic tumor microenvironment generates oxidative Endoplasmic Reticulum (ER) stress, resulting in protein misfolding and unfolded protein response (UPR). UPR induces several molecular chaperones including heat-shock protein 90 (HSP90), which corrects protein misfolding and improves survival of cancer cells and resistance to tumoricidal therapy although prolonged activation of UPR induces cell death. The HSP90 inhibitor, 17AAG, has shown promise against various solid tumors, including prostate cancer (PC). However, therapeutic doses of 17AAG elicit systemic toxicity. Herein a new paradigm is disclosed where the combination therapy of a non-ablative and non-invasive low energy focused ultrasound (LOFU) and a non-toxic, low dose 17AAG causes synthetic lethality and significant tumoricidal effects in mouse and human PC xenografts. LOFU induces ER stress and UPR in tumor cells without inducing cell death. Treatment with a non-toxic dose of 17AAG further increased ER stress in LOFU treated PC and switched UPR from a cytoprotective to an apoptotic response in tumors resulting in significant induction of apoptosis and tumor growth retardation. LOFU-induced ER stress makes the ultrasound-treated tumors more susceptible to chemotherapeutic agents, such as 17AAG. LOFU-induced chemosensitization is a novel therapy that can be used on tumors, for example, locally advanced and recurrent tumors.

Treatment schema and toxicity of LOFU and 17AAG therapy: For each grid location, LOFU was administered for 1.5 seconds at 100% duty cycle, acoustic power of 3 W, and using ultrasound frequency of 1 MHz. This protocol yielded an approximate in situ spatial-peak temporal-average acoustic intensity of 270 W/cm$^2$, resulting in estimated average infra-tumoral temperature elevation of 3.2° C. Post-treatment, there were no signs of normal tissue toxicity such as alopecia, thermal damage, or skin wounds. Preclinical pharmacokinetic studies in mice have shown 17AAG to be widely distributed and to undergo extensive hepatic metabolism. Systemic administration of 17AAG is known to be associated with significant hepatotoxicity, characterized by increases in transaminases and bile acids, and drug-related histopathologic lesions in the gallbladder, common bile duct, and gastrointestinal tract. Therefore, we determined the dose of 17AAG that was nontoxic for our therapy. C57Bl/6 mice were treated with intraperitoneal injections of 17AAG (25-75 mg/kg body weight) three times a week. Control mice were injected with equal volume of the vehicle DMSO, which was used to solubilize 17AAG. Although higher doses of 17AAG (50-75 mg/kg of body weight) treatment achieved significant tumor growth retardation compared to untreated control (untreated tumor, 1879±98.65 mm$^3$ versus 17AAG 75 mg/kg b.w., 485±24.25 mm$^3$, $p<0.003$ and 50 mg/kg b.w., 964 mm$^3$, $p<0.007$, respectively), Kaplan Meier survival analysis showed death in 50% of mice after 21 days of treatment with a dose of 75 mg/kg of body weight.

A low dose of 17AAG that was found to be nontoxic was 25 mg/kg in C57Bl/6 mice and 14 mg/kg in Balb/c nude mice. Thus, these dose levels were selected for the current study. The goal was to combine two therapies that are nontoxic, albeit subtherapeutic, and examine whether the combination can be therapeutic. Combination treatment of LOFU+17AAG amplifies ER stress: Accumulation of misfolded proteins in the ER induces a stress response with induction of chaperone proteins that help in correction of protein misfolding. To detect the level of ER stress, the expression levels of ER chaperones, ERp44, ERp57, and ERp72 were quantitated among different treatment groups. ERp44 is responsible for oxidative protein folding. ERp57 is an ER resident thiol disulfide oxidoreductase while Erp72 is a disulfide isomerase. All these proteins participate in the protein folding machinery of the ER. Compared to tumor tissues from animals that received no treatment or LOFU or 17AAG alone, immunoblot analysis demonstrated a significant increase in the expression of ERp78 ($p<0.03$, FIGS. 9D & 9E), ERp44 ($p<0.05$, FIGS. 9D & 9G), and ERp57 ($p<0.04$, FIGS. 9D & 9F) protein levels in tumor tissues following combination treatment with LOFU+17AAG. This suggests that 17AAG mediated inhibition of HSP90 may increase the unfolded protein burden in the ER, thereby prolonging ER stress.

Figures 10A, 10B, 10C, 10D, 10E:
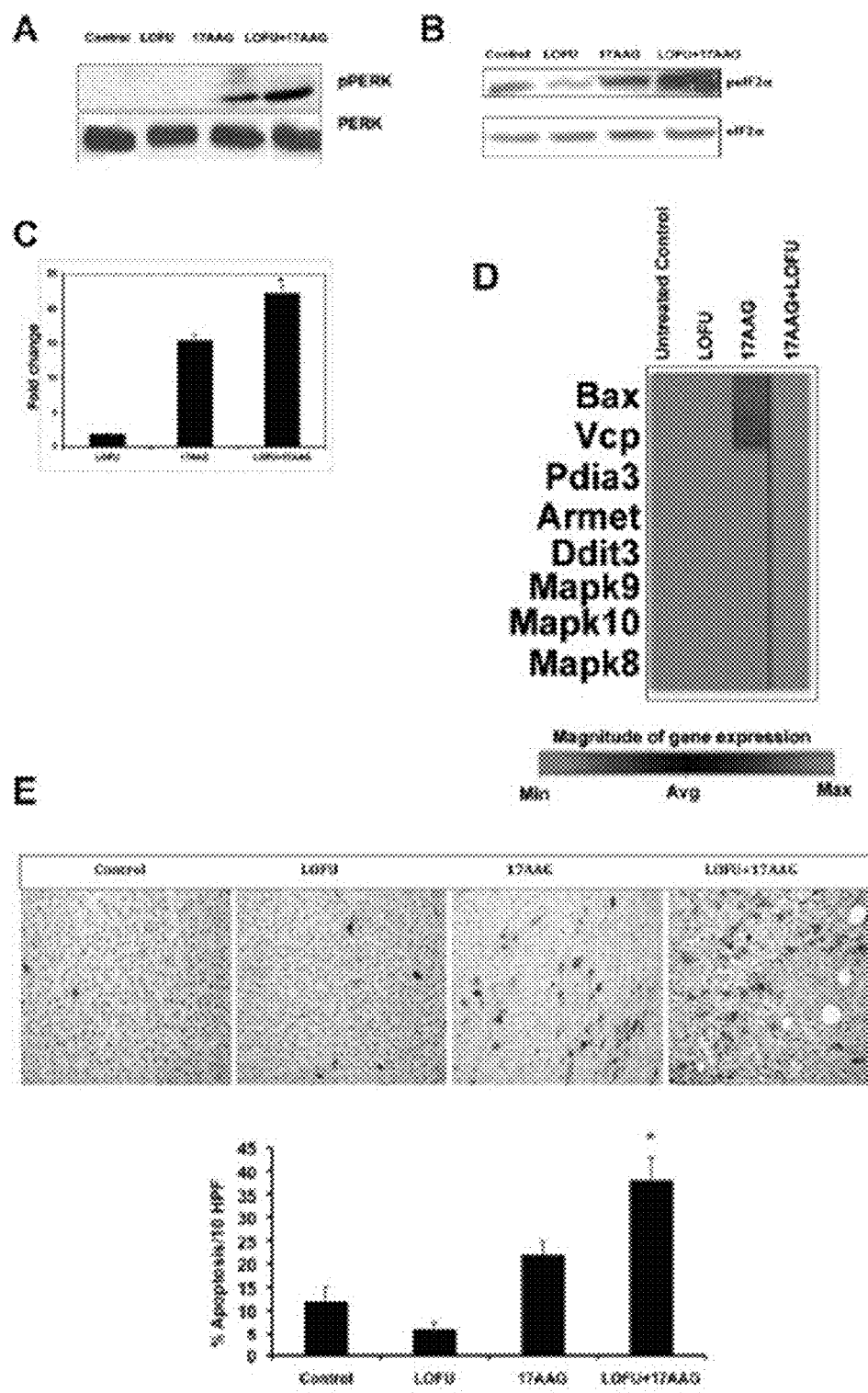

LOFU+17AAG activates pro-apoptotic pathways of UPR and induces apoptosis in mouse and human prostate cancer tissues: ER stress activates the three arms of UPR at the same time, thereby producing antagonistic cytoprotective and apoptotic signals at the same time. The fate of the cell depends upon the ability of its protein correction machinery to lower the ER stress, thereby attenuating the UPR. If ER stress persists, the cytoprotective pathways are eventually overwhelmed with the chronic activation of PERK-mediated apoptotic pathways causing cellular demise. Since phosphorylation of PERK at Thr980 serves as a marker for its activation status, we performed immunoblot analysis that showed a significant increase in pPERK levels in tumor tissue following treatment with 17AAG (FIG. 10A). Phosphoiyiated PERK levels were absent in untreated and LOFU-treated tumors. However, combination treatment of LOFU+17AAG exhibited the highest levels of PERK phosphorylation (FIG. 10A).

Since prolonged PERK activation attenuates protein synthesis in response to ER stress through the phosphorylation of translation initiation factor eII:2a at serine 51, the levels of phosphorylated eIF2α were determined. Treatment of RM1 tumors with 17AAG induced phosphorylation of eIF2α over the basal levels in untreated controls. LOFU treatment resulted in marginal reduction of phosphorylated eIF2α levels. However, the highest levels of phosphorylated eIF2α were seen in tumors that received combination treatment with LOFU+17AAG (FIG. 10B), corroborating with highest activation of PERK phosphorylation in these tumors compared to other groups.

Although phosphorylated eIF2a decreases the translation of most cellular proteins, including pro-survival and anti-apoptotic proteins, it increases the translation of a transcription factor, ATF4 that is responsible for inducing the transcription of pro-apoptotic genes, such as, CCAAT/enhancer-binding protein homologous protein (CHOP), thereby preparing the cell for programmed cell death in case the misfolded proteins are not repaired and ER stress persists. LOFU treatment failed to induce CHOP levels (1.6±0.7 fold) over untreated controls. In contrast, treatment with 17AAG alone induced CHOP transcript levels to 14.8±2 fold, which was further increased to 25±1.3 fold (p<0.006) in the combination treatment group of LOFU+17AAG, compared to untreated controls (FIG. 10C).

In order to examine whether downstream apoptotic genes are expressed following CHOP induction by the combination therapy of LOFU+17AAG, a mouse UPR qRT-PCR Array was used on total RNA isolated from tumor tissues of various treatment groups. Heatmap analysis demonstrated that pro-apoptotic target genes, such as Bax, Vcp, Pdia3, Armet, Ddit3, Mapk8, Mapk9, and Mapk10 were induced several folds following combination therapy with LOFU+17AAG compared to untreated controls (FIG. 10D). There was minimal induction of pro-apoptotic genes upon treatment with LOFU alone or 17AAG alone. This result indicates that the combination therapy of LOFU+17AAG activates PERK, induces CHOP, and switches on the pro-apoptotic pathway of the UPR. Indeed, TUNEL staining demonstrated that LOFU induced minimal apoptosis over untreated controls. Treatment with 17AAG induced significant apoptosis in prostate tumors, which was further increased by LOFU (p<0.004) (FIG. 8E). Thus, 17AAG-mediated inhibition of HSP90 and activation of CHOP by the combination of LOFU+17AAG switched on apoptotic cell death of prostate tumors. LOFU+17AAG inhibits Chaperone Mediated Autophagy (CMA) in tumor cells.

Degradation of misfolded proteins is mediated by the proteosomal pathway and autophagy. Autophagy has been implicated in the tumorigenesis process in a context-dependent role, where it might provide amino acids and other essential nutrients to the metabolic pathways of hypoxic tumors that are nutrient deprived. Indeed, an increase in CMA activity has been described in a wide variety of human tumors and CMA has been implicated in survival, proliferation, and metastases of tumor cells. Therefore, the levels of two key proteins participating in autophagy were quantitated, Beclin, a marker of macroautophagy, and LAMP-2A lysosomal receptor, a marker of CMA in the tumor tissues of various treatment cohorts. As shown in FIG. 10, Beclin levels remain unchanged with LOFU or 17AAG or the combination therapy (FIGS. 9A & 9C), indicating that macroautophagy was not altered with ultrasound therapy. However, LOFU alone or 17AAG alone induced the expression of LAMP-2A (FIGS. 11A & 11B), indicating a compensatory increase in CMA after therapies that increase the burden of misfolded proteins in the ER. Interestingly, the combination of LOFU+17AAG inhibited the levels of LAMP-2A below the basal levels seen in these tumors. This suggests that the combination therapy reduces the growth of tumor cells and induces apoptosis by increasing ER stress while suppressing CMA.

LOFU sensitizes human and murine prostate cancer grafts to non-toxic low doses of 17AAG: Treatment with LOFU alone or low dose of 17AAG (25 mg/kg body weight) alone did not show any normal tissue toxic effect but failed to inhibit tumor growth. However, combination therapy of LOFU+17AAG reduced the growth of murine RM1 tumors (FIG. 10B). The average estimated tumor growth is 5% (p<0.0001), 9% (p<0.0001) and 11% (p<0.0001) slower in LOFU, 17AAG and LOFU+17AAG cohort compared to control group. The median time to achieve tumor size 2000 mm$^3$ in control, LOFU, and LOFU+17AAG were 18, 22, and 42 days, respectively. All the animals in 17AAG group achieved the size within the interval of 26-30 days.

A similar degree of chemosensitization was observed in human PC3 tumors in BalbC nu/nu mice upon application of LOFU together with low non-toxic dose of 17AAG (14 mg/kg of body weight), achieving significant tumor growth retardation (p<0.007) (FIG. 5C) without any immediate adverse side effects.

LOFU+17AAG treatment reduces the prostate cancer stem cell population in tumor tissue: The effect of LOFU+17AAG-induced ER stress on PC stem/progenitor population was evaluated by flow cytometric analysis of PC stem/progenitor cell surface markers. The percentage of cells expressing cell surface SCA1 (FIGS. 13A & 13B) (p<0.004), CD44 (FIGS. 13A & 13C) (p<0.003), CD133 (FIGS. 13A & 13D) (p<0.007), and a2β1 integrin (p<0.005) (FIGS. 11A & 11E) was significantly decreased in the combination treatment group, compared to control or single treatment cohort. Mean fluorescence intensity (MF1) of all these markers remained unaltered in all the three groups. qRT-PCR array of stem cell transcription factors demonstrated increase (>2 folds) in mRNA levels of TIx3, Hoxall, Pena, Gli2, Runx1, Foxa2, Sp1, Tbx5, HoxalO, Nfatcl, Gata6, and Notch2 (FIG. 13F), indicating that LOFU induces a PC stem cell transcription signaling. Treatment with 17AAG also increased the expression of some transcription factor MRNAs, such as FoxPI, Nrf2f, and Pou5fl that were present in LOFU-treated tumors. However, tumor treated with LOFU+17AAG down-regulated the expression of these genes, suggesting that maximization of ER stress by the combination treatment might reduce the PC stem/progenitor cell population in tumors.

The results demonstrate That the LOFU and chemotherapy combination therapy reprograms the expression of pro-apoptotic genes in tumors and induces massive apoptosis in tumor xenografts, resulting in significant tumor growth retardation of mouse and human PC tumors. In some embodiments, LOFU can ameliorate resistance to a chemotherapy, and chemosensitization can be effected.

Animals: Five- to six weeks-old male C57Bl/6 (NCI-Fort Dietrich, MD, USA) mice and athymic nude (BalbC nu/nu mice, Jackson Laboratory, Bay Harbor, ME, USA) mice were maintained ad libitum and all studies were performed under the guidelines and protocols of the Institutional Animal Care and Use Committee of the Albert Einstein College of Medicine.

Tumor model and treatment; C57BI/6 and BalbC nu/nu mice were injected subcutaneously with 1×10$^5$ RM-1 (murine prostate cancer cell line) and 1×106 PC3 (human prostate cancer cell line) cells on the flank, respectively. Approximately 10 days later, the tumor became palpable (3-5 mm in diameter), whereupon LOFU treatment was initiated. Mice were divided into 4 groups (n=5/group) receiving no treatment, LOFU, 17AAG (InvivoGen, San Diego, CA, USA), and 17AAG+LOFU. Palpable tumors were treated with LOFU every 3-4 days for five fractions administered over two weeks. Animals received 17AAG three times a week during this time. Tumor volume measurements were performed twice weekly using Vernier calipers along with simultaneous physical assessment of signs of systemic toxicity (malaise and diarrhea).

Example 3

Ablative procedures, such as High-Intensity Focused Ultrasound (HIFU), radio frequency ablation (RFA) and cryotherapy, have the potential to release tumor-derived proteins that could potentially be available for antigen uptake by dendritic cells (DC) and other professional antigen presenting cells (APC) of the immune system. Clinical HIFU uses high temperatures at the focal point that approach 95-100° C. within minutes, which kills the tumor cells instantly and destroys the tissue architecture and the vascular system. This may impede the infiltration of immune cells in the HIFU-treated tumor. The tumor cells have no time to react to the thermal stress and induce stress proteins, such as HSPs for immune activation. Although, HIFU-induced coagulative necrosis can release a large amount of denatured tumoral proteins, there is potential for the induction of antigenic tolerance from antigen load and the denatured cellular proteins would need further antigen processing and cross-presentation by DCs for T cell activation. Pretreatment of tumors with low energy focused ultrasound (LOFU) that induce sonic stress by raising the temperature to 42-45° C. without killing the cells could result in cytoplasmic protein unfolding, endoplasmic reticulum (ER) stress and an increase in the expression of molecular chaperones, such as heat shock proteins (HSPs). The antigen processing machinery would eventually process the misfolded proteins as antigenic peptides to be presented on cell surface MHC for T cell recognition. Subsequent exposure of the LOFU-treated tumors to HIFU, 1-2 days later, could induce tumor cell death and the release of HSP-tumor peptide complex into the extracellular compartment and into the blood stream, resulting in an autologous in situ tumor vaccination. Thus, a sequential administration of LOFU and HIFU would provide a source of tumor antigens and endogenous "danger" signals for DC activation, thereby inducing a tumor-specific systemic immune response that would augment the efficacy of therapeutic ultrasound to control both local and systemic disease.

Three human prostate cancer cell lines, DU145, PC3, and LNCap, and two murine prostate cancer lines, RM-1 and Tramp-Cland murine mouse model were tested for the efficacy of HIFU and LOFU combination therapy. Induction of HSP was measured with ELISA, immunofluorescent staining, and flow cytometry. Cellular proliferation and number were determined by ELISPOT assay.

Pretreatment with non-ablative LOFU could enable the tumor cells to process misfolded. proteins and subsequent treatment with HIFU, a day later, would allow the release of Hsp-peptide complexes from dying tumor cells for DC uptake and induction of T cell immunity. Palpable OVA-expressing RM1-OT tumors were treated sequentially with LOFU, followed by HIFU, one day apart and animals were sacrificed on days 3, 7 and 14 post-LOFU treatment. While, no tumor-specific T cell response was detected with one cycle of LOFU and HIFU treatment, there was a modest increase in the total number of IFN-γ-producing cells (stimulated by PMA and Ionomycin) on day 3 ($110 \pm 5/2.5 \times 10^5$ cells LOFU and HIFU versus $66 \pm 16/2.5 \times 10^5$ cells untreated, p<0.05, FIG. 14A), indicating that LOFU and HIFU treatment may tip the immune response towards a Th1 phenotype. However, the number of IFNγ-secreting cells decreased to pre-treatment levels in days 7 and 14, with no statistical difference amongst various groups (data not shown). Therefore, it was possible that repeated treatment of tumors with LOFU and HIFU would facilitate release of HSP and tumor antigens for periodic immunization, simulating a vaccination schedule for the induction of tumor-specific immune response.

Figures 14A, 14B, 14C, 14D, 14E:
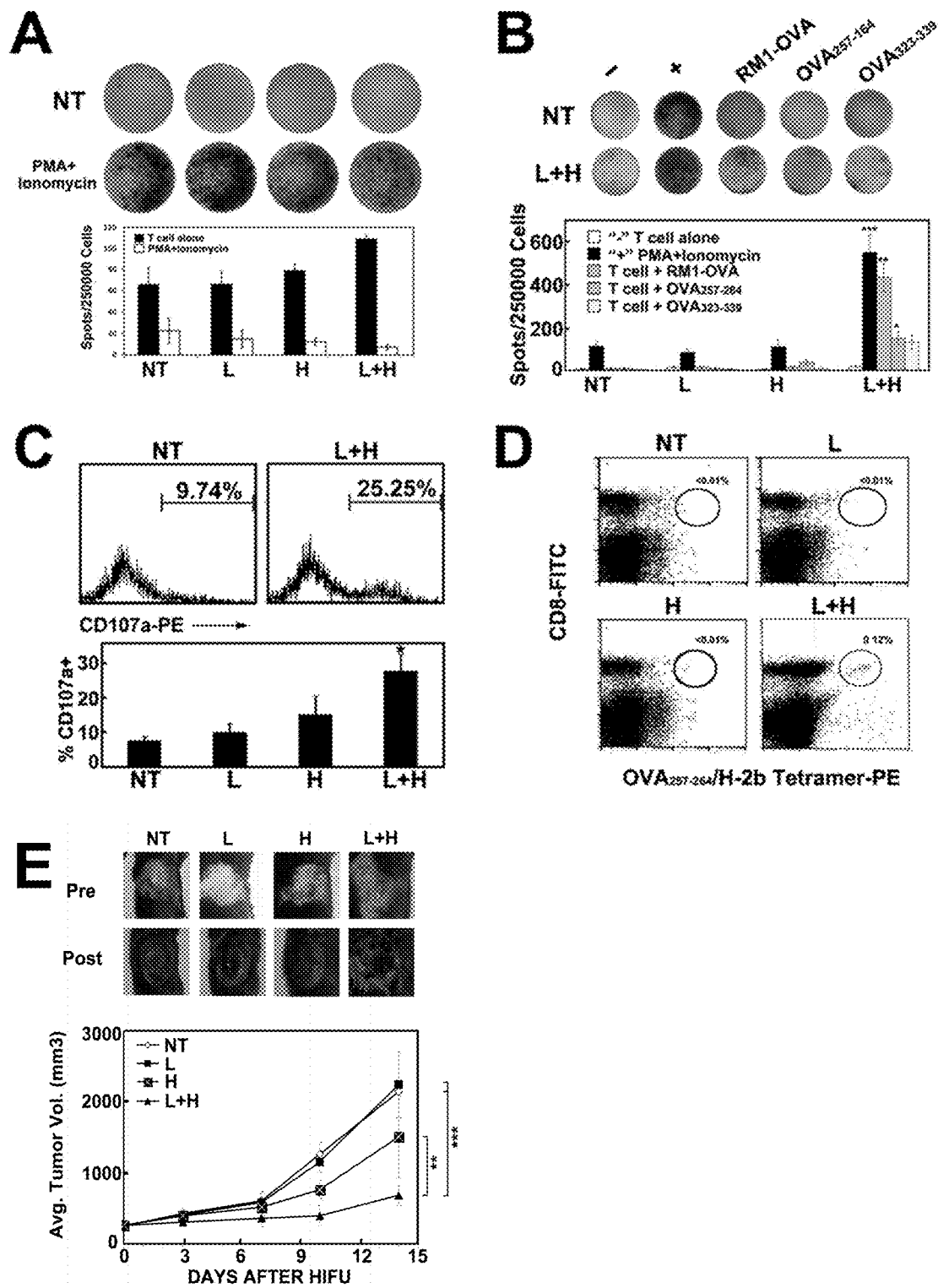

Palpable RM1-OT tumors were treated three times with weekly cycles of sequential LOFU and HIFU administered one day apart and animals were sacrificed one week after the last HIFU treatment. Frequency of tumor-specific T cells in splenocytes was analyzed by IFN-γ ELISPOT assay and cytotoxic functions of these tumor reactive T cells were detected by CD107a mobilization assay. When splenocytes from mice treated with LOFU and HIFU were co-cultured with irradiated RM1-OT cells, there was an increase in the number of IFN-γ-secreting RM1-OT reactive T cells ($432 \pm 65$ cells per $2.5 \times 105$ splenocytes after LOFU and HIFU, versus $15 \pm 6$ cells per $2.5 \times 105$ splenocytes after HIFU alone; FIG. 14B). The frequency of tumor-specific IFN-O-releasing T cells in LOFU and HIFU-treated mice was 0.17=0.03%. These tumor reactive splenocytes were also found to specifically recognize both OVA-derived MHC class I restricted peptide, OVA257-264 ($149 \pm 28$ cells per $2.5 \times 105$ total splenocytes) and MHC class II restricted peptide, OVA323-339 ($132 \pm 32$ cells per $2.5 \times 105$ total splenocytes) when co-cultured with these peptides. In contrast, no significant immune response was detected in mice treated with either LOFU alone or HIFU alone ($15 \pm 6$ cells per $2.5 \times 105$ total splenocytes in both groups). These results indicate that LOFU+HIFU combination therapy can induce both CD4 and CD8 T cell response to surrogate cytoplasmic tumor antigen, OVA. Although HIFU treatment alone induced cell death and release of intra-tumoral HSPs, it failed to induce significant anti-tumoral cellular immunity.

Tumor-specific cytotoxic T lymphocytes (CTL) were assessed by the CD107a mobilization assay, which measures the presence of cell surface CD107a in splenocytes following culture with irradiated RM1-OT cells. CD107a is a membrane protein of Perforin/Granzyme B vesicle that becomes transiently mobilized to the cell surface during the cytotoxic degranulation process by CTLs. Although, CTLs were present in all treatment groups, tumor-specific CD107a+ T cells were highest in LOFU and HIFU-treated mice ($27.88 \pm 4.80\%$ in LOFU+HIFU vs. $7.5 \pm 1.2\%$ in untreated, p<0.05; FIG. 14C). The percentage of CD8± T cells that were reactive to the surrogate tumor antigen, OVA, were quantified by H-2b/OVA257-264 tetramer staining (FIG. 14D). While, untreated or single treatment cohorts had negligible OVA-reactive CD8 T cells, there was an increase in these cells after LOFU and HIFU treatment (0.12% LOFU and HIFU vs<0.01% untreated), which further confirmed the presence of tumor specific T cells in vivo.

Lastly, to investigate whether pretreatment with non-ablative LOFU augments the therapeutic effects of HIFU, the tumor volume in murine model were measured across multiple days (FIG. 14E). The time intervals for HIFU exposure were kept the same between treatment groups. The tumor size amongst various groups was not significantly different after 1 cycle of ultrasound therapy, but the growth retardation was seen after 2 cycles. LOFU treatment alone did not alter the tumor growth rate, as compared to untreated controls (p>0.05). HIFU alone significantly suppressed tumor growth compared to LOFU and untreated cohorts (p<0.05). Pretreatment with LOFU significantly enhanced the tumoricidal effects of HIFU therapy (LOFU and HIFU vs. HIFU, p<0.01; LOFU and HIFU vs LOFU or No treatment (NT), p<0.001) as also shown by relative mouse pictures (FIG. 14E, upper panel)

LOFU system: A therapy and imaging probe system (TIPS, Philips Research North America, Briarcliff Manor, NY, USA) was utilized for all ultrasound exposures. The system includes an 8-element spherical shell annular array transducer (80 mm radius of curvature, 80 mm aperture), as well as a motion stage to allow for transducer movement and accurate positioning. The transducer was operated at 1.0

MHz, resulting in a focal spot approximately 1.5 mm in diameter and 12 mm in length (−6 dB of pressure).

LOFU treatment protocol: On treatment day, the animals were anesthetized with ketamine and xylazine (7:1 mg/ml for 100 l/mouse, i.p.). Once positioned for therapy, the tumor was acoustically coupled to the TIPS system using degassed water and ultrasound gel.

Ultrasound exposure parameters were as follows: acoustic power of 3 W and a duty cycle of 100%, yielding an approximate in situ spatial-peak temporal-average intensity ($I_{spta}$) of 270 W/cm$^2$ at a sonication depth of 3 mm in tissue, assuming an attenuation coefficient of 0.5 dB cm-1 MHz-1. Ultrasound exposures were delivered to the tumor using a 2 mm grid pattern extending over the entire tumor volume. Prior to LOFU, the tumor volume was measured to calculate the grid size for the particular treatment. The duration of LOFU exposure at each grid point was 1.5 s, after which the transducer was automatically positioned over the next grid point and the procedure repeated until the entire tumor volume was covered. This yielded a non-uniform energy delivery to the tumor.

In vitro temperature rise estimation. Estimation of intra-tumoral temperature by invasive means could undesirably modulate the therapeutic response of the combination treatment. Therefore, to estimate intra-tumoral temperature elevation using the above described setup and therapy protocol, the ultrasound exposures were performed in a 6 mm×6 mm area within a tissue-mimicking phantom, into which a T-type thermocouple (diameter 200 pm) was embedded at a depth of 3 mm. These in vitro exposures were repeated 5 times and the results averaged. Detection of Apoptosis In Situ: Apoptotic cells were detected in situ by performing TUNEL (TdT-mediated digoxigenin labeled dUTP nick end labeling) staining. Briefly, paraffin embedded sections were de-paraffinized, rehydrated through graded alcohols, and stained using an ApopTag kit (Intregen Co, Norcross, GA, USA). The apoptotic rate in tumor cells was quantified by counting the percent of apoptotic cells in each high power field.

Immunoblot Analysis: 24 hr post-LOFU the tumor cells were harvested, washed with phosphate-buffered saline, and lysed using TPER (Thermo Fisher Scientific, Rockford, IL, USA). Cell lysates were subjected to SDS-PAGE, transferred to polyvinylidene difluoride membrane, and immunoblotted with primary antibodies against PERK, pPERK, eIF2, peIF2, ERp72, ERp44, ERp57, Beclin (Cell signaling, Danvers, MA, USA), Lamp2a (Abcam, Cambridge, MA, USA), and horseradish per-oxidase-conjugated secondary antibody. The blots were developed using the ECL kit (GE Healthcare, Piscataway, NJ, USA). Densitometric analysis of immunoreactive bands of each blot was photographed and then images were digitized and analyzed by using Gel Doc XR system (Bio-Rad, Hercules, CA, USA).

Real Time PCR analysis of UPR target genes 24 hr after LOFU treatment the RM1 tumor cells were lysed using RLT buffer mixed with 1% betamercaptoethanol from RNeasy Mini Kit (Qiagen, Valencia, CA, USA).

Qiagen's protocol for the RNeasy Mini Kit with on-column DNA digestion was used to isolate RNA from the tumor lysates. The RNA samples were stored at −80° C., prior to further use. Isolated RNA was subjected to cDNA synthesis using the SuperScript™ First-Strand Synthesis System (Invitrogen, Grand Island, NY, USA). The splicing of XBP1 RNA was detected using the following primer pair 5'-ACTCGGTCTGGAAATCTG-3' (SEQ ID NO:19) and 5'-TAGCCAGGAAACGTCTAC-3' (SEQ ID NO:20) (Fisher Scientific, Pittsburgh, PA, USA). Real time PCR was performed in Light Cycler real time PCR machine (Bio Rad Laboratories, Hercules, CA, USA) using the Absolute QPCR SYBER Green Mix (ABgene, Rochester, NY, USA) according to the standard ABgene protocol. To check for primer amplification specificity, a melting curve was generated at the end of the PCR and different samples containing the same primer pair showed matching amplicon melting temperatures.

Primers used for real time PCR included GRP78

```
                                    (SEQ ID NO: 21)
    5'TTGCTTATGGCCTGGATAAGAGGG3'
    and
                                    (SEQ ID NO: 22)
    5'TGTACCCTTGTCTTCAGCTGTCAC3';

EDEM
                                    (SEQ ID NO: 23)
    5' TCATCCGAGTTCCAGAAAGCAGTC 3'
    and
                                    (SEQ ID NO: 24)
    5' TTGACATAGAGTGGAGGGTCTCCT 3'

(Fisher Scientific).
```

All the qRT-PCR and Real time PCR experiments were repeated three times. The qRT-PCR and PCR array for apoptosis genes and stem cell transcription factor were performed by SA Biosciences PCR array system (Frederick, MD, USA) according to manufacturer protocol. In brief, cDNA were prepared from purified total RNA using RT2 First Strand Kit (Qiagen) followed by PCR array using SA Bioscience PCR array kit. Data was analyzed by web based PCR array data analysis software from SA Biosciences.

Flowcytometric analysis: Flank tumors were treated with LOFU, 17AAG, and LOFU+17AAG in various cohorts. 24 hours after treatment, tumor cells were isolated by collagenase digestion and analyzed by flowcytometry for the expression of prostate cancer stem cell markers, SCA1, CD44, and CD133. Isolated tumor cells were stained with anti-SCA1 conjugated with FITC (BD Biosciences, La Jolla, CA, USA), anti-CD133 conjugated with pacific blue (eBioscience, San Diego, CA, USA) and anti-CD44 conjugated with PE (BD Biosciences, La Jolla, CA, USA). Data acquisition was performed using LSRII (BD Biosciences) and analyzed by FlowJo v.7.1 (Treestar Inc, Ashland, OR, USA) software.

Kaplan-Meier Survival analysis: Mice survival/mortality in different treatment groups was analyzed by Kaplan-Meier as a function of radiation dose using Sigma-Plot and Graph-Pad Prism (version 4.0 for OS X, San Diego, CA, USA) software.

Statistical Analysis: For digital images, sampling regions were chosen at random for digital acquisition for data quantitation. Digital image data was evaluated in a blinded fashion as to any treatment. A two-tailed Student's t-test was used to determine significant differences (p<0.05) between experimental cohorts with representative standard errors of the mean (SEM).

Example 4

FIG. 17 shows an acoustic priming therapy (APT) device, generally designated by reference number 1, according to an exemplary embodiment of the present invention. The APT device 1 is powered by an electrical power source (not shown) and includes a control system 10, amplifier 12, matching transformer 14 and transducer 16. To provide treatment, the ultrasound transducer 16 may be positioned near or within a region of the patient's body 1000. A clinician may make appropriate adjustments to the frequency and duration of the ultrasound pulses to be delivered by the transducer 16 using a function generator at the control system 10. When the ultrasound transducer 16 is excited, a transmitting surface of the transducer element creates pressure waves in the bodily fluids surrounding the ultrasound transducer 16. The pressure waves then propagate through the fluids and tissues within the patent's body 1000 and ultimately reach the target region, thereby causing a non-ablative, sonic stress to the target tissue. As explained in further detail herein, the sonic stress delivered to the tissue may have many therapeutic uses, and in the case of cancer treatment, for example, such stress of cancer cells in a tumor may result in immunogenic modulation, radio-sensitization and chemo-sensitization. The ultrasound transducer 16 may be repositioned to an adjacent area of the patient's body for further treatment.

The matching transformer 14 provides an impedance transformation between the power supply and ultrasound transducer.

The amplifier 12 generates a transducer driver signal for driving the transducer 16 based on the output signal of the control system 10. In an exemplary embodiment, the amplifier 12 may be a switched resonant power amplifier, an example of which is disclosed in U.S. Pat. No. 7,396,336, the contents of which are incorporated herein by reference in their entirety. In another embodiment, low impedance ultrasound driver-transducer systems can be employed.

The transducer 16 generates acoustic power between 10 and 1000 W/cm$^2$ spatial peak temporal average intensity ($I_{spta}$) in a treatment zone. The ultrasound is applied continuously for a time in the range of from 0.5 to 5 seconds, wherein the frequency is in the range of 0.01 to 10 MHz. In some embodiments the minimum diameter of any ultrasound beam in the treatment zone is about 1 cm.

FIG. 17 shows an acoustic priming therapy (APT) device, generally designated by reference number 1, according to an exemplary embodiment of the present invention. The APT device 1 is powered by an electrical power source (not shown) and includes a control system 10, amplifier 12, matching transformer 14 and an ultrasound transducer 16. To provide treatment, the ultrasound transducer 16 may be positioned near or within a region of the patient's body 1000. A clinician may make appropriate adjustments to the frequency and duration of the ultrasound pulses to be delivered by the transducer 16 using a function generator at the control system 10. When the ultrasound transducer 16 is excited, a transmitting surface of the transducer element creates pressure waves in the bodily fluids surrounding the ultrasound transducer 16. The pressure waves then propagate through the fluids and tissues within the patient's body 1000 and ultimately reach the target region, thereby causing a non-ablative, sonic stress to the target tissue. As explained in further detail herein, the sonic stress delivered to the tissue may have many therapeutic uses, and in the case of cancer treatment, for example, such stress of in a tumor may result in immunogenic modulation, radio-sensitization and chemo-sensitization of cancer cells. The ultrasound transducer 16 may be repositioned to an adjacent area of the patient's body for further treatment.

The matching transformer 14 provides an impedance transformation between the power supply and ultrasound transducer 16.

The amplifier 12 generates a transducer driver signal for driving the transducer 16 based on the output signal of the control system 10. In an exemplary embodiment, the amplifier 12 may be a switched resonant power amplifier, an example of which is disclosed in U.S. Pat. No. 7,396,336, the contents of which are incorporated herein by reference in their entirety. In another embodiment, low impedance ultrasound driver-transducer systems can be employed.

The transducer 16 generates acoustic power between 10 and 1000 W/cm$^2$ spatial peak temporal average intensity ($I_{spta}$) in a treatment zone. The ultrasound is applied continuously for a time in the range of from 0.5 to 5 seconds, wherein the frequency is in the range of 0.01 to 10 MHz. In some embodiments the minimum diameter of any ultrasound beam in the treatment zone is about 1 cm.

In the embodiment shown in FIG. 17, the frequency of ultrasound generated by the APT device 1 is in the range of about 10 KHz to about 300 KHz. However, the APT device according to the present invention may generate higher frequencies such as, for example, frequencies in the range of about 300 KHz to about 3 MHz.

As shown in FIG. 18, an embodiment of such an APT device, generally designated by reference number 100, may include a control system 110, amplifier 112, matching transformer 114 and transducer 116, such components having the same function and structure as previously described with reference to FIG. 17. In embodiments, the transducer 116 may be a flat or concave piston-type transducer comprised of single or multiple elements that convert another type of energy to acoustic energy.

As shown in FIG. 19, the APT device 1 and APT device 100 may be integrated into a single system, generally designated by reference number 200, to provide improved efficacy and/or lower overall energy input. The integrated system 200 provides focused low frequency and collimated high frequency beams for APT treatment. In some embodiments the low frequency ultrasound is substantially focused according to what is achievable for a given frequency or range of frequencies and the mid frequency is collimated. In some embodiments the transducer used to produce the low frequency is concave and the transducer used to produce the mid frequency is planar.

As shown in FIGS. 20-22. the APT device 1, 100, 200 may operate in conjunction with an ultrasound monitoring system, generally designated by reference 300. The ultrasound monitoring system 300 may be powered by an electrical power source (not shown) and includes a control system 310, amplifier 312 and pulse receiver system 314. The ultrasound monitoring system 300 may be used to monitor and/or provide imaging of the target tissue prior to, during and/or after APT treatment, and in particular the pulse receiver system 314 may include a transducer that receives pressure waves reflected from or generated by or from within the target tissue and the amplifier 312 generates electrical signals corresponding to the received pressure waves. The control system 310 generates output based on the electrical signals that can be used by a clinician to determine treatment status and/or other parameters. Although the ultrasound monitoring system 300 is shown as a separate component from the APT device 1, 100, 200, it should be appreciated that the monitoring and APT delivery may be performed by a unitary system.

In some embodiments, the ultrasound monitoring system 300 is used to provide information on the location of tissue to be treated. One or more, non-therapeutic ultrasound transmit and receive sub-systems may be used to monitor APT treatment and the effects of treatment on tissues.

In some embodiments, the data collected and used for planning radiation treatment are also used at least in part for planning ultrasound treatment.

In some embodiments, the data collected for APT treatment planning or APT treatment is used in radiation treatment planning. In some embodiments the data collected for radiation treatment planning is used for APT treatment planning. In some embodiments the data collected during APT treatment is used in radiation treatment planning.

In some embodiments, ultrasound is applied at a lower frequency to treat a particular location or locations identified in part by ultrasound imaging performed at a higher frequency.

Various ultrasound-based imaging and monitoring modalities may be used to monitor power deposition in tissues during APT treatment. In some embodiments, tissue temperature may be monitored via acoustic means.

In some embodiments, ultrasound elastography is used to monitor treatment. In some embodiments, harmonic imaging is used to monitor treatment. In some embodiments, thermal strain is measured. In some embodiments, the system is comprised of one or more ultrasound transmit and receive transducer sub-systems used to measure tissue strain. Tissue strain information may be used to aim the treatment ultrasound beams to a desired tissue and, in some embodiments, prior to applying full treatment power to treatment transducers. For example, in one embodiment, power is applied at 10 to 50% of the planned treatment power to one or more of the treatment transducers for 1 to 3 seconds and strain of the target tissue is measured using ultrasound feedback. APT transducers treatment intensity, application time, or both may be modulated or the transducers may be physically or electronically repositioned or more effectively directed to the target tissue based on strain imaging. In some embodiments, the full power planned for treatment is applied from one or more transducers, but the time is shorter than that used for therapeutic effect during the strain measurement period until a desired targeting is confirmed.

In some embodiments, thermometry is used to monitor treatment. Temperature on the surface or within the patient may be measured using various methods, including but not limited to thermocouples, fiber optic probes, certain MRI pulse sequences, and ultrasound thermal strain imaging.

Each transducer of the APT system 1, 100, 200 may be a single transducer or may be an array of a plurality of transducers. FIG. 23 is a perspective view of a transducer, generally designated by reference number 400, according to an exemplary embodiment of the present invention. The transducer 400 includes an array of transducer elements 402. Any number of transducer elements 402 may be sequentially arranged along the azimuth axis. The transducer elements 402 are supported on a backing block 404. Signal leads to couple the electrode of each transducer element 402 to transmit and receive circuitry as is well known. The transducer elements 402 convert electrical signals provided by the transmit circuitry to pressure waves.

In some mid frequency embodiments (about 300 KHz to about 3 MHz), two or more ultrasound transducers generate ultrasound beams that intersect within a treatment zone, herein denoted an intersection zone, with each beam having an $I_{spta}$ in the intersection zone in the range of 10 to 500 W/cm². In embodiments, two transducers generate ultrasound beams that intersect within a treatment zone, with each beam having an $I_{spta}$ in the intersection zone in the range of 20 to 200 W/cm². In embodiments, three transducers generate ultrasound beams that intersect within a treatment zone, with each beam having an $I_{spta}$ in the intersection zone in the range of 20 to 300 W/cm².

In some embodiments, the plurality of beams are substantially in phase with one another. In some embodiments, two ultrasound beams emanating from separate ultrasound transducers are substantially in phase and intersect within a treatment zone, and each beam has an acoustic power spatial peak intensity in the intersection zone in the range of 20 to 100 W/cm² and the ultrasound is applied continuously for a time ranging from 1 to 5 seconds. In some embodiments, three ultrasound beams emanating from separate ultrasound transducers are substantially of the same frequency and in phase and intersect within a treatment zone, and each beam has an acoustic power spatial peak intensity in the intersection zone in the range of 50 to 70 W/cm² and the ultrasound is applied continuously for 1 to 5 seconds.

In some embodiments, beams originating from separate transducers or transducer elements each produce an $I_{spta}$ of approximately 300 W/cm² in the treatment zone. In some embodiments beams originating from separate transducers or transducer elements each produce an $I_{spta}$ of between 10 and 100 W/cm² in a treatment zone.

In some embodiments, at least one transducer diameter and the ultrasound beam emanating from this transducer is substantially larger than the treatment zone. The use of one or more of such large transducer in combination with smaller transducers advantageously allows for less precise aiming of a high power, high volume beam while achieving effective and faster treatments.

In some embodiments, an intense treatment zone is formed where two or more beams cross paths, the intense treatment zone being equal to or greater than about 1 cm perpendicular to the transmitted energy direction and also equal to or greater than about 1 cm parallel to the transmitted direction.

In some embodiments, acoustic pressure applied to a treatment zone from each transducer is 0.1 to 10 MPa.

In some embodiments, the number of transducers that provide the intense ultrasound treatment zone is between 1 and 1000.

In some embodiments, one or more central frequencies are employed during treatment with central frequencies ranging from about 100 kHz to 20 MHz.

In some embodiments, the ultrasound from a given transducer is applied continuously. In some embodiments the ultrasound emanating from a given transducer is applied in pulses with repeating on time units and off time units known as a duty cycle. The duty cycle may be in the range of 1 on time units to 9 off time units.

In some embodiments, the transducers transmit single frequency tones or multi-frequency chirps.

In some embodiments, the transducers are operated sequentially such that the total energy delivered to the target tissue for the entire course of the application is greater than that to surrounding tissues.

In some embodiments, the frequency is swept during application, in part to reduce undesirably high intensity zones in the zones near the transducers.

In some embodiments, the transducer comprising treatment head is mechanically vibrated.

In some embodiments, the transducers are comprised of 2 dimensional phased arrays, annular arrays and/or three-dimensional phased arrays.

In some embodiments, one or more ultrasound transducers are incorporated into one or more endoscopic devices.

The APT treatment systems disclosed herein have a low thermal dose compared to thermal dosing schemes common in hyperthermic and ablative thermal therapies. In some embodiments, the maximum temperature reached in a treatment zone is about 45° C. or less during a treatment that lasts about 2 seconds or less. In some embodiments, the maximum temperature reached in a treatment zone is about 45° C. or less during a treatment that lasts about 3 seconds or less. In some embodiments, the maximum temperature reached in a treatment zone is about 50° C. or less during a treatment that lasts about 2 seconds or less. In some embodiments, the maximum temperature reached in a treatment zone is about 50° C. or less during a treatment that lasts about 3 seconds or less.

In consideration of thermal dose it is expected that therapeutic effect is obtained in part through a thermal mechanism. While not wishing to be bound by theory, mechanical effects coupled with thermal effects may explain in part observed efficacy of treatments using disclosed devices, systems and methods.

In some embodiments, coupling media is used between the transducers and the patient's body to efficiently transmit ultrasound waves and in some embodiments to provide a desired distance between a transducer and a treatment zone. In some embodiments, the coupling media is circulated to cool the transducer or the patient's body or both during treatment. Separate fluids may be used for purposes of transmitting ultrasound, providing spacing and providing cooling to the patient and system components.

While not bound by theory, APT treatment using the systems described herein can promote interactions between cells, and between cells and matrix proteins. Interactions between cancer cells and immune cells and interactions between immune cells, for example T Cells and DCs.

In some embodiments, APT treatment may disrupt protein complexes, for example protein folding complexes.

For patients with diseases that benefit from treatment with multiple modalities, permeation of entire targeted treatment zone and lesions within these zones, ease of application and short duration treatments of each modality is desirable.

Various other aspects of the APT treatment device and APT treatment modalities according to exemplary embodiments of the present invention will now be described:

Positioning apparatus

In some embodiments, transducer applicators are designed so that they may be hand-held by the clinician or care giver. In some embodiments, applicators are mounted to a mechanical positioning device, such as the positioning device 500 illustrated in FIG. 24. The positioning device 500 may be manually manipulated or robotic controlled. In the present embodiment, the positioning device 500 is an arc-shaped rail on which the transducer travels, and in particular the transducer may be attached to a cable-driven carriage that is in turn mounted on the rail. The rail itself may be rotatable so that the transducer can be positioned in three dimensions. The positioning device 500 may be large enough that a patient can fit underneath and within the target range of the transducer. Although FIG. 24 shows only one transducer positioned on the rail, it should be appreciated that more than one transducer may be disposed on the rail and/or other rails may be provided that support one or more other transducers. In some embodiments, a stewart platform, sometimes referred to as a hexapod, may be used in the positioning apparatus. Computer programming may be used to set treatment parameters and operate positioning apparatuses.

Equipment and Patient Cooling

In some embodiments, the treatment system comprises patient cooling mechanisms to cool the skin exposed to ultrasound energy or other energy.

TABLE 3

Non-limiting examples of energy sources that can be used for immune priming to elicit anti-tumor responses.

| Energy source | Parameters |
|---|---|
| Irreversible Electroporation (IRE) | 30 s-3 min |
| Microwave | Power: 1-10 W<br>Duration: 1 s-1 min |
| Low-Intensity Focused Ultrasound (LOFU) | Acoustic power: 0, 3, 6, 9, 12, 16, 32 W<br>Peak negative pressure = 2.46, 3.34, 4.58, 6.08, 8.14 MPa<br>Thermal energy: 0.3, 2.5, 5, 7.5, 10 J<br>Duty cycle: 1, 25, 50, 75, 100%<br>In situ intensity: 1 W-1000 W/cm$^2$<br>Duration: 0.5-5 s |
| High-Intensity Focused Ultrasound (HIFU) | Acoustic power: 1-20 W<br>In situ intensity: 1000-2000 W/cm2<br>Duration: 1-10 s |
| Radiofrequency | Sub-ablative radiofrequency |
| Cryotherapy | |

Acoustic Priming System

In some embodiments, the acoustic priming therapy (APT) has the potential to transform current therapies into highly effective in situ vaccines. For example, the combination of AP with hypofractionated radiation therapy may reverse T cell tolerance and eliminate melanoma metastasis to the lung in an animal or human melanoma model, and cancer with patients, for example. The animal model may be a dog or a mouse animal model, and humans can be treated similarly. In some instances, APT can be combined with radiotherapy (RT) to reduce overall toxicity, reduce the ionizing radiation dose and produce unique immunogenic tumor microenvironment (TME) damage patterns that are distinct from and more potent than that achievable by RT alone. In some instances, TME remediation may be achieved and metastatic and vascular niches may be modified. Combined effect mechanisms may be elucidated but remediation begins with damage induced reprogramming at the cellular level through tumor cell ER stress induction (primarily AP), DAMPs (AP and RT), and ROS & DNA damage (primarily RT). DC activation, migration lymph nodes, cytotoxic T cell activation and migration to tumor bed may ensue.

The damage induced reprogramming at the cellular level can be induced in many ways with energy treatment, such as non-ablative energy treatment. Each of the energies shown in Table 3 can be used to induce reprogramming at the cellular level, and this treatment can be combined with any of the treatments shown in Table 2, and combinations thereof. For example, dendritic cell targeted therapy, effector T cell targeting or immune checkpoint inhibition, can be combined with Irreversible Electroporation (IRE), Microwave, Low-Intensity Focused Ultrasound (LOFU), High-Intensity Focused Ultrasound (HIFU), Radiofrequency, or Cryotherapy, and combinations thereof.

The dendritic cell targeted therapy may comprise a material selected from the group consisting of Flt3L, CD40L, GM-CSF, ligands and agonists, RIG1 helicase activators, anti-CD40, NKG2D ligand, anti-CSFIR, anti-TLR, TLR ligands, INF-α, and TNF-β.

The effector T cell targeting may comprise a material selected from the group consisting of anti-OX40, 4-1BBL, anti-foxp40, TGF-β inhibitor, anti-CD137, artificial immunological synapse for T-cell activation, anti-CD47, anti-CD27, and anti-GD2.

The immune checkpoint inhibition may comprise a material selected from the group consisting of anti-CTL4, anti-PD1, anti-VISTA, tim3, and IDO inhibitor (e.g., Norharmane, Rosamarinic acid, COX-2 inhibitors, 1-Methyltryptophan, Epacadostat, navoximod).

In some embodiments, the acoustic priming (AP) system is configured to produce a variety of ultrasound fields. Potentially relevant features may comprise broad transverse field dimension, lower intensities and multiple frequencies. The AP-1 system may comprise a 4 channel unit that is configurable to deliver 1 to 4 frequencies with up to 16 transducer elements in range of 0.1 to 4 MHz. In other instances, the AP-1 system may comprise two transducers. The dual frequency configuration may be in use with one transducer operating above 1 MHz and one operating at 250 kHz. The intensities may be within a range from 100 to 500 $W/cm^2$ in a treatment zone. The AP system may comprise between 5 to 15 mm transverse beams for use on treatment volumes in mouse tumor models or other treatment modalities such as tumors in human patients. The control treatment volume may overlap with non-ablative ultrasound (US) fields that are of different frequencies or incoherent. The AP system may be configured for use of 1 to 4 transducers per channel. The treatment time may comprise between 1 to 3 seconds per treatment volume, and a plurality of volumes scanned to treat the tumor. In some instances, shortened overall treatment time may be afforded by a large volume of beam intersection focal region. For example, a 1.2 cm transverse×2.0 cm axial ellipsoid can produce a 1.5 cc volume treatment zone. In another example, a 110 cc (~6 cm diameter) tumor could be treated in about 220 seconds.

FIG. 25 shows an acoustic priming (AP) system in accordance with embodiments. The AP system comprises a user interface, such as a computer display coupled to a computer such as a laptop computer. The laptop computer can be coupled to a controller. The controller can be coupled to a linkage such as a robotic arm. One or more ultrasound transducers as described herein can be mounted on the end of the linkage such as the robotic arm in order to control placement of the ultrasound transducer(s) on the patient.

The AP system can be configured for clinical treatment on humans and large animal experiments, and may incorporate CT based treatment planning. For example, a Graphical User Interface (GUI) can be provided on the display of the acoustic priming system of FIG. 25. FIG. 26 shows a CT based treatment planning for a soft-tissue sarcoma, such as canine soft tissue sarcoma. The AP system may comprise US elastography-based treatment monitoring, which can be mounted on the linkage such as the robotic arm. The dose monitoring feedback control system may be specifically designed for non-ablative AP treatments, for example. The treatment temperatures can be assayed using thermal strain imaging and can be kept below 50° C., for example. The non-ablative nature of the treatment may require less precision in registration and deposition. The simplified hardware design can produce a substantially lower cost of goods and user friendly design.

The AP system may be configured for use in the treatment of a solid surface or up to 8 cm deep malignant tumors (that are either candidates for an initial course of radiotherapy or are recurrent or progressive despite conventional therapy). In the unit, US energy with certain desired frequency and spatiotemporal parameters as described herein may be directed to lesions to modulate the lesion environment. In the case of cancer, acoustic priming therapy (APT), in combination with Stereotactic Radiation Therapy (SRT) and/or in some cases other treatment modalities, can activate anti-tumor components and functions of the innate and adaptive immune system, ultimately alleviating cancer-associated dysfunctions. The benefits of APT may include fast, non-invasive, bloodless, "point on click" harnessing of a patient's tumor to generate a potent in situ vaccine against disseminated disease. The systems as described herein are capable of delivering ultrasound with desired intensity, frequency and focal size parameters are in use for mouse cancer model or other treatment modality studies such as large animal and human.

In some embodiments, the prototype unit may be built and bench testing, toxicity testing, and treatment of tumors may be used in companion animal or human cancer patients. The companion animal may be a dog. A conceptual illustration of the unit and GUI displaying CT segmentation data that will be used for treatment planning is seen in FIG. 26 (the treatment couch is not part of the system).

In some embodiments, the acoustic priming treatment system may comprise an ultrasound treatment subsystem, a robot sub-system, and an ultrasound diagnostic subsystem. The ultrasound treatment subsystem may comprise generator electronics and transducers to produce a treatment zone of about 10 mm in traverse direction and 20 mm in axial dimension. There may be at least two different transducer elements that generate ultrasound at two different frequencies, with one being low frequency of less than about 400 kHz and one high frequency of greater than about 400 kHz. In some instances, since the treatment beam treatment zone produces a volume that is smaller than typical tumors to be treated and also manages exposure of healthy tissue outside of the treatment zone, a computer controlled motorized robot sub-system may be used.

The ultrasound diagnostic subsystem may be comprised of separate transducer "probe" than that used for treatment generation. In other instances, such subsystem may position the treatment head and use elastography to monitor treatment effect on tissues. In other instances, CT DICOM data is segmented for treatment planning.

The hardware and software architectures are provided in FIGS. 27 and 28. As shown in. FIG. 29, the sub-systems may comprise a positional-scanning robot to deliver ultrasound therapy, ultrasound diagnostic image analysis algorithms for treatment planning, intra-treatment motion tracking and intra-treatment dose delivery verification/measurement. Treatment modulation using ultrasound elastography may be integrated for the system architecture. Specific software tasks such as bench testing of US treatment and thermal strain speckle tracking subsystems, integration code for robot registration and movement into acoustic priming treatment system software, design and code treatment algorithms using CT segmentation based treatment planning, integration of all acoustic priming treatment system software modules into the working system, ultrasound speckle tracking closed loop algorithm integration, definition of spatial resolution and temperature sensitivity of strain imaging, and development of deep learning algorithms that incorporate tumor focal treatments may be designed. In other instances, components such as (i) 3D ultrasound image construction and segmentation for use in treatment planning and monitoring, (ii) tumor vasculature imaging, and (iii) the development of machine learning algorithms that combine biomarker data, including imaging, tumor biopsy, liquid biopsy and acoustic priming treatment system data in adaptive treatment planning during the course of treatment may be produced.

In some embodiments, the acoustic priming treatment system unit may comprise the following general system requirements and can be described with other components are described herein. The acoustic priming treatment system may treat unwanted tissue within about ten centimeters of the body surface. The targeted tissue can include unwanted tissue as well as a margin surrounding the unwanted tissue. The acoustic priming treatment system may comprise an ultrasound-generating power supply and controller, treatment applicator, and motorized robot for positioning and moving the treatment applicator. The acoustic priming treatment system may comprise a stand-alone system capable of performing the procedure, and can include the necessary displays, operator controls, ultrasound delivery system. In some instances, the acoustic priming treatment system unit may comprise a centralized electronic control system and can provide physician control over the procedure. The acoustic priming treatment system may comprise a controller means by which the treatment can be applied while maintaining a safe temperature for the patient's healthy tissues, such as the skin. The temperature monitoring software may record a thermal record for each temperature probe throughout the treatment. A GUI and software may be used for entering patient information, treatment planning information, treatment parameters, and tracking the procedure. All patient contacting materials may have established biocompatibility, as is known to one of ordinary skill in the art.

In some embodiments, the acoustic priming treatment system unit may comprise ultrasound treatment subsystem, ultrasound applicator, a central cart, robot sub-system, treatment applicator, and ultrasound diagnostic subsystem. The ultrasound generating subsystem may comprise an ultrasound signal generation and power appropriate to provide the desired field parameters, including intensity, frequency and duty. In some embodiments, the components of the acoustic priming treatment system may be transported by a central cart or attached to the patient table. The central cart may comprise wheels for easy transport. The wheels may be immobilized to prevent the cart from accidentally moving during a procedure. The cart may comprise 4-wheel steering for easy maneuvering. In other instances, the cart may not be easily tipped over. The system may be equipped with a minimum 12 foot hospital grade power cord. The power supplies may allow use in countries with various standard voltages by switching the cable without having to switch the power scheme. The cart may provide a means to store the power cord either on the back or within the cart. The unit may also comprise a support arm. The support arm may provide support and enable the robot to be positioned as desired in proximity to the patient. The support arm can include all necessary electrical and water conduits and connections. In other instances, the support arm may comprise vertical height adjustment so that the lowest surface of the treatment head can be adjusted to treat patients positioned on a treatment couch, for example between 80 and 160 cm from the floor. In some instances, the support arm may be on swivel casters and capable of being maneuvered to and away from the treatment table.

In other embodiments, the unit may comprise a linkage such as a robotic arm. The robotic arm may comprise a support weight of treatment applicator. The robotic arm may allow the focal region of the ultrasound treatment beams to be moved and positioned as desired. The robotic arm can move at a rate of 100 mm/see in any linear direction. In some embodiments, the unit may comprise a treatment applicator. The treatment applicator can provide a means for proper positioning of the applicator for treating targeted tissues. In some instances, the treatment applicator may not unduly compress the patient's tissue such that the tissue is undesirably moved as confirmed by CT or ultrasound imaging. The treatment head may contain one or more US treatment transducers. The treatment applicator may apply ultrasound such that the targeted tissue does not exceed 55 °C for any continuous 3 second period. The treatment applicator may apply ultrasound such that the tissue outside of the desired treatment zone does not exceed 45° C. for any continuous 3 second period. All surfaces of the treatment applicator that can come in contact with the patient can be fabricated of biocompatible materials. Ultrasound transmitting materials may be provided between the applicator and the skin. The materials may function to cool the skin if needed such that skin temperature will not exceed 43° C. during any one minute period. The treatment applicator may be ergonomically designed to favor treatment of particular anatomies and parts of the body, for example the human breast, the human prostate, the human applicator and neck. The transducers in the treatment applicator may be capable of operating at 100% duty for a period of 10 minutes minimum and may be capable of repeating this cycle a minimum of 1000 times. The treatment applicator may be liquid cooled. In other instances, the treatment applicator supplied with degassed water may be water based. The total weight of the treatment applicator may not exceed 1 kg, for example. In other embodiments, the unit may comprise power supplies. The power supply may comprise an RF power supply. The RF power supply may have an input bus for external control. The duty cycle may be adjustable from 0.05 to 1.0. The pulse width may be adjustable from 1 microsecond to 1 ms..

In some embodiments, the unit may comprise thermometry control circuit. The control circuit may include fiber-optic or thermocouple temperature probe readout with over-temperature or "alarm" output capability for each channel. The control circuit may comprise temperature probes to monitor critical components temperature. The control circuit can comprise temperature probes to monitor the surface temperature and to insure patient comfort. The control circuit can comprise temperature probes for insertion into the patient in areas of high ultrasound intensity to prevent overheating of tissue. The control circuit can comprise at least one calibrated alternating magnetic field (AMF) probe to monitor AMF amplitude at a location whose relationship to the field map is documented and calibrated and which can be used to monitor AMF amplitude in the treatment area prior to treatment. The control circuit can comprise a circuit to accept the voltage output of the AMF probes, allowing the assignment of an "alarm" point and output an "alarm" signal when the preset value is exceeded. The control circuit can comprise a CPU to monitor all temperature and AMF amplitude "alarm" outputs and send an appropriate signal to the RF Power Supply to curtail the treatment. In other embodiments, the unit may comprise a thermometry system. The thermometry system can include a fiber-optic temperature probe controller with over-temperature or "alarm" output capability for each channel. The system controller may comprise an output bus to send a logic signal when the specified condition is met. The thermometry system may provide an output to control the AMF amplitude based on peritumoral temperature. Two temperature probes may be used for a treatment. The probes may be able to be administered into the target tissue as well as in the surrounding tissue, for example in the form of a hypodermic needle. The surface texture of the temperature probes may be smooth to touch. The temperature probe connecting wires may have a kink resistance and a 5" radius without kinking. The temperature probes may have temperature durability at 48° C., complete flex should not distort readings. The temperature probes may be packaged in a sterilization compatible pouch (e.g. Tyvek bag) for protection. The temperature probes may be able to be validated for 2 complete sterilization cycles. The temperature probes must meet biocompatibility requirements. In other embodiments, the unit may comprise a cooling system. The cooling system may comprise a means to orient the cooling directly adjacent to the targeted tissue. The surface temperature of the patient may be maintained below 43° C. The patient's contacting parts of the cooling system may meet biocompatibility requirements. The cooling system may be constructed of non-metallic materials.

In some embodiments, the unit may comprise a treatment applicator that delivers ultrasound to the patient. In some configurations, the treatment applicator may be the treatment head. The ultrasound transducers may be mounted in an applicator so as to produce an intersection of ultrasound from the treatment transducers. The ultrasound transducer may comprise one low frequency transducer (<400 kHz) and/or one high frequency transducer (>400 kHz). In some embodiments, the applicator may comprise one US diagnostic imaging probe. The applicator may be sized small enough to position to treat any body part while large enough to enable the intersection of beams in a desired patient treatment zone. The maximum dimensions may be 150 mm dia×150 mm long. The maximum weight may be 1000 grams. In some embodiments, the patient ergonomic considerations may comprise companion animals and man, and anatomical location. The applicator should not interfere with and not facilitate patient body surface temperature control for superficial tumors. A maximum skin temperature of 45° C. may be applied during any 3 second time period. The transducer cooling and transducer to patient coupling media may be a water of acoustic transparent gel. The acoustic impedance matching from transducer to patient may comprise a water-filled, recirculating, degassed (<2 ppm $O_2$) bolus/coupling cone. The coupling of ultrasound exiting the patient body to acoustic absorber may be utilized.

In some embodiments, the ultrasound treatment power subsystem may comprise a power supply with multiple channels to power multi-beam transducer array. The subsystem may also comprise an ultrasound generator-controller unit with a utility requirement of 108-132 VAC, 48-66 Hz. The maximum electrical power output from power supply/generator to individual transducers/transducer element may be 100 W/channel. The ultrasound treatment power subsystem may comprise specific configurations to be determined in working with ultrasound vendors. In some instances, beams of 10 mm transverse dimension and focal maximum at 20 to 120 mm from the exit plane may be desired depending upon anatomy to be treated. In other instances, the array design and beam properties may be specified for the treatment algorithm.

In some embodiments, during image-guided treatment planning & monitoring, CT may be used prior to acoustic priming treatment system to image lesions and surrounding tissue. In subsequent systems, ultrasound imaging using one or more diagnostic probes can be used. Segmentation software and user GUI requirements can include 3D Slicer as an open source segmentation platform that can be the basis for LOFU segmentation. During treatment planning, the working dosing and safety specifications may comprise 100 to 500 W/$cm^2$ of US for 1 to 5 see through treatment zone (lesion+10 mm margin), less than 50 J of energy applied to any soft tissue volume outside of treatment zone, and less than 50 J of energy applied any bone volume outside of treatment zone. Fiducials may be used for RT to be used for treatment applicator positioning. During ultrasound monitoring of dose, the effects on tissue may be determined using B mode speckle tracking and elastography methods.

In other instances, an algorithm for defining robot treatment head motions may be used to optimize for short treatment time and for avoiding heathy tissue. In some embodiments, the robotic positioning and scanning of treatment head may comprise a robot controlled position and motion to (1) treat lesions that are larger than treatment head beam(s) focal treatment zone and to (2) reduce exposure of healthy tissues. The specifications may comprise scanning tumors with a 1 cm wide, 1.5 cm long focal zone (−3 dB) in continuous motion or in 0.1 to 1 cm steps, a scan speed up to 100 mm/see in any direction, and a positioning accuracy of +/−0.1 mm. The treatment head may be capable of treating lesion size of 10 cm in any dimension parallel to body surface, 10 cm deep (normal to body surface). The treatment head may comprise rotation of up to 360 degrees and rotation used in part to reduce dose outside of desired focal treatment volume and in healthy tissues. The position of tissue may be treated on the patient treatment bed. The maximum payload may be >2 kg. The robot architectures under consideration may be primarily 6 DoF arm with rotating head, with Stewart platform, & c-arm rotations under consideration. Selection may be based on specifications, capability & cost analysis. A 6 DOF can allow for c-arm motion when the base is mounted on the vertical surface and may be recommended form implementation. In some instances, the robot may be mounted on a surgical arm or other manually manipulated apparatus that allows it to be positioned as desired by the operator in proximity to the tissue to be treated. The robot motion algorithm may be optimized to minimize treatment time and limit healthy tissue exposure to safe levels. The visual guides and fiducial registration may be used for treatment head positioning in preparation for treatment.

In some embodiments, the hardware component may comprise the following and can be described with other components are described herein. The computer controller may be a Dell Precision 7510 core i7 8gb RAM with SDD and running Windows 10 laptop. The computer may provide sufficient performance and connection ports for ultrasound and robotic hardware. The ultrasound imaging/diagnostic probe comprise an Interson, high performing USB-connecting linear probes, and Windows supported hardware. In some instances, a 10 cm scan depth linear probe may be selected. Additionally, access to RF data, which is very useful for ultrasound strain imaging that we intend to develop to monitor LOFU dosing, may be granted. The two probes can be used in two separate systems. The robot for positioning and scanning may comprise multiple commercially available 6 DOF arms, meeting the desired range of motions, payload requirements and positional accuracy for clinical use. The ultrasound treatment subsystem may comprise purpose-built transducer power generation systems, and assemblies of particular combinations of signal generators and RF amplifiers. The subsystem may comprise transducer power electronics, signal generators and amplifiers, AWG generators and DDS, and B&K Precision makes CE Marked IEC 60601 certified signal generators. The unit may comprise at least two amplifiers (one for each transducer). The linear amplifiers may comprise E&I offers class a/b wide-band modular unit with no tuning required. This is important in a modular system where various transducers can be used, such as the use of specific imaging probes. The Apex op amp based configurations may be preferred as hardware costs may be much lower relative to an E&I solution. In this instance, the DC power supply and other requirements may be evaluated and integrated.

The integrated ultrasound power generation systems may comprise units from BioSono and Sonic Concepts. The system can provide a four channel, 75 Watts/ch US generator in the AP-1 unit. In other instances, a purpose-built, two channel system with the desired voltage and frequency specifications may be used. In some instances, a custom board may be used and may require upfront engineering but may ultimately be the preferred choice as it may be custom built, smaller in size and cost substantially less. The precision acoustics may comprise high power transducers comprised of piezoceramics and may be used at 200 kHz and higher with short focal ranges that are useful for treatment of superficial tumors. The treatment applicator auxiliary components may include water coupling degassing transducer systems, water coupling temperature control, treatment head housing and mounting parts, patient-specific transducer frames and coupling, electrical wiring, water plumbing, and harness parts. In some embodiments, other components of the system may comprise thermocouples, water degassing system, and wattmeter and oscilloscopes for electrical characterization of system components.

In some embodiments, software may comprise medical imaging and software systems integration for image-guided treatment planning, treatment module, control of system components, and GUI interface in research prototype. The architecture may be modular allowing ready integration of subsystem with particular firmware. The source control may be used for managing code. The main treatment planning interface may be built into a customized 3DSlicer application. The treatment module can control the robotic positioning system, therapeutic transducers, and thermocouple input. For US treatment monitoring, a PLUS library can interface with a diagnostic ultrasound probe, and an operating system environment and design softwares', such as Visual Studio 2013 may be used. A 7.5 MHz, 10 cm scan depth linear probe with a USB interface may be used in the prototype. *Infernos* can provide an SDK written in C #; the existing Slicer codebase in written in C++, and a C++ wrapper for the SDK may be written.

In some embodiments, the treatment algorithm development for the acoustic priming treatment system unit may be implemented as follows and can be described with other components are described herein. A raster scan pattern that is produced from a treatment plan using CT image segmentation may be used. A raster scan may be performed with each treatment volume as defined by the ultrasound field pattern, such as subjection to between 2 to 3 seconds of ultrasound. LOFU may be intended to be substantially non-ablative and to produce temperatures of less than 50° C. Diagnostic ultrasound may be used during treatment delivery, both to confirm dose delivery and to examine dose effect on tissue. At each raster position, a low "scout" dose, for instance 30% of the anticipated treatment dose, may first be administered to assess thermal and mechanical responses. Among various elastographic measurements by which ultrasound-based monitoring can be performed, a speckle tracking method identified as thermal strain imaging (TSI) can first be investigated for LOFU dose monitoring. With temperature effects of a scout dose in hand, treatment power can be adjusted, accordingly using a treatment algorithm.

In some embodiments, the prototype unit may be designed under a leaner, targeted quality system appropriate for canine or other cancer treatment modalities that are being planned and for use of that data in FDA submissions, and for early feasibility studies. The acoustic priming treatment system unit may be expected to be fabricated, bench tested, and ready for in vivo testing. Additionally, three units may be produced modified from the first prototype based in part upon use of the first unit. The unit may be suitable for use in treating companion animal cancer patients and for use of data obtained from canine clinical trials in submissions to the FDA. In addition, risk analysis, software architecture assessment, engineering tasks to complete prototype for dog and human trials, selection and procurement of transducers, amplifiers, and positioning robot, treatment applicator design and fabrication, cart specification/design procurement, including robot mounting components, selection of water degassing system, and development of software architecture may accompany the unit.

Although reference is made to a prototype for in vivo animal testing, the system described herein can be used to treat human patients.

The AP unit may comprise a combination of frequencies that can be employed in the acoustic priming treatment system unit. The prototype may comprise a modular design, which can facilitate the integration of various transducers. The AP system may comprise at most about 30, at most about 25, at most about 20, at most about 15, at most about 10, or at most about 5 transducers operating at various frequencies in the range of about 100 kHz to 4 Mz. The AP system may comprise multi-frequency operations, such as simultaneous use of low and high frequency components. The multi-frequency operations may result in multiple benefits, including reduced power requirements to achieve a desired acoustic priming effect and can produce field specific immunogenic patterns. Reducing the field intensity that is necessary to produce APT may be achieved as the single shot treatment volume is increased.

Using the shape, size and orientation two or more transducer elements within the treatment head, focal treatment zones of about 6 to 10 millimeter in diameter and 10 to 20 mm along the beam axis may be formed. For each focal zone, the transducers may be operated for 1 to 5 seconds to produce tissue temperatures in the range of 40 to 50° C. A positioning and scanning robot may be used for treatment of tumors larger than the focal zone of the acoustic priming treatment system ultrasound field. In some instances, a robotic subsystem that enables scanning of the focal zone throughout the lesion and surrounding may be incorporated into the acoustic priming treatment system equipment. The robotic subsystem may include 4 to 6 Degree of Freedom (DoF) robotic arms. FIG. 30 illustrates the desired motion and the 6 DoF robot for treating a representative large superficial tumor, typical for soft tissue sarcomas in mammals such as dogs. The motion may comprise a translational motion, rotational motion, and combinations thereof. The robot may rotate the treatment head in an annular or other pattern so as to reduce exposure of healthy tissue.

FIG. 30 illustrates such a robotic arm in accordance with some embodiments. In some instances, the robot may be used to treat large tumors that cannot be treated in a single shot for evaluation of the robot. The diagnostic ultrasound can be used in lesion mapping and treatment planning processes to validate the position and for treatment planning without CT data, for example. During US image segmentation, a precision robot may be provided, and may be mounted on the arm with the treatment ultrasound transducers. A 2D to 3D reconstruction from a scanning ultrasound probe may benefit from knowing the precise position and orientation of each 2D slice with respect to a common reference frame. The robots may be calibrated to remove as much as a few millimeters of error. The robot may be high precision with 5 micron positional accuracy. The robot may not need calibration because in part it is precision-machined from a single piece of aluminum and all distances and angles may be precisely known and may be slated for integration into the acoustic priming treatment system. The robot may also comprise a multi beam treatment head, which upon rotation increases the dose to focal zone relative to the surrounding tissue as illustrated in FIG. 31. The transducers may be of the same or different frequencies. The robotic arm may comprise a wrist and fingers with a transducer mounted on the end of each finger in order to control an orientation and a position of each of a plurality of transducers.

Ultrasound Diagnostic and Treatment Monitoring Subsystem

In some embodiments, treatment monitoring in real time and temperature measurement can be accomplished using various methods, including intra-tumor thermometry using thermocouple probes, US guided imaging or MRI guided imaging, and thermal strain imaging. The diagnostic ultrasound probes and strain imaging can be used to quantify ultrasound absorption in tissue resulting in useful validation of the desired volume being treated and as a means for monitoring and modulating the therapeutic dose. A range of tumors may be investigated, the strain with a temperature increase may be calibrated, and strain imaging with efficacy may be correlated. Thus, the ultrasound effects on the strain as functions of tumor fluidity, vascularity, and mutational load may be determined.

The ultrasound strain imaging methods may also allow for noninvasive monitoring of the ultrasound treatment. Tissues can respond as a damped oscillator to the compression and rarefaction pressure waves produced by ultrasound. AP may provide unique spatiotemporal ultrasound intensity and frequency profiles for probing tissue properties. In some instances, elastography-based assessment before, during, and after AP treatment can offer unique opportunities for imaging, treatment planning, treatment monitoring and identification of biomarkers of the tumor environment. Ultrasound-guided ultrasound therapy may provide direct monitoring of the therapeutic modality. In other instances, US-based tumor characterization can reduce the frequency and number of biopsies, and can augment the information gained in biopsies and blood work. When compared to MRI, which is used for monitoring thermally ablative HIFU treatments, US-guided US treatments may require far less expensive equipment, less infrastructure and can be more rapidly administered to the patients.

In some instances, a 7.5 MHz, 10 cm scan depth linear probe may be integrated into the acoustic priming treatment system build, for example on the robotic arm, and speckle tracking experiments may be conducted. In other instances, the LOFU treatment induced temperature change may be determined by measuring the local thermal strain. The local thermal strain may be the apparent strain caused by the change in the speed of sound based on temperature. Determining the temperature change can allow for non-invasive production of a temperature map of the entire treatment area, as opposed to one or more invasive thermocouples imbedded in the tissue, which would only give one or more discrete points. The thermal strain may be estimated by tracking the displacement of speckle in the raw RF data. The thermal strain imaging design may be initialized using a block-matching algorithm to compute the motion between the frames of RF data. For each block of the image in the current time point, the algorithm may search the surrounding neighborhood for the best matching block. The vector between the block and its best match can provide the displacement for such block. Normalized cross-correlation may be used as the similarity metric. Iterative Bayesian regularization interpolation can provide a subsample precision for locating the ideal displacement to reduce noise in the displacement image. The displacement may be used to compute the thermal strain, based on the thermal properties of the tissue. The method of measurement can be effective up to 50° C., which while not appropriate for HIFU, advantageously fits the temperature rise in acoustic priming applications at which point thermal expansion of the tissue can overwhelm the thermal strain. The temperature change due to application of treatment (5-15° C.) may be sufficient to generate useful thermal strain images (total strain of 1-2%). Normalized cross correlation implementations used to track raw ultrasound (radiofrequency) signal due to local tissue temperature charges may be determined. The two-dimensional normalized correlation between a matching kernel and a search region can form a local matching metric image. The peak value in such matching metric image may be used to determine local signal displacement. The US power system may be integrated and the treatment monitoring may be developed in gel phantoms.

Control System

A control system as used herein is a component of embodiments of the systems described herein and is configured to actuate certain functions of embodiments of the systems described herein. A control system comprises a processor.

Preclinical Testing of Acoustic Priming Treatment System Device

Based on the teachings provided herein, a person of ordinary skill in the art can conduct experiments on animals to develop a system to treat humans as described herein.

In some instances, the time of clinical development may be reduced and the immunotherapy devices may be rapidly and widely commercialized to treat certain cancers in animals and humans. Soft tissue sarcomas are about five times more prevalent in canines than humans and can occur in easily accessed superficial locations on the limbs of the dog.

In some instances, neoadjuvants can include debunking and activation of an immune response. Post-treatment resection can provide early, direct assessment of treatment effects on the TME. Since TME engineering is a primary strategy, neoadjuvant use may be particularly beneficial in establishing local effects and in determining whether these effects can produce systemic immune responses. Neoadjuvant treatments, biopsy and blood samples, and the data gained therein can be used to drive use in other indications, and in the treatment of gross disease without surgical resection. Neoadjuvant Stereotactic Body Radiation Therapy (SBRT) regimens prior to lumpectomy may be used in to treat breast cancer. The first method may comprise optimization of LOFU dose for generating immune modulatory effects in spontaneous primary cancers. The tumors may be selected from the group consisting of localized non metastatic, soft tissue sarcoma, melanoma, and mammary tumors. Three dose levels of LOFU with 6 patients per dose level may be tested. Pre and post LOFU tumor tissue samples can be collected for immune phenotyping to determine the immune modulatory effects of LOFU in the TME, and blood samples to evaluate systemic changes. The methods may be selected from the group consisting of biopsy primary tumor and blood and peripheral blood mononuclear cell (PBMC) collection, external LOFU treatment, biopsy or resection of primary tumor and draining lymph node, collection of PBMCs before and after LOFU treatment, and standard of care therapy for the patients. The readouts of the method may include immune phenotyping of tissue prior to and following LOFU. The sample may include immunohistochemical/immunofluorescence (IHC/IF) of tumor and dLN samples, flow cytometry of tumor and PBMC samples, and RNASeq of tumor samples. The IHC/IF of tumor and dLN samples may be selected from standard known markers such as hematoxylin and eosin (H&E), CD3, FOXP3, and HLA-DR. The flow cytometry of tumor and PBMC samples may be selected from T-cell activation markers (cytokine production), dendritic cells (activation markers), and myeloid cells and macrophages. The RNASeq may be conducted on one or more tumor components may be selected from T cell activation signatures, IFNs, ISGs, Anergy genes, HSPs and chaperones, and immune suppressive genes.

The second method may comprise optimization of LOFU in combination with radiotherapy and immunotherapy for generating immune modulatory effects in spontaneous primary cancers. The tumor types may be selected from the group consisting of localized non metastatic soft tissue sarcoma, melanoma, and mammary. Four regimens and six patients may be tested using LOFU and hypofractionated RT, LOFU and Immunotherapy (eg anti-PD-(L)1), Hypofractionated RT (HyRT) and Immunotherapy, and LOFU and hypofractionated RT and Immunotherapym, and Immunotherapy (anti-PD-1 or anti-PD-L1). Prior to and/or following the regimens, LOFU tumor tissue biopsy samples may be collected for immune phenotyping to determine the immune modulatory effects of LOFU in the TME, and systemic circulation. The methods used may be selected from the group consisting of biopsy primary tumor and draining lymph node with collection of PBMC, LOFU and/or RT intervention, biopsy or resection of primary tumor and draining lymph node with collection of PBMCs, and standard of care therapy. The readout may be immune phenotyping of tissue prior to and/or following LOFU.

In some embodiments, the treatment may be HyRT and a combination of HyRT and acoustic priming treatment system neoadjuvant prior to surgical resection to activate the immune system. The HyRT may be 3×10Gy. In other instances, the process may comprise a three times dose of LOFU and 10 Gy by using dual frequency. LOFU and HyRT. The output of such a treatment may comprise histological and flow cytometry assessment of resected tissue, such as tumor infiltrating lymphocytes and myeloid cells, DAMPs markers & exosomes, survival, local recurrence, distant metastasis-lungs examined by CT, and assaying of blood for neutrophil /lymphocyte ratio, immunological response (cytokine (IFN-γ), T-cell receptor diversity profiling by ImmunoSEQ TCR deep sequencing at timpanist TBD.

Human Clinical Development

Ultrasound and multi parametric MRI can provide image-guided disease staging and treatment enabling US and RT energy to be localized to PC lesions with increasing accuracy.

Device Designs for Specific Indications:

In some instances, the AP device treatment head and robot specifications may be modified for treating various tumors based on tumor size and location in the body in terms of depth, nearby organs and other tissue that may comprise susceptible treatment-induced toxicity, impeding bone and gas bodies that absorb and reflect ultrasound energy, and body contours. The acoustic priming treatment system can be used for treating various cancers, such as soft tissue sarcoma. The design of the treatment head with independently movable transducers within the treatment applicator may be used for prostate cancer and transperineal treatment in patients. Independent transducer motion within the head may require less motion of the entire treatment head by the robot to treat given tissue and can appear useful for the transperineal application. The acoustic priming treatment system can be used in the treatment of melanoma tumors. The diagnostic and treatment applicator may be utilized for treatment of breast cancer. Finally, combination equipment comprising ultrasound and electronic radiation such that AP and RT treatment can be applied simultaneously.

Optimize Ultrasound Treatment Parameters and Regimens in Mouse Models

The acoustic priming unit as described herein can be configured in many ways and may comprise a power supply with four channels capable of delivering ultrasound coherently or incoherently. The AP unit may be configured to generate frequencies from 100 kHz to 4 MHz, and can be configured to deliver ultrasound simultaneously from two high power transducers one operating above and below 400 kHz. In some instances, the AP unit may be augmented with a scanning robot (e.g. 2 DoF) to allow larger tumors to be treated and to use articulated motions to scan a larger treatment volume. In other instances, the multi-frequency AP may be combined with radiotherapy (RT) to induce (i) cancer cell stress which has a demonstrated link to MHC-peptide display T cell activation and reversal of T cell anergy, (ii) changes to tumor vasculature tumor perfusion, and (iii) reprograming of the tumor environment driving a CTL mediated acute and memory response. In some embodiments, a combined treatment may comprise ultrasound or RT with appropriately timed sequence and dosing parameters, and a bioactive chemo or immune checkpoint. Studies may be conducted to elucidate the effects of timing and intensities of ultrasound frequencies and RT dose used in AP and RT combination treatments.

Combination Treatment Sequence

In some embodiments, the dosing sequences of AP and RT that are safe, immunogenic and facilitate use in radiation oncology facilities and patient compliance may be utilized. An effective means may be produced for generating a cancer antigen(s) specific systemic CD8± T cell mediated immune response. LOFU may be administered as a neoadjuvant about 2 to 4 hours prior to high dose radiation. The timing may be a result of logistics related to the separate locations of LOFU and RT equipment. Also, work in relation to embodiments suggests that LOFU can reduce STAT3 phosphorylation about 2 to 6 hours after LOFU treatment. In some instances, RT and chemotherapy induced STAT3 phosphorylation can modulate a multitude of survival functions, such as Nf-KB and IL-6 production. The RT applied during a post-LOFU transitory period of low STAT3 activation can increase radiation damage. In elucidating and optimizing treatment associated immunogenic patterns the IL-6/STAT3 and Nf-KB pathways after various combination treatments may be characterized, and the sub-ablative treatment planned accordingly.

For the combination AP and RT therapy, to reduce anesthetization and total treatment time it may be advantageous to apply AP treatment in the minutes prior to or after radiation therapy. It can be determined whether acoustic priming that is applied closer to radiation has efficacy and therapeutic index equivalent to or better than the dosing regimen in which AP and RT are separated by hours. The changes to DAMPs pattern ROS damage, other stress markers, and tumor immune cell denizens may be examined. Initially, 1 to 3 treatments each of APT and RT doses given over the course of 5 days in initial clinical trials may be performed. As with certain hypofractionated RT schemes, the focal dosing may be completed within five days to effectively prime the immune system.

The timing and sequencing of RT and AP applications and the dose modulation of RT and AP from treatment to treatment during a five day tumor microenvironment (TME) engineering window, between local toxic treatments and arrival of tumor antigen specific CTLs as indicated by cancer-immune cycle concepts may be determined. The development categories may comprise (i) US and RT intensity and sequence and (ii) bioactive combinations.

Material Incorporation into Energy Treatments: AMPs

In some embodiments, acoustic AMPlifying and microparticles (AMPs) may be incorporated into AP regimens to increase tumor localized immunogenic damage and subsequently to deliver bioactive agents. In some instances, AMPs can be fabricated to specific sizes, compositions, architectures and stability. The AMPs may be tested for efficacy in activating DCs and tumor antigen specific effector T cell responses in tumor bearing mouse models. The AMP agents may be investigated in intravenous (IV) and intramural (IT) administration routs. In some instances, AMPs may be developed with essentially the same AP power sequence as is currently employed without AMPs. In other instances, particles may be formulated to transduce energy at most about 10-fold lower power compared to that currently used in APT. As a result, the cancer-specific immunogenic patterns may be generated that produce robust innate and adaptive responses that are effective against phenotypically-heterogeneous cancer cell populations. Such patterns may be produced by radiation synergy using one or more components selected from the group consisting of DAMPS production, priming of tumor vasculature, and reduced STAT3 phosphorylation. In some embodiments, AP treatments employing AMPs can be combined with RT. In other instances, radio sensitizing agents may be incorporated into the AMP particles.

The AP multi-frequency architecture equipment may be designed to vary mechanical and thermal stresses in large volumes. As the ultrasound frequency is lowered, mechanical disruptions may be increased for both particles and surrounding tissues. In some instances, an insensitivity of particle size, including small particles bursting under low frequency US may be produced.

Materials and fabrication methods: The size of the particles may correspond to formulations for nanodroplets as is known to one of ordinary skill in the art. The particles may comprise echogenic liposomes of less than 200 nm in diameter and microbubbles (1 to 3 micron), for example.

Timing of AP Application after Particle Administration

Ultrasound application immediately after and up to 24 hours after IV injection of AMPs may be utilized. Using AMPs in conjunction with bioactive agent dosing, particles may be formulated to concentrate ultrasound energy in tumor vascular and perivascular space and can then mechanically disrupt such spaces.

The particles may comprise perfluorinated molecules selected from the group consisting of including perfluoropropane, perfluorobutane, perfluorpentane, perfluorohexane and perfluorooctyl bromide (Perflubron). Perflubron may provide contrasts across CT, MRI and ultrasound modalities. Various lipids, including phospholipids can be used. Ceramide-incorporating nano-liposomes may be used as RT-induced ceramide production and subsequent cancer cell apoptosis and tumor vasculature can be associated with anticancer mechanisms of radiation. The formulations may be tested using Passive Cavitation Detection (PCD), in cell viability and assays, and DAMPS signaling assays. The particle formulation capabilities may be determined as a foundation for bioactive loaded and surface functionalization with tumor targeting molecules.

Material Incorporation into Energy Treatments: Bioactive Agents

In some embodiments, multi-modal treatments may be developed to elicit potent, tumor-specific CTL mediated responses using tumor-localized treatments that produce strongly immunogenic patterns and processes. Bioactive agents may be selected from the group consisting of immune checkpoint inhibitors (ICIs) including PD-(L)1 axis blockers, and those that activate and otherwise engage innate and adaptive immune system components. CD40 agonist antibody, CD27 agonist antibody and FLT3L may be used in combination with RT, in bimodal and trimodal combinations. Small molecule immune modulators may be selected from the group consisting of STING activators, and TLR agonists, for example. The chemotherapeutic and targeted therapy agents whose mechanism of action is substantially directed to cancer cells can produce immunogenic patterns, and can directly interact with innate and adaptive immune cells. In some embodiments, agents may be chosen and used to drive an effective systemic anti-cancer immune response. The agents may be PARP inhibitors or epigenetic modulators. Dosing regimens may be determined and treatments may be identified that produce complete primary tumor regression in treated tumor, and reverse CD8± T cell anergy, and produce immune memory effective for thwarting tumor growth. Tri-modal induction of immunogenicity, in part though DAMP induction and through the combination of APT, RT and bioactive agent can be determined.

STING Agonist

The presence of DNA in the cytosol can be an indicator of a diseased or otherwise damaged cell. Cyclic dinucleotides (CDNs) may be produced by the DNA sensor cyclic GMP-AMP synthase (cGAS) sensing of cytstolic DNA and by bacteria. STimulator of INterferon Genes (STING) is an ER transmembrane protein that is activated by CDAs and leads to type 1 interferon production. In some instances, inflammation may comprise type 1 IFN including CTL activation and increased NK cell cytotoxicity. RT can be effective in part through the cytostolic DNA sensing STING pathway in APCs. In other instances, the local inflammation of type-1 interferon may be effective in combination with the pattern produced by AP treatment and with antigen releasing treatments including radiation. Although in part overlapping with radiation therapy mechanisms, STING can be combined with radiation and AP. The STING agonist may be 5,6-Dimethylxanthenone-4-acetic acid (DMXAA). In some instances, STING agonists can be dosed locally to avoid systemic toxicity.

In some instances, the AMPs may be incorporated into AP regimens to increase tumor localized immunogenic damage and subsequently to deliver bioactive agents. AMPs may be fabricated to specific sizes, compositions, architectures and designed for efficacy in activating DCs, tumor antigen specific effector T cell responses in tumor bearing animal or human models.

The combination of energy-based therapies with pharmaceutical and biotechnology materials can be used to treat cancer patients. These combination treatments comprising "energy primed immunity" can address a broad array of cancers, initially guided by clinical use of the given bioactive. The bioactive may be selected from the group consisting of CTLA-4 and PD-(L)1 axis, myeloid growth factor Flt3L, CD27, toll Like Receptor (TLR) agonists, agents that modulate myeloid cells such as CSF-1R inhibitors, inflammatory damage/danger sensing agents, including cytostolic DNA sensing pathway STING agonists, and chaperones including PDI, calnexin, calreticulin, CD74, Hsp54, Hsp60, Hsp70, Hsp72, BiP, Hsp90, Gp96, clusterin and other cell surface proteins including CD47.. The mechanisms may stem in part from APT's ability to disrupt cellular processes and induce UPR, which can also account in part for AP synergy with RT. Thus, in addition to immune checkpoint inhibitors, therapeutic agents used for treatment may comprise agents selected from the group consisting of PARP inhibitors and protease inhibitor.

Digital Processing Device

In some embodiments, the platforms, systems, media, and methods described herein include a digital processing device, or use of the same. In further embodiments, the digital processing device includes one or more hardware central processing units (CPUs), general purpose graphics processing units (GPGPUs), or field programmable gate arrays (FPGAs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® jOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Referring to FIG. 32, in a particular embodiment, an exemplary digital processing device 101 is programmed or otherwise configured to operate the energy priming device as described herein. The digital processing device 1601 can regulate various aspects of the energy priming device of the present disclosure, such as, for example, performing processing steps. In this embodiment, the digital processing device 1601 includes a central processing unit (CPU, also "processor" and "computer processor" herein) 1605, which can be a single core or multi core processor, or a plurality of processors for parallel processing. The digital processing device 1601 also includes memory or memory location 1610 (e.g., random-access memory, read-only memory, flash memory), electronic storage unit 1615 (e.g., hard disk), communication interface 1620 (e.g., network adapter) for communicating with one or more other systems, and peripheral devices 1625, such as cache, other memory, data storage and/or electronic display adapters. The memory 1610, storage unit 1615, interface 1620 and peripheral devices 1625 are in communication with the CPU 1605 through a communication bus (solid lines), such as a motherboard. The storage unit 1615 can be a data storage unit (or data repository) for storing data. The digital processing device 1601 can be operatively coupled to a computer network ("network") 1630 with the aid of the communication interface 1620. The network 130 can be the Internet, an internet and/or extranet, or an intranet and/or extranet that is in communication with the Internet. The network 1630 in some cases is a telecommunication and/or data network. The network 1630 can include one or more computer servers, which can enable distributed computing, such as cloud computing. The network 1630, in some cases with the aid of the device 1601, can implement a peer-to-peer network, which may enable devices coupled to the device 1601 to behave as a client or a server.

Continuing to refer to FIG. 32, the CPU 1605 can execute a sequence of machine-readable instructions, which can be embodied in a program or software. The instructions may be stored in a memory location, such as the memory 1610. The instructions can be directed to the CPU 1605, which can subsequently program or otherwise configure the CPU 1605 to implement methods of the present disclosure. Examples of operations performed by the CPU 1605 can include fetch, decode, execute, and write back. The CPU 1605 can be part of a circuit, such as an integrated circuit. One or more other components of the device 101 can be included in the circuit. In some cases, the circuit is an application specific integrated circuit (ASIC) or a field programmable gate array (FPGA).

Continuing to refer to FIG. 32, the storage unit 1615 can store files, such as drivers, libraries and saved programs. The storage unit 1615 can store user data, e.g., user preferences and user programs. The digital processing device 1601 in some cases can include one or more additional data storage units that are external, such as located on a remote server that is in communication through an intranet or the Internet.

Continuing to refer to FIG. 32, the digital processing device 1601 can communicate with one or more remote computer systems through the network 1630. For instance, the device 1601 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iphone, Android-enabled device, Blackberry®), or personal digital assistants.

Methods as described herein can be implemented by way of machine (e.g., computer processor) executable code stored on an electronic storage location of the digital processing device 1601, such as, for example, on the memory 1610 or electronic storage unit 1615. The machine executable or machine readable code can be provided in the form of software. During use, the code can be executed by the processor 1605. In some cases, the code can be retrieved from the storage unit 1615 and stored on the memory 1610 for ready access by the processor 1605. In some situations, the electronic storage unit 1615 can be precluded, and machine-executable instructions are stored on memory 1610.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or extensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called microbrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM Blackberry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Example 5

Pilot efficacy experiments generally uses n=3 to 5/cohort. Outputs and endpoints include tumor size (one way ANOVA), survival (Kaplan-Meier, log-rank test) and met count in lung. Additionally, monitoring of tumor progression may be assayed non-invasively using various imaging modalities including IR-783 dye and an NIR imaging on IVIS instrument and PET SPECT: Inveon™ multimodal PET·SPECT·CT platform.

Definitive experiments comprise 8 to 12 animals per cohort; 3 will be sacrificed 24 hrs post-treatment for histology, 3 will be sacrificed 1 week post-Rx for tumor immunity assays, and 5 will be followed for 60 days to investigate disease progression.

Mouse cancer models may comprise B16F10 ml melanoma, TPSA23 prostate and 4T1 breast murine tumor cells inoculated and occurring in C57blck6, GEMs and Balb/c mice respectively. Both B16F10 and 4T1 can metastasize very quickly, more slowly metastasizing models can also be utilized.

Ultrasound and RT equipment comprises APT and RT directed to the inoculated tumor and the immediate periphery of normal tissue and the Region of Interest (RoI) with the intent of treating the entire ROI. The ultrasound system comprised of multiple transducers can deliver 100 to 10,000 $W/cm^2$ at 1 Mhz and 250 kHz. Generally ultrasound treatments are applied for a time from 1 to 5 seconds, at 50 to 150 $W/cm^2$ per treated cross-section.

Xstrahl Limited's Small Animal Radiation Research Platform (SARRP) is used to deliver the radiation. The SARRP unit has CT scanning and tissue segmentation and treatment planning capability. The survival, primary tumor size, and met lung count are possible endpoints.

The outputs may comprise cancer cells EMT status (vimentin stain), quantification of circulating tumor cells, Tumor Infiltrating Lymphocytes (TIL) and stromal cells in tumor environment (immunohistochemistry and FACS of lysates), intercellular, cell surface and exosome quantification of upregulated ER stress markers, including chaperons calreticulin, HSP70 and HSP90, BiP; ATP, HMGB1; hypoxia HIF-1α, and damage responders STAT3, Nf-κB (Western blot, FACS, and immunohistochemistry). The output may also comprise with respect to RT, the generation of reactive oxygen species (ROS) and nitrogen species (RNS) damage DNA, the increase in tumor cell antigenicity and augmentation of the release of antigens and DC activating-DNA. Thus, the ROS and RNS production is measured on treated tumors at different time points by using a rapid and sensitive fluorescent assay OxiSelect™ In Vitro ROS/RNS Assay Kit.

The ER stress regulators by isolating RNA from tumor treated samples and analyzed using equipment including complete RNA seq analysis or RT2 Profiler PCR Arrays can provide the detection of 370 key genes recognizing and responding to misfolded protein accumulation in the endoplasmic reticulum and regulators (i.e. Calr, ErolIb, Ppia, Scap) involved in the unfolded-protein response.

Blood assays can include CBC and neutrophil to lymphocyte ratio. The sera collected before and after treatment can be analyzed for cytokines using ELISpot and in some cases for more detailed Cytokine Mouse Membrane Antibody Array to detect up to 97 different targets including chemokines, Th1 and Th2 cytokines TNFα, INFγ, INFβ, IL2, IL,6, IL10, IL12, TGFβ, metalloproteases and growth factors. The LN and splenocyte may be INFγ and IL2 with CD8± T cell exposure to tumor lysate. When the memory T cell population warrants, at least 30 days after the disappearance of primary tumor cells, inoculation into the left flank can occur and tumor growth and effector memory T cells can be quantified. All data can be compared to untreated tumor samples.

The system as described herein can be configured in many ways, and can be configured to perform whole body scans with low intensity focused ultrasound, for example by scanning a beam to a plurality of locations.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Exemplary Embodiments

1. An ultrasound system to prime an immune system of a patient, the system comprising: a probe comprising an ultrasound transducer configured to produce an ultrasound beam comprising a beam volume of at least 0.5 cm$^3$ and an intensity within the beam volume within a range from 10 W/cm$^2$ to 900 W/cm$^2$; a processor coupled to the ultrasound transducer, the processor configured instructions treat the patient at a plurality of locations with the beam. 2. The system of embodiment 1, wherein the processor and the ultrasound transducer are configured to scan tissue volumetrically at a rate of at least about 0.5 cm$^3$ per second over a total tissue volume of at least about 2 cm$^3$ and optionally wherein the rate of scanning of the total tissue volume is within a range from about 0.5 cm$^3$ to about 50 cm$^3$ per second and optionally wherein the total tissue volume is within a range from about 2 cm$^3$ to about 1000 cm$^3$ and optionally wherein the total tissue volume is within a range from about 4 cm$^3$ to about 500 cm$^3$ and optionally wherein an entirety of the volume has been scanned with the intensity within the range. 3. The system of embodiment 1, wherein the beam volume is within a range from 0.5 cm$^3$ to 1000 cm$^3$ and optionally wherein the beam volume is within a range from 1 cm$^3$ to 500 cm$^3$ and optionally within a range from about 2 cm$^3$ to about 250 cm$^3$. 4. The system of embodiment 1, wherein the intensity is within a range from about 20 W/cm$^2$ to about 500 W/cm$^2$. 5. The system of embodiment 1, further comprising a linkage coupled to the ultrasound transducer, the processor coupled to the linkage and configured with instructions to move the transducer to a plurality of locations to treat a plurality of volumetric regions of tissue, each of the plurality volumetric regions comprising the at least 0.5 cm$^3$ and the intensity within the range from 10 W/cm$^2$ to 900 W/cm$^2$. 6. The system of embodiment 5, wherein the processor is configured with instructions to overlap the plurality of volumetric regions. 7. The system of embodiment 5, wherein the processor is configured with instructions to move the ultrasound transducer from a first position corresponding to a first volumetric region to a second position corresponding to a second volumetric region while the transducer transmits the ultrasound beam. 8. The system of embodiment 5, wherein the linkage comprises a robotic arm comprising a plurality of joints, each of the plurality of joints coupled to an actuator to control an angle of the joint and wherein the processor is configured with instructions to determine a plurality of angles of the plurality of joints to direct the ultrasound beam to the plurality of locations. 9. The system of embodiment 5, wherein the processor is configured to control an orientation of the ultrasound transducer at each of the plurality of locations in order to align the ultrasound transducer with a surface of a skin of the patient at each of the plurality of locations. 10. The system of embodiment 9, wherein the processor is configured to control an orientation of the ultrasound transducer at each of the plurality of locations in order to align the ultrasound transducer with a surface of a skin of the patient at each of the plurality of locations and optionally wherein each of the plurality of locations corresponds to a position in three dimensions and an orientation in three dimensions in order to position the transducer with six degrees of freedom. 11. The system of embodiment 5, wherein the robotic arm comprises a plurality of fingers and wherein the transducer comprises a plurality of transducers, and wherein each of the plurality of fingers is coupled a transducer mounted thereon and wherein each of the plurality of fingers is configured to control an angle of the transducer of an ultrasound beam from the transducer mounted on the finger in order to direct the ultrasound beam to a target location. 12. The system of embodiment 1, further comprising a user input for a user to specify an adjunct therapy to be combined with the ultrasound treatment, and wherein the processor is configured with instructions to record a time of treatment of the ultrasound beam to the tissue and output a time for the adjunct therapy and optionally wherein the adjunct therapy is selected from the group consisting of radiotherapy, chemotherapy and immunotherapy and optionally wherein the output time comprises a time window for the adjunct therapy. 13. The system of embodiment 1, wherein the processor is configured with instructions to provide user interface to a user, the user interface comprising an image of a tumor of the patient and input treatment locations. 14. The system of embodiment 1, wherein the processor is configured to perform tissue elastography of the total tissue volume. 15. The system of embodiment 1, wherein the processor is configured to receive diffusion parameters as input.

16. A method of treating a patient, the method comprising: administering an immunopriming energy selected from the group consisting of Irreversible Electroporation (IRE), Microwave, Low-Intensity Focused Ultrasound (LOFU), High-Intensity Focused Ultrasound (HIFU), Radiofrequency energy and cryotherapy; and administering an immunotherapy selected from the group consisting of dendritic cell targeted therapy, effector T cell targeting, immune checkpoint inhibition. 17. The method of embodiment 16, wherein the dendritic cell targeted therapy is selected from the group consisting of Flt3L, CD40L, GM-CSF, ligands and agonists, RIG1 helicase activators, anti-CD40, NKG2D ligand, anti-CSF1R, anti-TLR, TLR ligands, INF-α, and TNF-β. 18. The method of embodiment 16, wherein the effector T cell targeting is selected from the group consisting of anti-OX40, 4-1BBL, anti-foxp40, TGF-β inhibitor, anti-CD137, artificial immunological synapse for T-cell activation, anti-CD47, anti-CD27 and anti-GD2. 19. The method of embodiment 16, wherein the Immune checkpoint inhibition is selected from the group consisting of anti-CTL4, anti-PD1, anti-VISTA, tim3, IDO inhibitor, Norharmane, Rosamarinic acid, COX-2 inhibitors, 1-Methyltryptophan, Epacadostat, and navoximod.

What is claimed is:

1. An acoustic priming therapy system comprising:
a processor;
one or more ultrasound transducers coupled to the processor, wherein the one or more ultrasound transducers are configured to produce one or more ultrasound beams such that the frequency waveform of the one or more ultrasound beams has a spatial peak temporal average acoustic output intensity ($I_{spta}$) of between 10 and 900 W/cm$^2$ and a −3 dB beam profile waist of at least 5 mm; and
a probe coupled to the processor, wherein the probe is configured to monitor the patient,
wherein the processor and the ultrasound transducer are configured to scan tissue volumetrically at a rate of at least 0.5 cm$^3$ per second,
wherein a first ultrasound transducer of the one or more ultrasound transducers is configured to produce an ultrasound beam at a frequency of 300 kHz to 3 MHz and a second ultrasound transducer of the one or more ultrasound transducers is configured to produce an ultrasound beam at a frequency of between 30 kHz and 300 kHz, and
wherein the one or more ultrasound beams is a low-Intensity Focused Ultrasound (LOFU) and induces a non-ablative stress in cells of a target treatment zone.

2. The system of claim 1, wherein the processor and the ultrasound transducer are configured to scan tissue volumetrically within a range of at least 0.5 cm$^3$ to 50 cm$^3$ per second.

3. The system of claim 1, wherein the average acoustic output intensity is within a range from 20 W/cm$^2$ to 500 W/cm$^2$.

4. The system of claim 1, further comprising a positioning apparatus coupled to the one or more ultrasound transducers, the processor coupled to the positioning apparatus and configured with instructions to move the one or more ultrasound transducers to a plurality of locations.

5. The system of claim 4, wherein the positioning apparatus comprises a robotic arm comprising a plurality of joints, wherein each of the plurality of joints coupled to an actuator to control an angle of the joint and wherein the processor is configured with instructions to determine a plurality of angles of the plurality of joints to direct the ultrasound beam to the plurality of locations.

6. The system of claim 1, wherein the processor is configured to control an orientation of the ultrasound transducer at a plurality of locations.

7. The system of claim 1, further comprising a user input for a user to specify an adjunct therapy to be combined with the acoustic priming therapy, and wherein the processor is configured with instructions to record a time of treatment of the one or more ultrasound beams to the tissue and output a time for the adjunct therapy, wherein the adjunct therapy is selected from the group consisting of radiotherapy, chemotherapy, immunotherapy, Irreversible Electroporation (IRE), Microwave therapy, Low-Intensity Focused Ultrasound (LOFU), and High-Intensity Focused Ultrasound (HIFU), and wherein the output time comprises a time window for the adjunct therapy.

8. The system of claim 1, wherein the processor is configured with instructions to provide a user interface to a user, the user interface comprising an image of a tumor of the patient and input treatment locations.

9. The system of claim 1, wherein the probe is an imaging probe or a thermometer.

10. The system of claim 9, wherein the thermometer is a thermocouple or a fiber optic temperature probe.

11. The system of claim 1, wherein the probe comprises a separate transducer that measures ultrasound.

12. The system of claim 1, further comprising a cooling system configured to circulate coupling media between the one or more ultrasound transducers and the patient's body.

13. The system of claim 7, wherein the adjunct therapy is radiotherapy.

14. The system of claim 7, wherein the adjunct therapy is IRE.

15. The system of claim 7, wherein the adjunct therapy is microwave therapy.

16. The system of claim 7, wherein the adjunct therapy is LOFU.

17. The system of claim 7, wherein the adjunct therapy is HIFU.

18. The system of claim 7, wherein the adjunct therapy is chemotherapy.

19. The system of claim 7, wherein the adjunct therapy is immunotherapy.

20. The system of claim 12, wherein the coupling media is configured to provide a desired distance between a transducer and a treatment zone.

21. The system of claim 7, wherein the adjunct therapy is Fms-like receptor tyrosine kinase 3 ligand (FLT3L).

22. The system of claim 1, wherein the one or more ultrasound transducers comprise a flat piston ultrasound transducer.

23. The system of claim 22, wherein the first ultrasound transducer[s] comprises a flat piston ultrasound transducer.

24. The system of claim 1, wherein the one or more transducers are configured to produce intersecting ultrasound beams to form a target treatment zone.

25. The system of claim 1, wherein the ultrasound beam at the frequency of 300 kHz to 3 MHz and the ultrasound beam at the frequency of between 30 kHz and 300 kHz are produced sequentially.

26. The system of claim 25, wherein the ultrasound beam at the frequency of 300 kHz to 3 MHz is produced before the ultrasound beam at the frequency of between 30 kHz and 300 KHz.

27. The system of claim 1, wherein the ultrasound beam at the frequency of 300 kHz to 3 MHz and the ultrasound beam at the frequency of between 30 kHz and 300 kHz are produced simultaneously.

28. The system of claim 1, wherein the processor is configured to receive measurements from the probe and modulate the spatial peak temporal average acoustic output intensity ($I_{spta}$) or the frequency or a combination thereof of the ultrasound beam based on the measurement.

29. The system of claim 28, wherein the processor modulates the spatial peak temporal average acoustic output intensity ($I_{spta}$) or the frequency or a combination thereof of the ultrasound beam to produce a specific immunogenic pattern.

30. The system of claim 1, wherein an application of the ultrasound beam at the frequency of 300 kHz to 3 MHz and the ultrasound beam at the frequency of between 30 kHz and 300 kHz to a tissue provides for infiltration of innate and adaptive immune cells into the tissue.

31. The system of claim 1, wherein an application of the ultrasound beam at the frequency of between 30 kHz and 300 kHz to a tissue provides for infiltration and activation of myeloid cells into the tissue.

32. The system of claim 27, wherein the processor is configured to not apply the ultrasound beam at the frequency of 300 kHz to 3 MHz more than once at a target treatment zone during a treatment.

* * * * *

UNITED STATES PATENT AND TRADEMARK OFFICE
CERTIFICATE OF CORRECTION

PATENT NO. : 12,070,628 B2
APPLICATION NO. : 16/865761
DATED : August 27, 2024
INVENTOR(S) : Chandan Guha et al.

Page 1 of 1

It is certified that error appears in the above-identified patent and that said Letters Patent is hereby corrected as shown below:

In the Claims

Column 88, Lines 31-32:
In Claim 23, replace:
"The system of claim 1, wherein the first ultrasound transducer[s] comprises a flat piston ultrasound transducer."
With:
"The system of claim 1, wherein the first ultrasound transducer comprises a flat piston ultrasound transducer."

Signed and Sealed this
Twelfth Day of November, 2024

*Katherine Kelly Vidal*

Katherine Kelly Vidal
*Director of the United States Patent and Trademark Office*

SEQUENCE LISTING

<160> NUMBER OF SEQ ID NOS: 24

<210> SEQ ID NO 1
<211> LENGTH: 22
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 1
gtgacgttga catccgtaaa ga                                              22

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gccggactca tcgtactcc                                                  19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcagcatcat tgacccttc a                                                21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atgtgactgg tgagttctgc c                                               21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atgcaagagc tcaaagcagg aagc                                            24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgcgcagct gaagctttcc aata                                            24

<210> SEQ ID NO 7
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 7
gctggctctc ggaggag                                                    17

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgcacttgta caccttcagc                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgcgcacaa gctagaattt                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctttgcgtgg aaagtggagt                                                 20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcagtggttt tatgcaccag c                                               21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaagctactc ggatacggga g                                               21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 13
tcactcaagt ttgcccactg                                           20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cacagctaag caccgatgag                                           20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtgtggagtc accagaccct                                           20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcttctactt gcagcccatc                                           20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggcccttctc caggacaga                                            19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gctgatcatg gctgggttgt                                           20

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
actcggtctg gaaatctg                                                          18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tagccaggaa acgtctac                                                          18

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttgcttatgg cctggataag aggg                                                   24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgtacccttg tcttcagctg tcac                                                   24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcatccgagt tccagaaagc agtc                                                   24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttgacataga gtggagggtc tcct                                                   24